US011773403B2

(12) United States Patent
Pennell et al.

(10) Patent No.: US 11,773,403 B2
(45) Date of Patent: Oct. 3, 2023

(54) METHODS AND MATERIALS FOR HIGH THROUGHPUT TESTING OF MUTAGENIZED ALLELE COMBINATIONS

(71) Applicant: Ceres, Inc., Thousand Oaks, CA (US)

(72) Inventors: Roger I. Pennell, Thousand Oaks, CA (US); Richard Hamilton, Thousand Oaks, CA (US); Delin Liang, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 105 days.

(21) Appl. No.: 17/039,434

(22) Filed: Sep. 30, 2020

(65) Prior Publication Data

US 2021/0079413 A1 Mar. 18, 2021

Related U.S. Application Data

(63) Continuation of application No. 16/077,024, filed as application No. PCT/US2017/016908 on Feb. 8, 2017, now Pat. No. 10,876,129.

(60) Provisional application No. 62/294,539, filed on Feb. 12, 2016.

(51) Int. Cl.
*C12N 15/82* (2006.01)
*A01H 1/06* (2006.01)
*A01H 6/46* (2018.01)

(52) U.S. Cl.
CPC ........... *C12N 15/8247* (2013.01); *A01H 1/06* (2013.01); *A01H 6/4636* (2018.05); *A01H 6/4666* (2018.05); *A01H 6/4678* (2018.05); *A01H 6/4684* (2018.05); *C12N 15/8213* (2013.01); *C12N 15/8271* (2013.01)

(58) Field of Classification Search
CPC .................................................... C12N 15/82
See application file for complete search history.

(56) References Cited

U.S. PATENT DOCUMENTS

| | | | |
|---|---|---|---|
| 8,697,359 B1 | 4/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,906,616 B2 | 12/2014 | Zhang et al. | |
| 8,993,233 B2 | 3/2015 | Zhang et al. | |
| 8,999,641 B2 | 4/2015 | Zhang et al. | |
| 9,115,348 B2 | 8/2015 | Haurwitz et al. | |
| 9,688,971 B2 | 6/2017 | Doudna et al. | |
| 9,745,610 B2 | 8/2017 | Doudna et al. | |
| 10,087,431 B2 | 10/2018 | Wiedenheft et al. | |
| 10,876,129 B2 * | 12/2020 | Pennell | C12N 15/8271 |
| 2006/0123505 A1 * | 6/2006 | Kikuchi | C07K 14/415 |
| | | | 536/23.6 |
| 2008/0108502 A1 * | 5/2008 | Sanz Molinero | C12N 15/8261 |
| | | | 800/290 |
| 2014/0068797 A1 | 3/2014 | Doudna et al. | |
| 2014/0315985 A1 | 10/2014 | May et al. | |
| 2016/0017365 A1 | 1/2016 | Cigan | |

FOREIGN PATENT DOCUMENTS

WO WO 2014144155 A1 9/2014
WO WO 2015171894 A1 11/2015

OTHER PUBLICATIONS

Bateman, et al., "Pfam 3.1: 1313 Multiple Alignments and Profile HMMs Match the Majority of Proteins," Nucleic Acids Research 27(1):260-262 (1999).
Bortesi and Fischer, "The CRISPR/Cas9 System for Plant Genome Editing and Beyond," Biotechnology Advances 33(1):41-52 (2015).
Feng, et al., "Efficient Targeted Genome Modification in Maize Using CRISPR/Cas9 System," Journal of Genetics and Genomics 43(1):37-43 (2016).
International Preliminary Report on Patentability regarding International Application No. PCT/US2017/016908, dated Aug. 23, 2017.
International Search Report and Written Opinion regarding International Application No. PCT/US2017/016908, dated Jun. 28, 2017.
Ran, et al., "Genome Engineering Using the CRISPR-Cas9 System," Nature Protocols 8(11):2281-2308 (2013).
Schaeffer and Nakata, "CRISPRCas9-mediated Genome Editing and Gene Replacement in Plants: Transitioning From Lab to Field," Plant Science 240:130-142 (2015).
Smith, "Embryo Culture of a Tomato Species Hybrid," Proceedings of the American Society for Horticultural Science 44:413-16 (1944).
Sonnhammer, et al., "Pfam: A Comprehensive Database of Protein Domain Families Based on Seed Alignments," Proteins 28(3):405-420 (1997).
Sonnhammer, et al., "Pfam: Multiple Sequence Alignments and HMM-profiles of Protein Domains," Nucleic Acids Research 26(1):320-322 (1998).
Svitashev, et al., "Targeted Mutagenesis, Precise Gene Editing, and Site-Specific Gene Insertion in Maize Using Cas9 and Guide RNA," Plant Physiology 169(2):931-945 (2015).
Woo, et al., "DNA-free Genome Editing in Plants With Preassembled CRISPR-Cas9 Ribonucleoproteins," Nature Biotechnology 33(11):1162-1164 (2015).
Zetsche, et al., "Cpf1 Is a Single RNA-Guided Endonuclease of a Class 2 CRISPR-Cas System," Cell 163(3):759-771 (2015).

* cited by examiner

*Primary Examiner* — Brent T Page
(74) *Attorney, Agent, or Firm* — DENTONS US LLP

(57) ABSTRACT

High throughput methods are described for identifying combinations of mutations that can be used to improve a phenotypic feature in an organism. Large populations of organisms (e.g., plants) containing different combinations of mutations can be assessed using the methods.

23 Claims, 1 Drawing Sheet
Specification includes a Sequence Listing.

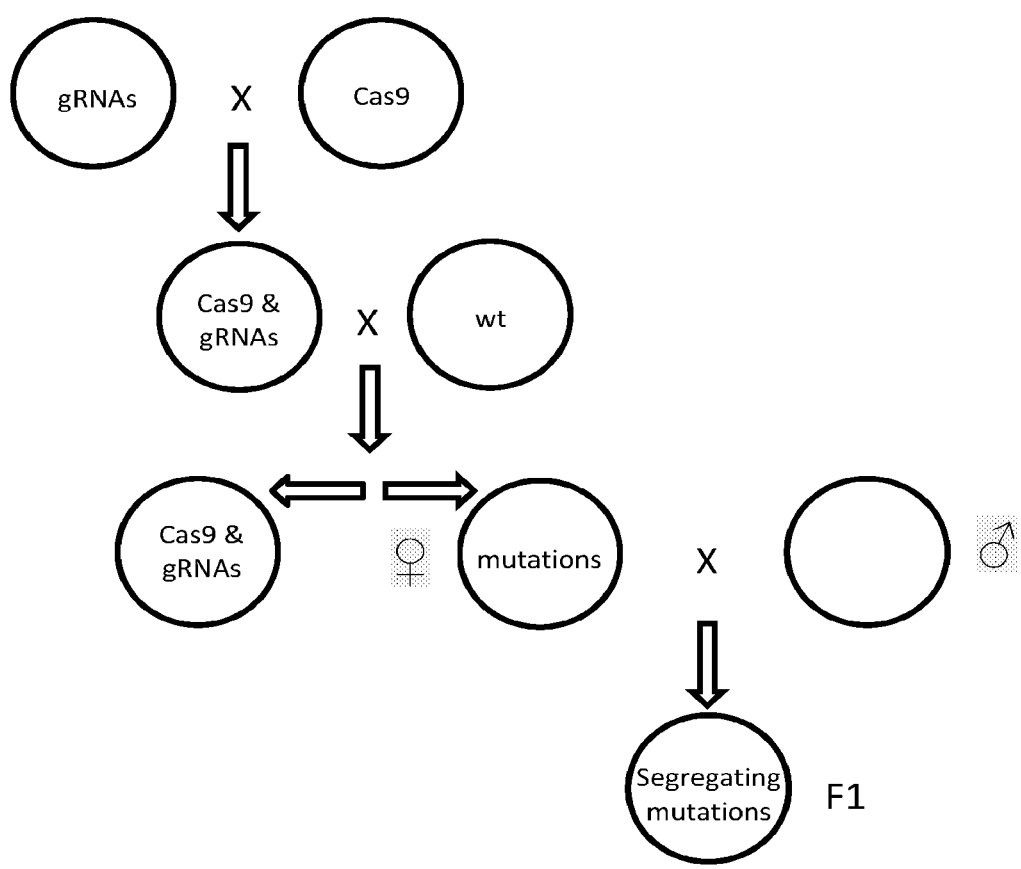

METHODS AND MATERIALS FOR HIGH THROUGHPUT TESTING OF MUTAGENIZED ALLELE COMBINATIONS

CROSS-REFERENCE TO RELATED INVENTIONS

This application is a continuation of co-pending U.S. patent application Ser. No. 16/077,024, filed Aug. 9, 2018, which application is a 35 U.S.C. 371 National Stage application of International Application No. PCT/US2017/016908, filed Feb. 8, 2017 which claims the benefit of U.S. Provisional Application No. 62/294,539 filed Feb. 12, 2016, each of which are herein incorporated by reference in its entirety.

TECHNICAL FIELD

This document relates to methods and materials involved in improving traits in organisms. For example, this document provides plants and materials and methods for making plants and plant products, where crops of the cultivated plants achieve improved agronomic characteristics or plant material quality.

INCORPORATION OF SEQUENCE LISTING

The sequence listing that is contained in the file named "CRES032WO_ST25.txt" which is 127 kilobytes as measured in Microsoft Windows operating system and was created on Feb. 7, 2017, is filed electronically herewith and incorporated herein by reference.

BACKGROUND

Modern elite varieties of cultivated plant species are generally highly bred, meaning that they have undergone a large number of cycles of artificial selection for improved agronomic traits. This process has resulted in the accumulation of a large number of favorable alleles in elite genetic backgrounds. Hence, for further improvements to elite performers, much of an existing genetic material needs to be maintained. But, generation of new genetic diversity by means of mutagenesis or wide crosses often begins with massive changes of the genetic material. A laborious isolation and evaluation process generally results in relatively few new loci that are sufficiently favorable to justify incorporation into improved elite varieties. Moreover, specific pairs of allelic variants may exhibit positive epistasis, but they may elude identification if their occurrence emerges only from random mutagenesis or recombination. A need exists for an improved system for generation of saturation or near-saturation mutagenesis of agronomic trait candidate loci and for testing the effect of combined mutations, preferably within an otherwise uniform elite genetic background.

SUMMARY

This document provides methods and materials for improving one or more phenotypic features in an organism. For example, this document provides high throughput methods for identifying combinations of mutations that can be used to improve a phenotypic feature in an organism. As described herein, large populations of organisms (e.g., plants) containing different combinations of mutations can be grown side-by-side. These large populations of organisms are genetically nearly identical, except for the specific combinations of mutations in each plant. The particular combinations that result in desirable phenotypes can be identified based on improved quality or performance in the field or greenhouse or lab testing. Combinations of mutations can generate significant phenotypes as their effects may be additive or synergistic.

In one aspect, this document features a method for identifying combination of genetic mutations that improves a phenotype of a plant. The method includes selecting a plurality of genomic targets (e.g., 4, 5, 6 or more genomic targets); making a plant cell that has both gRNAs designed to mutate the selected genomic targets and a Cas polypeptide, so that a plant descended from the plant cell will have germline mutations; sexually crossing a first parental plant comprising at least a subset of the germline mutations to a second parental plant to produce a progeny population; selecting at least one progeny plant the population as having an improved phenotype to obtain a selected progeny plant; and determining which mutations are present within the selected progeny plant, thereby identifying a combination of mutations that improves a phenotype of a plant. The method can include repeating all the steps by either selecting genomic targets determined to be mutated in the selected progeny, using in the sexual cross a parent related by lineage to the selected progeny, or both. The plants could be corn (Zea mays) and the genomic targets can comprise at least one of SEQ ID NOs: 26-39. The plants could also be Sorghum (Sorghum bicolor), wheat (Triticum aestivum), or rice (Oryza sativa).

In some embodiments at least some of the different gRNAs are designed to mutate distinct residues of the same genomic target. In some embodiments at least some of the different gRNAs are designed to mutate residues within conserved sequences of paralogous genes. In some embodiments a plant cell is made by inserting gRNA-expressing transgenes. In some embodiments a plant cell is made by adding a Cas9 polypeptide-expressing transgene, which may be accomplished by crossing. In some embodiments a plant cell is made by contacting the cell with pre-assembled gRNA-Cas9 ribonucloeoproteins. In some embodiments the first parental plant is a progeny of selfing a plant with germline mutations. In some embodiments the first parental plant is a progeny of a cross of the plant having germline mutations to a wild type plant or to another plant, so that the germline mutations of the first parental plant are heterozygous. In some embodiments the first parental plant does not have a Cas9 polypeptide-expressing transgene. In some embodiments in the second plant also has germline mutations. In some embodiments the first and second parental plants are isogenic and belong to complementary heterotic groups. In some embodiments the first parental plant or the second parental plant is cytoplasmically male sterile.

Selecting at least one individual with an improved phenotype from the progeny population may be based at least in part on performance of the plant under field testing conditions. The selection may also be based at least in part on other criteria such as the selected plant's water use efficiency, nitrogen use efficiency, seed oil content, or plant density stress performance. In some embodiments, the progeny population from which an individual is selected may be itself be selected by genotyping, for example by seed chipping. A collection of seeds can be made with embryonic cells having a combination of genetic mutations identified according to the methods described.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWING

FIG. 1: Progenitor plants have multiple gRNA-expressing transgenes or a Cas9-expressing transgene. When crossed, the progeny combining the expression of Cas9 and gRNAs produces germline mutations of the gRNA targets. A cross with a wild type plant of a similar genetic background allows for segregation of Cas9 and gRNA transgenes, as well as making the mutations heterozygous. Crossing plants heterozygous for the mutations, here shown on the female side, with plant of a complementary heterotic group, results in formation of hybrids that recombine the mutated alleles. These hybrids can be phenotyped for the traits of interest to select favorable combinations of mutations.

DETAILED DESCRIPTION

This document relates to methods and materials for identifying or optimizing combinations of mutations that improve one or more phenotypic features of an organism. For example, the methods described herein can be used in plants to improve grain yield; tolerance to an abiotic stress such as drought stress, osmotic stress, or nitrogen deficiency; soil aluminum; cold stress; frost stress; density stress; heat stress; oxidative stress; low light tolerance; herbicide stress; as well as improved water use efficiency; nitrogen use efficiency; phosphate use efficiency; seed oil or protein content; lignin content; biotic or pest resistance; biomass; heterosis; chemical composition such as higher percentage of sucrose; plant architecture such as increased tillering or branching, decreased or increased apical dominance, or increased root mass; flowering time; and/or biofuel conversion properties in a plant. "Water use efficiency," "nitrogen use efficiency," or "phosphate use efficiency" refers to increased yield under the same levels of input, i.e., same level of water, nitrogen, or phosphate.

In general, the methods described herein can include obtaining first and second parental organisms, wherein at least one of the parents includes a plurality of mutations introduced by genome editing, sexually crossing the parent organisms to produce a progeny population, and identifying the combinations of mutations that improve a phenotypic feature. In some cases, one of the parental organisms can be a wild type plant. In some cases, each parent can be mutated and can include one or more mutations. As described in more detail below, the first and/or second parental organisms can be heterozygous for the mutations, and the gametes of one or both parental organism can include independently segregating subgroups of the plurality of mutations.

Mutations are generated in selected genomic targets of an organism (e.g. a crop plant) by genome editing using a CRISPR/Cas system. Accordingly, a guide RNA (gRNA) that is directed to a residue of the genomic target and a Cas endonuclease must be simultaneously present in the same cell as the a genomic target to be mutated. The gRNA binds the endonuclease and guides it to the genomic target at the location where it is complementary to the engineered gRNA sequence. After the endonuclease cleaves the genomic target, many types of mutations (e.g. insertions, deletions, substitutions) around the nucleic acid residues of the target of the respective gRNA will be formed, often by the error-prone Non-Homologous End Joining (NHEJ) pathway. Consequently, the same gRNA/Cas can act to make multiple mutations, and different mutations can produce different phenotypes.

In some embodiments, as depicted in FIG. 1, gRNAs and Cas endonucleases are produced by the expression of transgenes. Consequently, Cas expression can be maintained in a separate plant from the one or many gRNA-expressing transgenes, as needed for carrying out the present methods. Then, Cas can be brought together with selected gRNAs by crossing two parents having these transgenes, as long as their co-expression will occur at least in germline cells. In this illustrated progeny, Cas and gRNA-expressing transgenes are hemizygous, and their simultaneous expression of both gRNAs and Cas molecules generates mutations. But individual progeny of this cross will not be uniformly mutated, since the same gRNA can generate different mutations. The progeny population may be useful at this point to identify combinations of mutants with improved phenotypes, especially if co-expression occurs early in development such as in the fertilized egg or the embryo. In some cases, however, it is desirable to segregate at least the Cas transgene so as to both avoid additional mutations and form different combinations of the mutations. This can be accomplished with a different cross, illustrated with a wild type (wt) parent in FIG. 1. The progeny of this second cross will have the mutations in a heterozygous state. Consequently, a cross of this progeny with another plant will result in recombination of all the mutations, and the progeny will be a population having different segregating mutations. This population, noted as F1 in FIG. 1, can be phenotyped for identifying outstanding pairs or combinations of mutations.

The methods described herein provide a number of advantages when compared to alternative solutions, although not all advantages may be present in a specific embodiment.

For most breeding objectives, commercial breeders work within germplasm that is often referred to as the cultivated type. This germplasm is easier to breed with because it generally performs well when evaluated for agronomic performance. The performance advantage the cultivated type provides is sometimes offset by a lack of allelic diversity. This is the tradeoff a breeder accepts when working with cultivated germplasm: better overall performance, but a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs. In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, *Proc. Am. Soc. Hort. Sci.* 44:413-16). In this cross, a nematode disease resistance was transferred from *L. peruvianum* into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked.

Some phenotypes are determined by the genotype at one locus. These simple traits, like those studied by Gregor Mendel, fall in discontinuous categories such as green or yellow seeds. Most variation observed in nature, however, is continuous, like yield in field corn, or human blood pressure. Unlike simply inherited traits, continuous variation can be the result of polygenic inheritance. Loci that affect continuous variation are referred to as quantitative trait loci (QTLs). Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability agronomic traits because these cultivars will allow growers to produce a crop with uniform market specifications.

Consequently, mutations conferring improved agronomic traits are a powerful tool in the development of new and improved cultivars. Mutations are defined genetic alterations that do not require segregation from linked regions in order to avoid genetic drag. And again due to their genetic nature, contributions of mutations to a defined trait have high heritability. As explained in more detail below, however, the precise impact of a mutation or combination of mutations needs to be experimentally measured to understand the extent to which it depends on the relevant QTLs present in the germplasm in which they are tested. Understanding any QTL-dependent mutation impact is helpful, for instance, in cases where a mutation has a phenotypic effect in a heterotic genetic background that is significantly different in magnitude from the corresponding effect in plants with inbred depression.

Exploring the phenotypic effect of many stacked mutations, rather than single mutations, is more likely to result in finding mutations resulting in significant yield or quality improvements. The genome of cultivated plants, for example, comprises a background system of complex molecular interactions. For a mutation to boost a trait its products need to fit into the complex, regulated downstream networks appropriately. If the genetic background changes then the effect of the mutation may change too. For this reason specific mutations sometimes fail to achieve the desired effect in all genetic backgrounds and environments. A change to a single component of a very complex system is unlikely to have a dramatic positive effect; several distinct alterations, on the other hand, as with a stack of mutations, are more likely to result in an enhanced or synergistic positive effect, and/or diminished negative features of a mutation-caused pleiotropic phenotype.

The methods described herein make it possible to produce and test in parallel a high number of mutations in different combinations. Any phenotypic feature could be affected by a large number of candidate mutations, and a much larger number of combinations or stacks mutations. But the phenotype of individual combinations, which may or may not turn out to be additive or even synergistic when compared to the phenotype of single mutations, is generally unpredictable, so testing a large number of combinations is necessary. Hence, the high-throughput methods described herein are useful for quickly sorting through large numbers and identifying the combinations of mutations that improve one or more phenotypic features. In other words, existing methods, such as random mutagenesis, would produce too rarely similar combinations as made possible by the methods presented here, and these combinations would be difficult to sort out as their effect would be entangled with the deleterious effects of other combinations. It is worth noting that while unpredictability of produced mutations with some CRISPR/Cas mutagenesis systems can actually be problematic for their application in other technological areas, it is actually advantageous for the methods presently described.

Generating new mutations, such as by random mutagenesis with mutagens or by wide crosses, while routinely accomplishable, is also a process that by its nature adds challenges to studying comparative performance of plants. This is because multiple unrelated mutations accumulate and generally create a range of mutant phenotypes in independently selected plants. Mutations causing genetic drag need to be segregated first to understand the potential impact of individual mutations or their combinations. Hence, compared to use of random mutagenesis, the procedures described here often require a limited number of backcrosses, if any, which cuts down on the amount of labor necessary to make and characterize the materials, but more importantly provide results such that the relative performance of combined mutations can be reliably scored. Moreover, mutations or combinations are "recyclable", i.e. once made and characterized they are likely to find use in multiple seasons and experimental setups. For example, interesting mutations only need to be made once, and then they can be used repeatedly in combination with many other different mutations, and may need to be introgressed only once into any parental germplasm of interest. This feature is especially convenient for testing in elite germplasm because of the added effort sometimes required to introgress any mutation into a uniform and commercially relevant genetic background. In some aspects, the methods presented here maintain the benefits of random mutagenesis without the drawbacks. They enable testing in elite backgrounds of large number of combinations of only the most likely yield and quality impact candidate mutations. Since the impact of mutations can be dependent on the genetic background, testing in directly elite backgrounds is advantageous, by eliminating from consideration mutations of diminished impact in elite materials. Phenotyping of candidates is also convenient because of the uniform genetic background of the siblings that make up testing populations, which can be planted in proximity so that improved phenotypes can be easily scored.

In many cases, testing populations are made based on isogenic backgrounds so as to eliminate background genetic noise that would otherwise confound data interpretation. But in other cases, especially when the effect of a limited number of combined mutations is to be understood, the genetic background may be intentionally diverse. For example, a promising stack of mutations could be observed for performance in a segregating F2 population and subsequent generations, thus allowing selection and production of parents capable to perform especially well in the presence of a specific combination of mutations.

Using the presented methods, a phenotypic measurement can be the yield of harvestable material under typical field cultivation conditions, i.e. without an intentionally applied selection pressure. This data is certainly relevant from a product performance perspective, for identifying undesirable interactions of stacked mutations, and when stacking mutations affecting different traits that cannot be revealed by a single assay. But in addition, while some mutations or stacks provide a survival or yield advantage under high selection pressure, they are known to otherwise have a negative impact when grown under typical cultivation conditions. Moreover, the populations of plants produced by the present methods are well-suited for comparative studies of related combinations. When testing side-by-side sibling plants that are otherwise genetically uniform but differ only with regard to having distinct combinations of a limited original pool of mutations, stacks of outstanding phenotypic impact can be readily identified. In some embodiments, populations produced according to the methods provided herein can be tested for field performance similarly to screening of segregating populations by plant breeders. This way, the effect of high numbers of combined mutations can be simultaneously observed, often in a commercially relevant, elite genetic background, which may be made up of defined heterotic groups and/or QTLs for specific traits, and so well-performing mutants that surpass commercially relevant thresholds can be more easily identified. By using the methods described herein, useful combinations of mutations become self-revealing, circumventing the general unpredictability of the phenotype of stacked mutations.

Genomic Targets

Genomic targets for mutation are contiguous chromosomal DNA regions generally encoding expressed sequences. Most often they are genes comprising a transcribed sequence which typically comprises a polypeptide-encoding sequence, and regulatory regions. Regulatory region refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

Selection of genomic targets for mutation can be done rationally rather than randomly. For example, based on existing data, the targets can be known or inferred as likely to affect a trait, such as morphological development of a plant part that may increase yield or environmental stress resistance. The types of data useful in identifying genomic targets is dependent on the phenotype to be improved, but it may be from the location of quantitative trait loci (QTL), transgenic phenotypes caused by overexpression of sequences, participation in relevant signaling or metabolic pathways, involvement in relevant physiological process, or phenotypes of characterized mutations.

Genomic targets can be selected based on data from different species if needed, as functional homologs of a locus. Accordingly, one or more genomic targets in a species of interest can often be identified by sequence similarity to sequences in other species for which pertinent data exists. In addition to sequence similarity, conserved domains as defined by Pfam descriptions, synteny, and/or reciprocal BLAST results may be used in identifying suitable genomic targets. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. The term "functional homolog" is sometimes applied to the nucleic acid or gene that contains a functionally homologous polypeptide.

Functional homologs can be identified by analysis of nucleotide and polypeptide sequence alignments. For example, performing a query on a database of nucleotide or polypeptide sequences can identify homologs of interest as a genomic target. Sequence analysis can involve BLAST, Reciprocal BLAST, or PSI-BLAST analysis of nonredundant databases using a reference sequence of defined interest. Amino acid sequence is, in some instances, deduced from the nucleotide sequence. Those polypeptides in the database that have greater than 40% sequence identity are candidates for further evaluation for suitability as genomic targets. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in genomic targets, e.g., conserved functional domains.

Conserved regions can be identified by locating a region within the primary amino acid sequence of a genomic target candidate polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Once a genomic target is selected, it typically contains many distinct residues that may be mutated by genome editing techniques. Creating mutations of a genomic target at many residues is desirable so as to generate essentially all the potential phenotypes from that target. The mutations are introduced generally 3-4 residues upstream of the Protospacer Adjacent Motif (PAM), which is for example 5'NGG3' for the *Streptococcus pyogenes* Cas9. Consequently, any PAM sequence on either strand of the genomic target can be used in guiding an adjacent mutation. The residue to be mutated is often part of a polypeptide-coding region, although it could also be part of an intron or regulatory region. Mutating distinct residues of the same genomic target may be accomplished by introducing double or multiple mutations into the target with different gRNAs directed to mutate different residues, or by introducing single distinct individual mutations in different progenitor cells.

The phenotypes caused by individual mutations can range from indistinguishable from wild type to a most severe knockout effects. More rarely, gain of function mutations are observed. Phenotypes result from changes in function caused by the mutations. Depending on the nature of the target, many changes do not entirely obliterate (i.e. knockout) the function of the underlying wild type target, but may alter its expression level, its encoded polypeptide's affinity for substrate or for a protein complex to which it belongs, the cellular localization of an expression product, and/or its regulation in response to stimuli affecting its regulatory network. Mutations introduced close to the 5' terminus of a coding sequence are more likely to result in knockout phenotypes than mutations close to the 3' terminus. Consequently, when multiple distinct residues of a genomic target are selected, it is often desirable to select residues proximal to the 5' terminus and to the 3' terminus of the coding sequence.

In some cases, mutations can be directed to residues in conserved regions, so as to simultaneously mutate not only the main selected genomic target, but also paralogous genes sharing the conserved region. This approach can be fruitful, for example, if paralogous genes can substitute for each other to some extent. Alternatively, mutations can be directed to residues in unique regions to avoid mutating any paralogous genes.

Many genomic targets can be selected for mutation and testing. In general, it is useful to test all the different combinations of at least four targets simultaneously. But the number of targets in a development program can be much larger, i.e. 10, 15, 20, or 25 or more targets can be mutated at various residues and their combined phenotypic effect investigated. The choice of the multiple targets to be combined can be at least in part random, so as to enable observations of synergies between different phenotypes that might not be predictable. But, the combination of targets can also be at least in part non-random, so as to enhance the likelihood that the combined mutations would interact with each other and thus produce a new phenotype when combined. For example, many different targets can be selected based on their likelihood to produce a salt tolerant phenotype. Many mutations can be produced in each target, and different mutations of the targets can be recombined to identify those pairs or combinations that complement each other so as to perform exceptionally well on salt tolerance assays.

A gRNA can target one or more genes encoding a polypeptide necessary for elaboration of cell wall polysaccharides. Non-limiting examples of polypeptides necessary for elaboration of cell wall polysaccharides include polypeptides that function in the lignin pathway (e.g., phenylalanine ammonia-lyase (PAL), cinnamate 4-hydroxylase (C4H), 4-coumarate:coa ligase (4CL), p-coumarate 3-hydroxylase (C3H), p-hydroxycinnamoylcoa: quinate/shikimate p-hydroxycinnamoyltransferase (HCT), caffeoyl-coa omethyltransferase (CCOAOMT), cinnamoyl-coa reductase (CCR), ferulate 5-hydroxylase (F5H), caffeic acid o-methyltransferase (COMT), and cinnamyl alcohol dehydrogenase (CAD), and polypeptides that function in cellulose synthase. A gRNA can target one or more genes encoding polypeptides involved in hormone biosynthesis (e.g., repressors and/or critical enzymes). For example, reducing or eliminating the function of a repressor of a hormone biosynthesis pathway can be effective to increase hormone levels. In some cases, a repressor of a hormone biosynthesis pathway can be a corepressor. For example, reducing or eliminating the function of a polypeptide that brings about critical steps in hormone biosynthesis can be effective to decrease hormone levels. Non-limiting examples of polypeptides involved in hormone biosynthesis include polypeptides involved the gibberellin (GA) pathway, the brassinosteroids (BR) pathway, the indole-3-acetic acid (IAA) pathway, the jasmonic acid (JA) pathway, the abscisic acid (ABA) pathway, the salicylic acid (SA) pathway, the cytokinin pathway, and the ethylene pathway. Exemplary targets of the GA pathway include, for example, GA20-oxidase, GA3-oxidase, GA2-oxidase, gibberellin insensitive dwarf (GID), and other polypeptides described in, for example, Park et al. (WO2013/086499, published Jun. 13, 2013). For example, reduction or elimination of a repressor of the GA pathway (e.g., GA2-oxidase) can be effective to activate the GA response. For example, reduction or elimination of an activator of the GA pathway (e.g., GA20-oxidase) can be effective to repress the GA response. In some embodiments, a gRNA can be designed to target a combination of one or more repressors and/or co-repressors of a hormone biosynthesis pathway and one or more polypeptides that bring about critical steps in hormone biosynthesis. A gRNA can target one or more genes encoding a polypeptide that represses cell division (e.g., cell cycle regulators). Non-limiting examples of polypeptides that repress cell division include cyclins (e.g., *Arabidopsis* $CDCl_2aAt$, $CDCl_2bAt$, CYCB1; 1, and alfalfa $CDCl_2fM$ and CYCB2; 2, and their homologs in other species) and cyclin-dependent kinase (CDKs).

One or more gRNA-expressing transgenes can be used to reduce or eliminate function of a gene (e.g. an endogenous gene) in a manner that enhances biocontainment (e.g., prevent outflow of the transgene into nature). Non-limiting examples of genes that can be targeted with a gRNA include, genes encoding polypeptides causing sterility (e.g., polypeptide involved in seed development), genes encoding herbicide tolerance polypeptides, genes encoding pesticide tolerance (e.g., insect resistance) polypeptides, transgenes encoding polypeptides providing agronomic traits, and transgenes encoding polypeptides involved in cell wall conversion and digestion. A gRNA can target one or more genes encoding a polypeptide causing sterility. For example, a polypeptide causing sterility can be a polypeptide involved in seed development. Non-limiting examples of polypeptides involved in seed development include FIE, AP2, INO, ANT, the polypeptide encoded by the LEC2 gene, and HAP3-type CCAAT-box binding factor (CBF) subunit.

A gRNA can target one or more genes encoding an herbicide tolerance polypeptide. Herbicide tolerance is also sometimes referred to as herbicide resistance. Non-limiting examples of herbicide tolerance polypeptides include a polypeptide encoded by a polypeptide encoded by a phosphinothricin acetyl transferase (PAT) gene, a bialaphos resistance (BAR) gene, 5-enolpyruvyl-3-phosphoshikimate synthase (EPSPS), acetolactate synthase (ALS), acetyl coenzyme A carboxylase (ACCase), dicamba mono-oxygenase (DMO), aryloxyalkanoate dioxygenase-12 (aad-12), and 4-hydroxyphenylpyruvate dioxygenase (HPPD).

A gRNA can target one or more genes encoding a pesticide tolerance polypeptide. For example, a pesticide tolerance polypeptide can be an insect resistance polypeptide. Nonlimiting examples of pesticide tolerance polypeptides include Cry1Ab, Cry1Ac, Cry1A.105, Cry1F, Cry2Ab, Cry3Bb1, Cry34Ab1, Cry35Ab1, mCry3A, and VIP3.

A gRNA can target one or more genes encoding a polypeptide conferring a desirable trait. For example, a desirable trait can be an agronomic trait. Non-limiting examples of agronomic traits include increased yield, drought tolerance, cold tolerance, tolerance to environmental stresses, enhanced nitrogen use, and male sterility. Other desirable traits can include, for example, pathogen (e.g., virus, fungus, bacterium, and/or nematode) resistance, and product quality traits (e.g., delayed fruit ripening, altered amino acid profile, altered oil profile, modified seed storage proteins, enhanced floral characteristics for ornamentals, 5 increased solids in fruit).

Seq id nos 6-10 and 25-39 provide some examples of genomic targets that may be selected and either mutated in their respective species or first used to identify similar genomic targets in other species of interest.

gRNAs

Aspects of some embodiments relate to a transgenic plant (e.g., a parent plant or a progeny plant) that includes to at least one nucleic acid having a promoter operably linked to a gRNA sequence. "Operably linked" refers to the positioning of a regulatory region and a sequence to be transcribed in a nucleic acid so that the regulatory region is effective for regulating transcription of the sequence. Expressed gRNAs can target particular nucleic acid sequences (e.g., an endogenous gene) at which a Cas enzyme can induce a double stranded break. A gRNA can include a gRNA scaffold sequence and a gRNA targeting sequence, and can be designed to target a nucleic acid sequence within the genetic material of a plant (including the nuclear chromosomes, transgenic, choroloplastic, or mitochondrial sequences). A gRNA scaffold sequence can bind a Cas enzyme (e.g., Cas9) thus guiding the Cas enzyme to a target site at which a double stranded break is desired. See, e.g., Ran et al. (2013 Nat Protoc. 8(11):2281-2308). A gRNA targeting sequence can be a nucleic acid sequence that can hybridize to a target sequence within the genetic material of a plant (e.g., a gene within a plant). In some cases, a gRNA targeting sequence can hybridize to a coding or a noncoding strand of a target gene; thus, a gRNA targeting sequence can include a portion of a genomic target sequence or complementary to a portion of a genomic target. Hybridization refers to a reaction in which two single stranded nucleic acid molecules or regions of molecules form a complex that is stabilized via hydrogen bonding between complementary bases of the nucleotide residues. A gRNA targeting sequence that hybridizes to a genomic target can be of any appropriate length that is sufficient to promote hybridization, a double stranded break, and double stranded break repair (e.g., nonhomologous end joining) at the desired site. In some cases, the gRNA targeting sequence can include a portion of a genomic target or the full length of a genomic target. A gRNA targeting sequence can be from about 5 to about 45 nucleotides in length (e.g., from about 5 to about 45, from about 8 to about 40, from about 10 to about 35, from about 13 to about 30, from about 15 to about 27, from about 17 to about 25, from about 18 to about 24, or from about 19 to about 23 nucleotides in length). For example, the gRNA targeting sequence can be at least 5, at least 8, at least 10, at least 13, at least 15, at least 17, at least 18, at least 19, or at least 20 nucleotides in length. For example, the gRNA targeting sequence can be no greater than 45, no greater than 40, no greater than 35, no greater than 30, no greater than 27, or no greater than 25 nucleotides in length. In some cases, the gRNA targeting sequence includes 20 nucleotides. The amount of sequence identity shared by a gRNA targeting sequence and a desired site in a genomic target can vary. For example, the amount of sequence identity can be at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 30 96%, 97%, 98%, 99% or 100% sequence identity. Methods for determining hybridization conditions (including complementarity and percent sequence identity) that can used as described herein include, without limitation, those are described elsewhere (e.g., Sambrook et al. *Molecular Cloning: A Laboratory Manual,* 2nd ed., Cold Spring Harbor Laboratory Press, 1989; and Ausubel et al., *Current Protocols In Molecular Biology,* John Wiley & Sons, New York, 1987).

In some cases, the methods and materials provided herein (e.g., vectors) can include using multiple gRNAs directed to at least one target residue site within a gene (e.g., an endogenous gene) to reduce or eliminate function of the target gene upon mutagenesis. In some cases, a nucleic acid molecule can have at least one promoter operably linked to one gRNA-expressing sequence (e.g., one, two, three, four, five, six, seven, eight, nine, ten, eleven, twelve, or more gRNA-expressing sequences). In some cases, a nucleic acid molecule can have five gRNA-expressing transgenes. Multiple (e.g., two or more) gRNA-expressing transgenes provided herein can be directed to a single genomic target or can be designed to target multiple (e.g., two or more) genomic targets. In embodiments where multiple gRNA-expressing transgenes are directed to a single target gene, the gRNA-expressing transgenes can be directed to the same site within the genomic target, or the gRNA-expressing transgenes can be directed to different sites within the genomic target. In embodiments where multiple gRNA-expressing transgenes are directed to multiple genomic targets, the gRNA-expressing transgenes can each be directed to an independent genomic target.

Multiple (e.g., two or more) gRNAs directed to at least one target site within a gene (e.g. an endogenous gene) can be provided via a single nucleic acid molecule (e.g., in tandem expression cassettes) or can be provided via multiple nucleic acid molecules (e.g. on more than one expression cassette). In some cases, a nucleic acid molecule can have five gRNA-expressing transgenes provided via tandem expression cassettes. One or more gRNA-expressing transgenes provided herein can be used to reduce or eliminate function of a gene (e.g. an endogenous gene) in a manner that improves plant health (e.g., to provide desirable agronomic traits). Non-limiting examples of genomic targets that can be altered with a gRNA include genes necessary for elaboration of cell wall polysaccharides, genes that are repressors or co-repressors of hormone biosynthesis pathways, genes that bring about critical steps in hormone biosynthesis, and genes that repress cell division.

Nucleic Acid Molecules

In some embodiments, a transgenic plant can be a parent plant including a nucleic acid molecule having a first promoter operably linked to at least one transgene. For example, a parent plant can include a nucleic acid molecule having a promoter (e.g., a ubiquitously expressing promoter, which may direct transcription by Pol III, such as the corn U6 (SEQ ID NO: 3) or *Sorghum* U3 (SEQ ID NO: 4) promoters) operably linked to at least one gRNA-sequence to be expressed, and a parent plant can include a second nucleic acid molecule having a second promoter (e.g. expressing at least in germline cells) operably linked to a Cas-encoding sequence. It is typically desired, but not always necessary, that the at least one transgene does not itself cause any phenotype in the parent plant, for example via insertional effects. Expression of both a gRNA and a Cas allows for the formation of a gRNA/Cas complex capable of introducing a double strand break in a target site within a genome (e.g., within a gene). The double stranded break can lead to introduction of at least one mutation in a genomic target such that the mutation confers a modified function of that genomic target. As mutations occur in germlines, progeny plants inherit the modified function of the target gene.

A promoter refers to a nucleic acid capable of driving expression of another nucleic acid (e.g., a coding nucleic acid). A promoter is operably linked to another nucleic acid when it is capable of driving expression of that nucleic acid fragment. The choice of promoter to be included in a nucleic acid molecule described herein depends upon several factors, including, but not limited to, efficiency, selectability, inducibility, desired expression level, and cell- or tissue-preferential expression. In different embodiments, the Cas-encoding sequence can be placed under the control of any of a number of promoters that are capable of directing expression in at least some progenitor cells of germline tissues, so that egg and pollen cells comprise the mutations.

Preparation of the nucleic acids disclosed herein can be accomplished using techniques in molecular biology, biochemistry, chromatin structure and analysis, computational chemistry, cell culture, recombinant DNA, and related fields. These techniques are described, for example, in Sambrook et al. Molecular Cloning: A Laboratory Manual, 2nd ed., Cold Spring Harbor Laboratory Press, 1989; and in Ausubel et al., Current Protocols In Molecular Biology, John Wiley & Sons, New York, 1987.

CRISPR-Associated (Cas) Genes

CRISPR/Cas systems are known in the art and can be engineered for directed genome editing. Cas genes encode RNA-guided DNA endonuclease enzymes capable of introducing a double strand break in a double helical nucleic acid sequence. Nucleases engineered to introduce single strand breaks can also be suitably adapted for use with the present invention. The Cas enzyme can be directed to make the double stranded break at a target site within a gene using a guide RNA. A Cas enzyme can be guided by a guide polynucleotide (e.g., a guide RNA) to recognize and introduce a sequence-specific double strand break at a site determined by the guide polynucleotide. A Cas enzyme can be from any appropriate species (e.g., an archaea or bacterial species). For example, a Cas enzyme can be from *Streptococcus pyogenes, Pseudomonas aeruginosa*, or *Escherichia coli*. In some cases, a Cas enzyme can be a type I (e.g., type IA, IB, IC, ID, IE, or IF), type II (e.g., IIA, IIB, or IIC), or type III (e.g., IIIA or IIIB) Cas enzyme. The encoded Cas enzyme can be any appropriate homolog or Cas fragment in which the enzymatic function (i.e., the ability to introduce a sequence-specific strand breaks in a double helical nucleic acid sequence) is retained. In some cases, a Cas enzyme can be codon optimized for expression in particular cells, such as dicot or monocot plant cells. See, for example, the CRISPR/Cas profiles database available on the National Center for Biotechnology Information website (available at ncbi.nih.gov/pub/wolf/_suppl/CRISPRclass/crispr-Pro.html). In some embodiments, a Cas gene is from *Streptococcus pyogenes*. Examples of Cas genes that can be used as described herein include, without limitation, Cas3, Cas4, Cas6, Cas8a, Cas8b, Cas8c, Cas9, Cas10, Cas10d, Cmr5, Cpf1 (Zetsche et al., 2015 "Cpf1 Is a Single RNA Guided Endonuclease of a Class 2 CRISPR-Cas System" Cell 163, 759-771), Cse1, Csm2, Csn2, and Csy1 genes. In some embodiments, a Cas gene is a *Streptococcus pyogenes* Cas9 gene (SEQ ID NO: 1).

Any appropriate CRISPR/Cas system can be used as described herein. Examples of CRISPR/Cas systems that can used as described herein include, without limitation, those are described elsewhere (e.g. U.S. Pat. Nos. 8,697,359; 8,771,945; 8,795,965; 8,865,406; 108,871,445; 8,889,356; 8,889,418; 8,895,308; 8,906,616; 8,932,814; 8,945,839; 8,993,233; 8,999,641; 9,115,348; U.S. Pat. App. Pub. Nos. 2011/0223638; 2014/0068797; 2014/0302563; 2014/0315985; 2015/0152398; 2015/0284697; and Schaeffer et al. 2015 Plant Sci. 240:130-42).

Additional features that can be used to control and/or enhance the CRISPR/Cas system include, for example, protospacer adjacent motifs, spacers (e.g., target spacers), and termination signals (see, e.g., Mali et al., 2013 *Science* 339:823-826). A gRNA-expressing transgene can include a protospacer adjacent motif (PAM) sequence. Without being bound by theory, it is believed that PAMs to be important for type I (e.g., type IA, IB, IC, ID, IE, or IF) and type II (e.g., IIA, IIB, or IIC) CRISPR-Cas systems, but are not necessary in type III (e.g., IIIA or IIIB) CRISPR-Cas systems. For example, it is believed that a type I or type II Cas enzyme will recognize and cleave a gene sequence having a PAM sequence at the 3'-end. A PAM sequence can be on a coding strand or a noncoding strand of a target gene. A PAM sequence on a coding strand can be, for example, 5'-NGG-3' where N is any nucleotide followed by two guanine (G) nucleotides or 5'-NGA-3' where N is any nucleotide followed by a guanine (G) residue and an adenine (A) residue. A PAM sequence on a non-coding strand can be, for example, 5'-CCN-3' where N is any nucleotide following two cysteine (C) residues. A nucleic acid molecule having a gRNA expressing transgene as described herein can also include at least one target spacer. Thus, a target spacer corresponding to a sequence upstream of a PAM can be used to ensure binding of a gRNA to a target site within a gene and enable Cas enzyme activity at a nearby cleavage site within the gene.

Transgenic Plants and Methods of Making Transgenic Plants

In some embodiments this document relates to transgenic plants having at least one nucleic acid molecule described herein (e.g., having a promoter operably linked to at least one sequence to be transcribed). As used herein, a transgenic "plant" can constitute part or all of a whole plant. For example, a plant can include plant cells, explants, seed, plants grown from said seed, and grain having at least one nucleic acid molecule described herein. A transgenic plant also refers to progeny of an initial transgenic plant provided the progeny inherits a nucleic acid molecule described herein.

Transgenic Plants

A transgenic plant provided herein can be a parent plant including a nucleic acid molecule having a first promoter operably linked to at least one transgene. A parent plant can include any combination of promoters and transgenes described herein. For example, a first parent plant provided herein can include a first nucleic acid molecule having a first promoter operably linked to a first sequence, a second parent plant provided herein can include a second nucleic acid molecule having a second promoter operably linked to a second sequence, and so on. Preferably, expression of a first or a second transgene in a parent plant does not cause any phenotype in a parent plant. As such, a parent plant can be chosen based on the absence of any phenotype resulting from expression of the transgene. A first parent plant can include a first nucleic acid molecule as described herein. For example, a first parent plant can include a first nucleic acid molecule having a first promoter operably linked to at least one first transgene. The first promoter can be a ubiquitous promoter (e.g. a Pol III promoter). The first transgene can be a gRNA-expressing transgene.

A second parent plant can include a second nucleic acid molecule as described herein. For example, a second parent plant can include a second nucleic acid molecule having a second promoter operably linked to a second transgene. The second promoter can be a regulated promoter (e.g., a tissue-specific promoter or a developmentally-specific promoter), or a ubiquitously expressing promoter. The second transgene can be a Cas-expressing transgene. In some embodiments, a second parent plant can include a second nucleic acid molecule having a developmentally-specific floral meristem Zm Zap1 promoter (SEQ ID NO: 5) operably linked to at least one Cas9-encoding sequence (SEQ ID NO: 1). Expression of at least one Cas9-e encoding sequence in, for example, the floral meristems of the second parent plant may produce germline cells harboring different mutations, and thus a single plant can give rise to progeny with different mutations in the same genomic target. But in general, mutations can be kept in germ cells by Cas and gRNA co-expression in cellular progenitors, thus ensuring that the mutations become heritable. Accordingly, co-expression of the gRNA-expressing transgene and a Cas expressing transgene can be designed to occur so as to edit the cells of the gametophytes, the generative or sperms cells in the pollen, or the megaspore mother cell or the egg cell in the embryo sac, or the zygote.

A transgenic plant can also be a progeny resulting from a cross between a first parent plant and parent plant as described herein. Progeny include descendants of a particular plant or plant line. Progeny of an instant plant include seed formed on F1, F2, F3, and subsequent generation plants, seeds formed on BC1, BC2, BC3, and subsequent generation plants, or seeds formed on F1BC1, F1BC2, F1BC3, and subsequent generation plants. Seed produced by a transgenic plant can be grown and then selfed (or outcrossed and selfed) to obtain seed homozygous for a mutation or transgene of interest. Progeny can include transgenic seed produced by crossing a first parent plant and second parent plant as described herein as well as transgenic plants grown from those transgenic seed.

Methods for Making Transgenic Plants

Nucleic acid molecules as described herein can be introduced into a plant or plant cell by any appropriate means in order to establish a transgenic plant. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be used in the methods described herein.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass composition-modulating polypeptide whose expression has not previously been confirmed in particular recipient cells.

Techniques for introducing nucleic acid molecules into monocotyledonous and dicotyledonous plants are known in the art, and include, without limitation, *Agrobacterium* mediated transformation, viral vector-mediated transformation, electroporation and particle gun transformation, e.g., U.S. Pat. Nos. 5,538,880; 5,204,253; 5,591,616; 6,013,863; and 6,329,571. If a cell or tissue culture is used as the recipient tissue for transformation, plants can be regenerated from transformed cultures by techniques known to those skilled in the art.

Growing Transgenic Plants

Transgenic plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

It is often convenient to maintain Cas transgenes and gRNA transgenes in different parents, and then produce mutations by crossing the parents to obtain mutated seeds. gRNA-expressing transgenes can be stacked as needed. Then, crosses to the Cas transgene parents result in mutated progeny.

Mutations by Transient Transfection

In some embodiments the methods can be practiced at least in part without transgene expression. Accordingly, tissue culture materials such as protoplasts can be transfected with pre-assembled ribonucloeoproteins complexes of purified Cas and gRNA (see Woo et al., Nature Biotechnology 2015, 33: 1162-1165). Plants regenerated from tissue culture often comprise the intended mutations. gRNAs can be mixed in different combinations before transfection to produce candidates that combine the designed mutations as desirable. This technique can be especially useful in species where sexual crossing is difficult or impossible, as for *Miscanthus* x *giganteus* or *Saccharum officianarum*. pre-assembled gRNA-Cas9 ribonucloeoproteins.

Species

The methods described herein can be applied to organisms capable of genetic modification and sexual recombination. For example, the methods described herein can be applied to plants (e.g., plant species of importance to agriculture), fungi (e.g., yeast), protozoans, and animals (e.g., fish such as salmon or zebra fish, fruit flies, or earthworms). In some cases, the methods described herein can be applied to monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

For example, suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea*. In some embodiments, suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), Triticosecale (*triticum*—wheat X rye) or bamboo.

Additional examples of suitable species include *Helianthus annuus* (sunflower), *Carthamus tinctorius* (safflower), *Jatropha curcas* (*Jatropha*), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver sommferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanaceturn parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum,* or hybrids thereof (e.g., *Pennisetum purpureum* x *Pennisetum typhoidum*).

In some embodiments, a suitable species can be a wild, weedy, or cultivated *Miscanthus* species and/or variety such as, but not limited to, *Miscanthus* x *giganteus, Miscanthus sinensis, Miscanthus* x *ogiformis, Miscanthus floridulus, Miscanthus transmorrisonensis, Miscanthus oligostachyus, Miscanthus nepalensis, Miscanthus sacchariflorus, Miscanthus* x *giganteus* 'Amuri', *Miscanthus* x *giganteus* 'Nagara', *Miscanthus* x *giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Pat. No. 14,743), *Miscanthus* var. 'Gold Bar' (U.S. Pat. No. 15,193), *Miscanthus* var. 'Gracillimus', *Miscanthus* var. 'Graziella', *Miscanthus* var. 'Grosse Fontaine', *Miscanthus* var. 'Hinjo aka Little Nicky' ™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Pat. No. 13,008), *Miscanthus* var. 'Lottum', *Miscanthus* var. 'Malepartus', *Miscanthus* var. 'Morning Light', *Miscanthus* var. 'Mysterious Maiden' (U.S. Pat. No. 16,176), *Miscanthus* var. 'Nippon', *Miscanthus* var. 'November Sunset', *Miscanthus* var. 'Parachute',

*Miscanthus* var. 'Positano', *Miscanthus* var. 'Puenktchen' (ala 'Little Dot'), *Miscanthus* var. 'Rigoletto', *Miscanthus* var. 'Sarabande', *Miscanthus* var. 'Silberpfeil' (aka.Silver Arrow), *Miscanthus* var. 'Silverstripe', *Miscanthus* var. 'Super Stripe' (U.S. Pat. No. 18,161), *Miscanthus* var. 'Strictus', or *Miscanthus* var. 'Zebrinus'.

In some embodiments, a suitable species can be a wild, weedy, or cultivated *Sorghum* species and/or variety such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum* x *almum, Sorghum* x sudangrass or *Sorghum* x *drummondii*.

Thus, the methods described herein can be applied to a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (*Sorghum*, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the methods described herein can be applied to hybrids of different species or varieties of a specific species (e.g., *Saccharum* sp. X *Miscanthus* sp., *Sorghum* sp. X *Miscanthus* sp., e.g., *Panicum virgatum* x *Panicum amarum, Panicum virgatum* x *Panicum amarulum*, and *Pennisetum purpureum* x *Pennisetum typhoidum*).

An elite plant line or elite plant variety can be an agronomically superior plant line that has resulted from many cycles of breeding and selection for superior agronomic performance. Generally, an elite variety is a collection of plants that has been selected for a particular characteristic or combination of characteristics or traits, uniform and stable in those characteristics, and when propagated by appropriate means, retains those characteristics. An elite variety may have a high uniformity level at least with respect to specific genomic regions. For example, at least 90% of the individuals of an elite variety may exhibit a specific genotypic profile, as it may be detected and characterized with the respective molecular markers. Numerous elite plant lines are available and known to those of skill in the art of breeding for any cultivated plants. Traits that may be considered to confer elitism include, without limitation, good lodging resistance, reduced bacterial infection susceptibility, good seed set, good pollen set, good roots, good cold germination, good combining ability, tolerance to pests, tolerance to disease, tolerance to drought, tolerance to salts or metals, uniform floral timing, good fertilizer use efficiency, high yield as an inbred, high yield as a hybrid, good plant height, and optionally herbicide resistance or tolerance. In some cases, an elite line or elite cultivar might not itself exhibit such traits, but rather it is considered elite because it exhibits the ability to serve as one parent of an elite hybrid.

Crossing

In some aspects, the methods described herein are based in part on segregation of heterozygous mutations in sexual crossing. The recombination step often involves crossing of two different plants, i.e., male and female, rather than self-fertilization of self-compatible plants. Typically, hybrids can be produced by preventing self-pollination of female parent plants (i.e., seed parents), and permitting pollen from male parent plants to fertilize female parent plant, and allowing F1 hybrid seeds to form on the female plants. Self-pollination of female plants can be prevented by physically emasculating the flowers at an early stage of flower development. Alternatively, pollen formation can be prevented on the female parent plants using a form of male sterility. For example, male sterility can be cytoplasmic male sterility (CMS), nuclear male sterility, genetic male sterility such as temperature or photoperiod-sensitive genetic male sterility, molecular male sterility wherein a transgene or mutation inhibits microsporogenesis and/or pollen formation, or be produced by self-incompatibility. Female parent plants containing CMS are particularly useful. Some crop species such as corn, *Sorghum*, canola, and rice have well known hybridization systems based on cytoplasmic male sterility (CMS). In embodiments in which the female parent plants are CMS, the male parent plants typically contain a fertility restorer gene to ensure that the F1 hybrids are fertile.

The parent plants can be grown as substantially homogeneous adjoining populations to facilitate natural cross-pollination from the male parent plants to the female parent plants. The F1 seed formed on the female parent plants can be selectively harvested by conventional means. One also can grow the two parent plants in bulk and harvest a blend of F1 hybrid seed formed on the female parent and seed formed upon the male parent as the result of self-pollination.

A hybridization system based on a two component design also can be adopted in species where CMS or physical emasculation options are not widely available. Accordingly, a line could be developed that is homozygous for a target transgene coding for the cytotoxic barnase sequence. A different line has an activator transgene with a DNA binding domain complementary to upstream activating sequence of the barnase target and a transcription activating domain capable of driving tanscription, and driven by an anther specific promoter. The two lines are crossed to produce the female for the cross needed to produce the testing population. The male plant for the cross which produces the testing population, on the other hand, is homozygous for a barnase-inactivating barstar sequence. The barstar transgene could be either a target transgene for a two component system, possibly with the same UAS as the barnase transgene, or could be a direct fusion gene. Of course, other transgenes or mutations would also be present in the male and female progenitors of the testing population. Alternatively, similarly to the canola MS8/RF3 hybridization system, male sterility can be achieved with a barnase sequence driven by a tapetum-specific promoter (Mariani et al., Nature 357, 384-387, 1992), which can be used in conjunction with a linked herbicide tolerance gene for female propagation. Fertility can be restored when needed by crossing with a plant having a construct directing expression of barstar sequence in the same cells as the barnase. Suitable promoters may be found in the literature, including Kato et al., 2010 Plant Mol. Biol.

Rep 28: 381-387, Luo et al., 2006 Plant Mol. Biol 62(3): 397-408, Gupta et al., 2007 Plant Cell Rep. 26(11): 1919-31, Liu et al., 2013 Planta 238(5): 845-57, and Goldberg et al., 1993 Plant Cell 5: 1217-1229.

Nevertheless, self-fertilization of a self-compatible species is also feasible to carry out the methods provided herein. Selfing of a plant with heterozygous mutations can provide by meiotic recombination needed for a testing population. Selfing of heterozygous materials may also be performed at an earlier or intermediate step of providing a testing population to produce plants with a genetic composition of heterozygous and/or homozygous mutations that may be desirable for phenotyping, producing, or propagating.

Testing Populations

A population of individuals having different combinations of mutations needs to be made, and then phenotyped. There are many ways of making a suitable testing population.

In many cases, a Cas-expressing transgene is present in one parent of a cross, and gRNA-expressing transgenes are present in the other parent. It is often desirable for the Cas-expressing transgene to be homozygous in the parent, so the entire population formed by the cross accumulates mutations. The gRNA transgenes can also be homozygous in the parent, although all or some gRNA-expressing transgenes may also be heterozygous in certain experimental designs. The heterozygous transgenes will segregate in the progeny, and thus contribute to a population comprising individuals with either wild type or mutated genomic targets.

If the Cas transgene is expressed early in development, the progeny of the very first cross between a Cas-expressing transgene parent and a gRNAs-expressing parent could itself be a testing population. This is because relatively uniform genotypes are produced throughout the tissues of such individuals, so the phenotypes observed in this population are likely to be heritable. The individuals of the population will have different sets of mutations caused by the random NHEJ repair mechanism.

In most cases, it is desirable to produce a testing population that recombines mutations first generated in progenitor individuals. One reason for this is to "shuffle" the mutations and thus increase the diversity of the testing population, thus increasing the chances of seeing phenotypes caused by specific pairs or combinations of mutations. Also, especially if a high numbers of genomic targets are addressed, it is desirable to have a testing population with individuals comprising mutations only in different subsets of genomic targets. Another reason for producing testing populations by crossing individuals with the original germline mutations is to segregate transgenes away from the testing population. A Cas-expressing transgene may be problematic if present in certain testing populations as it may produce new unintended mutations.

In most embodiments, the testing population contains mutations recombined by meiotic segregation. Thus one or both parents have at least a subset of the mutations of interest in a heterozygous state, and they give rise to progeny, i.e. a testing population, with the expected recombination of mutations. In some embodiments, each mutation in a heterozygous state will segregate during meiosis, forming gametes either containing or free of the mutation. This meiotic segregation is used in the methods provided herein, so that parental plants carrying many mutations of interest generate progeny with many different combinations of the parental mutations.

The genetic background of a testing population is in many embodiments as homogenous as possible, so as to have as little individual to individual variation as possible, as this variation would interfere with the phenotype to be scored that is attributable to individual mutation combinations. Thus, transgenes may first be introgressed, if needed, in near isogenic lines, and then the various crosses could be planned to form the testing population. A testing population, however, is often the F1 seed of parents of complementary heterotic groups, as understanding the effect of mutations within the heterotic background of a commercially relevant hybrid is desirable. Either or both parent may comprise mutations, and the mutations may be made by gRNAs that are completely identical between the parents or progenitors of the parents, completely different, partly overlapping, or with at least a subset of the initial gRNAs directed to different residues of the same genomic targets.

There are many types of crosses that can produce testing populations. In many cases, forming heterozygous individuals by crossing individuals having germline mutations to wild type is appropriate. It is desirable, however, to have a testing population with individuals homozygous for at least some mutations so as to produce phenotypes of recessive alleles. Consequently, selfing or sibling crossing is needed, or, if heterosis needs to be maintained, mutations can be generated independently or introgressed into complementary genetic backgrounds.

There are many ways in which parental plants having heterozygous mutations of interest can be obtained. For example, for self-compatible species, it is easy to make by selfing and selection a parent stock that is homozygous for the mutations of interest. Heterozygous mutations will then result by crossing homozygous plants with a plant null for the respective mutations. For self-incompatible species, fixing homozygous mutations in a propagating population is also feasible, and molecular characterization of individual progenitors would be especially helpful. Creating double haploids can also be useful, if feasible for a particular species, when needed to obtain plants homozygous for desired mutations.

In some embodiments testing populations are made by crossing parents with heterogeneous mutant makeup. Crosses may be made randomly starting with parents of diverse but known mutation mixture composition. As long as pollination occurs randomly, the genetic structure of the progeny or testing population can be inferred from the distribution of mutations in the parents. This approach may be convenient in certain cases, such as when working with obligate outcrossing species or with populations of improvement rounds.

In some embodiments, the parent plants also can be homozygous for one or more mutations. In some embodiments, the parent plants are heterozygous at loci of interest, with both alleles mutated from the genomic target wild type.

In some embodiments, mutations may be present in both the male and female parents of the cross that makes the testing population. In other embodiments, all the heterozygous mutations may be present in a single parent. This approach is desirable when transformation of one parent is comparatively easy, so that introgression of mutations into a parent of a different genetic background is not necessary.

Phenotyping

Populations of progeny plants can be screened and/or selected for those members of the population that have a trait or phenotype, or a combination of traits or phenotypes conferred by the particular combinations of mutations that is distinguishable from control plants. A control plant refers to a plant that does not contain one or more of the mutations in a plant of interest, but otherwise has the same or similar genetic background. A suitable control plant can be a non-mutant wild type plant, a non-mutant and optionally non-transgenic segregant from a mutagenesis experiment, a plant that contains one or more mutations other than the one or more mutations of interest, or a plant that contains a subset of mutations. Phenotyping can be performed in a greenhouse and/or laboratory and/or in the field. In some embodiments, a population of plants can be selected that has improved heterosis, grain yield, tolerance to abiotic stress such as drought stress, osmotic stress, or nitrogen deficiency, soil aluminum, cold stress, frost stress, density stress, heat stress, oxidative stress, low light tolerance, herbicide stress, as well as improved water use efficiency, nitrogen use efficiency, phosphate use efficiency, seed oil or protein content, lignin content, biotic or pest resistance, biomass, chemical composition, plant architecture, flowering time, and/or biofuel conversion properties. In some cases, selection and/or screening can be carried out over multiple rounds of mutagenesis. Selection and/or screening can be carried out over one or more generations, and/or in more than one geographic location. In some cases, mutant plants can be grown and selected under conditions which induce a desired phenotype or are otherwise necessary to produce a desired phenotype in a mutant plant. In addition, selection and/or screening can be applied during a particular developmental stage in which the phenotype is expected to be exhibited by the plant. But, in many cases a phenotypic measure is yield of harvestable material under typical field cultivation conditions, i.e. without an intentionally applied selection pressure. Selection and/or screening can be carried out to choose those mutant plants having a statistically significant difference in yield (e.g., grain, vegetative biomass, or stem sucrose yield) relative to a control plant that lacks the combination of mutations. Selection and/or screening can be carried out to choose those mutant plants having a statistically significant difference in an abiotic stress tolerance level relative to a control plant that lacks the transgene. While the focus is most often on individuals with mutation combinations exhibiting improved performance, it is sometimes useful to identify stacks of significantly impaired performance over a control. Identification of undesirable mutations can be useful in designing subsequent improvement rounds so as to eliminate or minimize their occurrence.

To test for density stress tolerance, the testing population can be planted at an excessive density for the respective genetic background controls, and yield of individual plants scored for identifying the best performing individuals (see, for example, Mansfield and Humm, 2014, Crop Science, 57:157-173).

A heterotic group comprises a set of genotypes that perform well when crossed with genotypes from a different or complementary heterotic group. Inbred lines are classified into heterotic groups, and are further subdivided into families within a heterotic group, based on several criteria such as pedigree, molecular marker-based associations, and performance in hybrid combinations (see e.g. Smith at al. (1990) Theor. Appl. Gen. 80:833-840). For example for corn, the two most widely used heterotic groups in the United States are referred to as "Iowa Stiff Stalk Synthetic" (BSSS) and "Lancaster" or "Lancaster Sure Crop" (sometimes referred to as NSS, or iron-Stiff Stalk).

To test for nitrogen use efficiency, seeds of a testing population can be planted in a field using standard agronomic practices for the region, along with wild type controls of the same genetic background. Fertilizer is applied at about 50% of the optimal level for the respective location, so that yield of wild type plants is negatively impacted. See, Example 3.

Aside from pre-defined phenotypical observations to be made on testing populations such as those appropriate to screen for stress tolerances, the appearance of nearby planted negative controls can be useful in comparing to individuals in the testing population for observation of phenotypic differences that may be caused by some mutation combinations. Non-limiting examples of traits to be observed for example in corn include car diameter, car height, car leaf length, ear leaf weight, ear length, ear position, ear number, grain color, kernel length, kernel number, kernel row arrangement, kernel row number, kernel type, kernel width, leaf length, leaf width, tassel size, tassel type, and uppermost ear shape, and others traits described, for example, in the Maize Traits for Fieldbooks. See the world wide web at "cril.cimmyt.org/confluence/display/MBP/Activity+2.1.2+-+Maize+Traits+for+Fieldbooks."

The methods provided can be used to generate a very large number of different combinations of mutations. But very large numbers can also have drawbacks, so in designing combinations it is often desirable to limit the number of combinations. A limit can sometimes be imposed by the need to replicate individual genotypes so to understand the statistical significance of the phenotypes observed, and as such this limit is correlated with the size of any designed study. But, a limited "unit" of related variability is also helpful in side-by-side comparisons. For example, a single parent having four gRNAs can generate two different mutations in each allele of the four genomic targets. If first crossed to the wild type and the progeny then selfed, the mutations can form 1296 different combinations in homozygous and heterozygous states. Planting a population with having no more than this variability on a contiguous and identifiable plot helps by minimizing the environmental variability exposure and allowing for manageable comparative phenotyping. In other words, when related genotypes are replicated in a defined area, individuals can be readily examined for visually noticeable differences. As such, it is desirable to design variability units that occupy generally no more than about half a hectare or about one acre. For example, 1296 corn genotypes replicated 10-fold, i.e. about 13,000 plants, are typically planted on about one acre.

When seeking to first sort through the candidate mutations, it is preferable to make and phenotype a population of plants of a uniform genetic background if possible. However, a reduced number of candidates can be tested in variable genetic backgrounds. When the tested populations are sufficiently large, the interaction of different mutation combinations with known QTLs can thus be determined. Consequently, the methods provided herein can be used in conjunction with traditional breeding selections to produce cultivars with improved traits.

Genotyping

As described herein, plants that are identified as having an improved phenotypic feature can be genotyped using any methodology. Genotyping will often involve sequencing of the genomic target of the mutated materials of interest, i.e. at least around the residues targeted by gRNA used in mutagenesis, to determine the precise mutation introduced in specific individuals. Genotype refers to the combination of mutations present in an individual plant, which can be determined by a variety of methods known in the art, such as PCR with genomic target-specific primers or Southern blotting. Genotype can also refer to the combination of alleles that determines a characteristic or trait, and it can be indirectly characterized using markers or directly characterized by nucleic acid sequencing. Suitable markers include a genetic marker, or some other type of marker. The genotype can reflect the sequence of a portion of a chromosome, an entire chromosome, a portion of the genome, or of the entire genome. In some embodiments, leaf punches from individuals either to be selected for testing or identified as having an improved phenotypic feature can be genotyped. In some embodiments, seed chipping, in which the genetics of the seed can be assessed without destroying the seed, is used to select a subset of individuals from the progeny population for use as a testing. See, for example U.S. Pat. No. 7,502,113. Accordingly, a population can be created that mixes a large number of mutations. Subsequently, as it may become desirable as informed by new performance data, a subpopulation comprising only a defined subset of mutations, and possibly lacking transgenes such as a Cas-expressing transgene, can be selected and studied. Or similarly, individuals from a large population can be eliminated from a study by genotyping plants before planting if they are deemed to contain mutation combinations that are undesirable.

Improvement Rounds

Once a combination of mutations is identified by any means as having a desirable phenotypic performance, the improved materials can be subjected to additional rounds of improvement by adapting the methods used to identify the combination. In one type of improvement, the desired mutations are maintained in the background of all the plants of a testing population, and additional mutations combinations are also stacked. Mutation combinations can be maintained in the genetic background by making a testing population using individuals related by lineage to individuals of selected phenotypes. Alternatively, the combined genomic targets identified can be maintained as subject of de novo mutation in new testing populations, which may generate additional pairs or combinations of mutations of interest. Some of the additional mutations can be second site mutations in the same genomic targets that are part of the originally identified combination of mutations.

In some embodiments, improvements may be made using the top performing materials from a phenotyped population. For example, the best individuals can be crossed to each other and their progeny phenotyped. When the diversity of original mutations is large, this approach may more quickly result in recognition of improved combinations. This approach works well when the testing population is made up of inbred lines or uniform true breeding populations. When the testing population is made up of hybrid plants, it is possible to make one or more corresponding populations by crosses to isogenic parents so as to cause similar mutation segregation as in the hybrid testing population.

The improvement rounds can be cycled as many times as needed to develop mutation combinations of incrementally enhanced performance in the respective assays or field conditions.

The invention will be further described in the following examples, which do not limit the scope of the invention described in the claims.

EXAMPLES

Example 1: Selecting Salt Tolerance Targets

To rice make plants with enhanced salt tolerance, genomic targets comprising SEQ ID NOs: 6-10 are selected. Mutations of these targets are expected to impact the soil salt sensitivity of mutant plants. Pairs or combinations of mutations in these targets are therefore likely to produce a higher resistance to salt phenotype.

Example 2: RNA Targeting

SEQ ID NOs: 11-20 (which include the PAM 5'NGG3' for the *Streptococcus pyogenes Cas9*) can serve as RNA targeting sequences for different residues of the genomic target represented by SEQ ID NO: 6.

Example 3: gRNA-Expressing Transgenes

A transformation vector comprising gRNAs expressing genes is made. The vector comprises five tandem expression cassettes, each made up of the promoter of SEQ ID NO: 3 operably linked to a gRNA sequence made up of a RNA targeting sequence of fused to a scaffolding sequence, and followed 3' by a Pol III terminator. The five expression cassettes of this vector have the target RNAs of SEQ ID Nos: 20-24 (which include the PAM 5'NGG3' for the *Streptococcus pyogenes* Cas9), designed to mutate genomic targets comprising SEQ ID NOs: 6-10. The vectors are used in *Agrobacterium*-mediated transformation of rice.

Example 4: Selecting Corn Ear Morphology Targets

To make corn plants with enhanced grain yield, genomic targets comprising SEQ ID NOs: 26-39 are selected. Mutations of these targets are expected to impact the ear morphology of mutant plants. Pairs or combinations of mutations in these targets are therefore likely to produce corn cobs with higher grain yield.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a combination of genetic mutations that improves a phenotype of a plant, wherein said method comprises:
    (a) selecting a plurality of genomic targets for mutation, wherein said plurality of genomic targets comprises at least one of SEQ ID NOs: 6-10,
    (b) making a plant cell comprising a plurality of different gRNAs designed to mutate the genomic targets and a Cas9 polypeptide, wherein a plant descended from the plant cell has a plurality of germline mutations and wherein a RNA targeting sequence comprises at least one of SEQ ID NOs:11-20,
    (c) sexually crossing a first parental plant comprising at least a subset of the germline mutations to a second parental plant to produce a progeny population,
    (d) phenotyping the progeny population to select an individual with improved phenotype, and
    (e) genotyping the selected individual to identify the combination of genetic mutations that improves the phenotype of the plant.

2. The method of claim 1 wherein said plurality of genomic targets comprises is at least four.

3. The method of claim 1 wherein said first and second parental plants are *Zea mays*.

4. The method of claim 1 wherein a subset of said plurality of different gRNAs are designed to mutate distinct residues of the same genomic target.

5. The method of claim 1 wherein a subset of said plurality of different gRNAs is designed to mutate residues within conserved sequences of paralogous genes.

6. The method of claim 1 wherein making a plant cell comprises inserting gRNA-expressing transgenes.

7. The method of claim 1 wherein making a plant cell comprises contacting the cell with pre-assembled gRNA-Cas9 ribonucloeoproteins.

8. The method of claim 1 wherein making a plant cell comprises adding a Cas9 polypeptide-expressing transgene.

9. The method of claim 8 wherein adding the Cas9 polypeptide-expressing transgene comprises crossing to a plant having the Cas9 polypeptide-expressing transgene.

10. The method of claim 8 wherein the first parental plant is a progeny of selfing the plant having the germline mutations.

11. The method of claim 8 wherein the first parental plant is a progeny of a cross of the plant having germline mutations to a wild type plant.

12. The method of claim 8 wherein the first parental plant is a progeny of a cross of the plant having mutated germline to another plant, whereby the germline mutations of the first parental plant are heterozygous.

13. The method of claim 8 wherein the first parental plant does not comprise the Cas9 polypeptide-expressing transgene.

14. The method of claim 1 wherein the second plant has germline mutations.

15. The method of claim 1 wherein said first and second parental plants are isogenic and belong to complementary heterotic groups.

16. The method of claim 1, wherein said method comprises repeating steps (a) through (e), wherein said selecting of step (a) comprises genomic targets determined to be present within said selected individual in step (d).

17. The method of claim 1, wherein said method comprises repeating steps (a) through (e), wherein said first or said second parental plants are related by lineage to an individual selected in step (d).

18. A method for making a collection of seeds, wherein the embryonic cells of said seeds comprise a combination of genetic mutations identified by the method of claim 1.

19. The method of claim 1, wherein said first parental plant and said second parental plant are selected from the group consisting of *Zea mays, Sorghum bicolor, Triticum aestivum*, and *Oryza sativa*.

20. The method of claim 1, wherein said first parental plant or said second parental plant is cytoplasmically male sterile.

21. The method of claim 1, wherein said selecting of step (d) is based at least in part on performance under field testing conditions.

22. The method of claim 1, wherein said selecting of step (d) is based at least in part on water use efficiency, nitrogen use efficiency, seed oil content, or plant density stress performance.

23. The method of a claim 1, wherein phenotyping said progeny comprises using seed chipping to select a subset of individuals from said progeny population.

* * * * *

SEQUENCE LISTING

<160> NUMBER OF SEQ ID NOS: 39

<210> SEQ ID NO 1
<211> LENGTH: 4395
<212> TYPE: DNA
<213> ORGANISM: Streptococcus pyogenes

<400> SEQUENCE: 1

```
atgggcggta ggcgtgtacg gtgggaggtc tatataagca gagctcgttt agtgaaccgt      60
cagaattttg taatacgact cactataggg cggccgggaa ttcgtcgact ggaaccggta     120
```

```
ccgaggagat ctgccgccgc gatcgccatg gataagaaat actcaatagg actggatatt      180
ggcacaaata gcgtcggatg ggctgtgatc actgatgaat ataaggttcc ttctaaaaag      240
ttcaaggttc tgggaaatac agaccgccac agtatcaaaa aaaatcttat agggctctt       300 ctgtttgaca gtgagagac agccgaagct actagactca aacggacagc taggagaagg       360
tatacaagac ggaagaatag gatttgttat ctccaggaga ttttttcaaa tgagatggcc      420
aaagtggatg atagtttctt tcatagactt gaagagtctt ttttggtgga agaagacaag      480
aagcatgaaa gacatcctat ttttggaaat atagtggatg aagttgctta tcacgagaaa     540
tatccaacta tctatcatct gagaaaaaaa ttggtggatt ctactgataa agccgatttg     600
cgcctgatct atttggccct ggcccacatg attaagttta gaggtcattt tttgattgag     660
ggcgatctga atcctgataa tagtgatgtg acaaactgt ttatccagtt ggtgcaaacc      720
tacaatcaac tgtttgaaga aaaccctatt aacgcaagtg gagtggatgc taaagccatt      780
ctttctgcaa gattgagtaa atcaagaaga ctggaaaatc tcattgctca gctcccccggt    840 gagaagaaaa atggcctgtt tgggaatctc attgctttgt cattgggttt gaccccctaat    900 tttaaatcaa attttgattt ggcagaagat gctaaactcc agctttcaaa agatacttac    960
gatgatgatc tggataatct gttggctcaa attggggatc aatatgctga tttgttttttg   1020 gcagctaaga atctgtcaga tgctattctg cttttcagaca tcctgagagt gaatactgaa   1080
ataactaagg ctcccctgtc agcttcaatg attaaacgct acgatgaaca tcatcaagac    1140
ttgactcttc tgaaagccct ggttagacaa caacttccag aaaagtataa agaaatcttt    1200
tttgatcaat caaaaaacgg atatgcaggt tatattgatg gcggcgcaag ccaagaagaa    1260
ttttataaat ttatcaaacc aattctggaa aaaatggatg gtactgagga actgttggtg    1320
aaactgaata gagaagattt gctgcgcaag caacggacct ttgacaacgg ctctattccc    1380
catcaaattc acttgggtga gctgcatgct attttgagaa gacaagaaga cttttatcca    1440
tttctgaaag acaatagaga gaagattgaa aaaatcttga ctttaggat tccttattat    1500 gttggtccat tggccagagg caatagtagg tttgcatgga tgactcggaa gtctgaagaa    1560
acaattaccc catggaattt tgaagaagtt gtcgataaag gtgcttcagc tcaatcattt    1620
attgaacgca tgacaaactt tgataaaat cttccaaatg aaaaagtgct gccaaaacat     1680
agtttgcttt atgagtattt taccgtttat aacgaattga caaggtcaa atatgttact     1740 gaaggaatga aaaaccagc atttctttca ggtgaacaga agaaagccat tgttgatctg     1800
ctcttcaaaa caaataggaa agtgaccgtt aagcaactga agaagatta tttcaaaaaa    1860 atagaatgtt ttgatagtgt tgaaatttca ggagttgaag atagatttaa tgcttcactg    1920
ggtacatacc atgatttgct gaaaattatt aaagataaag atttttggga taatgaagaa   1980
aatgaagaca tcctggagga tattgttctg acattgaccc tgtttgaaga tagggagatg   2040
attgaggaaa gacttaaaac atacgctcac ctctttgatg ataaggtgat gaaacagctt   2100
aaaagacgca gatatactgg ttggggaagg ttgtccagaa aattgattaa tggtattagg   2160
gataagcaat ctggcaaaac aatactggat ttttttgaaat cagatggttt tgccaatcgc   2220
aattttatgc agctcatcca tgatgatagt ttgacattta aagaagacat ccaaaaagca   2280
caagtgtctg gacaaggcga tagtctgcat gaacatattg caaatctggc tggtagccct   2340
gctattaaaa aaggtattct ccagactgtg aaagttgttg atgaattggt caaagtgatg   2400
gggcggcata agccagaaaa tatcgttatt gaaatggcaa gagaaaatca gacaactcaa   2460
```

-continued

| | |
|---|---|
| aagggccaga aaaattccag agagaggatg aaaagaatcg aagaaggtat caaagaactg | 2520 |
| ggaagtcaga ttcttaaaga gcatcctgtt gaaaatactc aattgcaaaa tgaaaagctc | 2580 |
| tatctctatt atctccaaaa tggaagagat atgtatgtgg accaagaact ggatattaac | 2640 |
| aggctgagtg attatgatgt cgatcacatt gttccacaaa gtttccttaa agacgattca | 2700 |
| atagacaata aggtcctgac caggtctgat aaaaatagag gtaaatccga taacgttcca | 2760 |
| agtgaagaag tggtcaaaaa gatgaaaaac tattggagac aacttctgaa cgccaagctg | 2820 |
| atcactcaaa ggaagtttga taatctgacc aaagctgaaa gaggaggttt gagtgaactt | 2880 |
| gataaagctg gttttatcaa acgccaattg gttgaaactc gccaaatcac taagcatgtg | 2940 |
| gcacaaattt tggatagtcg catgaatact aaatacgatg aaaatgataa acttattaga | 3000 |
| gaggttaaag tgattaccct gaaatctaaa ctggtttctg acttcagaaa agatttccaa | 3060 |
| ttctataaag tgagagagat taacaattac catcatgccc atgatgccta tctgaatgcc | 3120 |
| gtcgttggaa ctgctttgat taagaaatat ccaaaacttg aaagcgagtt tgtctatggt | 3180 |
| gattataaag tttatgatgt taggaaaatg attgctaagt ctgagcaaga aataggcaaa | 3240 |
| gcaaccgcaa agtatttctt ttactctaat atcatgaact tcttcaaaac agaaattaca | 3300 |
| cttgcaaatg gagagattcg caaacgcccct ctgatcgaaa ctaatgggga aactggagaa | 3360 |
| attgtctggg ataaagggag agattttgcc acagtgcgca agtgttgtc catgccccaa | 3420 |
| gtcaatatcg tcaagaaaac agaagtgcag acaggcggat tctctaagga gtcaattctg | 3480 |
| ccaaaaagaa attccgacaa gctgattgct aggaaaaaag actgggaccc aaaaaaatat | 3540 |
| ggtggttttg atagtccaac cgtggcttat tcagtcctgg tggttgctaa ggtggaaaaa | 3600 |
| gggaaatcca agaagctgaa atccgttaaa gagctgctgg ggatcacaat tatggaaaga | 3660 |
| agttccttg aaaaaaatcc cattgacttt ctggaagcta aggatataaa ggaagttaaa | 3720 |
| aaagacctga tcattaaact gcctaaatat agtcttttg agctggaaaa cggtaggaaa | 3780 |
| cggatgctgg ctagtgccgg agaactgcaa aaaggaaatg agctggctct gccaagcaaa | 3840 |
| tatgtgaatt ttctgtatct ggctagtcat tatgaaaagt tgaagggtag tccagaagat | 3900 |
| aacgaacaaa acaattgtt tgtggagcag cataagcatt atctggatga gattattgag | 3960 |
| caaatcagtg aattttctaa gagagttatt ctggcagatg ccaatctgga taaagttctt | 4020 |
| agtgcatata caaacatag agacaaacca ataagagaac aagcagaaaa tatcattcat | 4080 |
| ctgtttacct tgaccaatct ggagcaccc gctgctttta aatactttga tacaacaatt | 4140 |
| gataggaaaa gatataccc tacaaaagaa gttctggatg ccactcttat ccatcaatcc | 4200 |
| atcactggtc tttatgaaac acgcattgat ttgagtcagc tgggaggtga ccccaagaaa | 4260 |
| aaacgcaagg tggaagatcc taagaaaaag cggaaagtgg acacgcgtac gcggccgctc | 4320 |
| gagcagaaac tcatctcaga agaggatctg gcagcaaatg atatcctgga ttacaaggat | 4380 |
| gacgacgata aggtt | 4395 |

<210> SEQ ID NO 2
<211> LENGTH: 1465
<212> TYPE: PRT
<213> ORGANISM: Streptococcus pyogenes

<400> SEQUENCE: 2

Met Gly Gly Arg Arg Val Arg Trp Glu Val Tyr Ile Ser Arg Ala Arg
1               5                   10                  15

Leu Val Asn Arg Gln Asn Phe Val Ile Arg Leu Thr Ile Gly Arg Pro
            20                  25                  30

```
Gly Ile Arg Arg Leu Glu Pro Val Pro Arg Ser Ala Ala Ile
         35                  40                 45

Ala Met Asp Lys Lys Tyr Ser Ile Gly Leu Asp Ile Gly Thr Asn Ser
         50                  55                 60

Val Gly Trp Ala Val Ile Thr Asp Glu Tyr Lys Val Pro Ser Lys Lys
 65                  70                  75                  80

Phe Lys Val Leu Gly Asn Thr Asp Arg His Ser Ile Lys Lys Asn Leu
                 85                  90                  95

Ile Gly Ala Leu Leu Phe Asp Ser Gly Glu Thr Ala Glu Ala Thr Arg
                100                 105                 110

Leu Lys Arg Thr Ala Arg Arg Arg Tyr Thr Arg Arg Lys Asn Arg Ile
             115                 120                 125

Cys Tyr Leu Gln Glu Ile Phe Ser Asn Glu Met Ala Lys Val Asp Asp
             130                 135                 140

Ser Phe Phe His Arg Leu Glu Glu Ser Phe Leu Val Glu Glu Asp Lys
145                 150                 155                 160

Lys His Glu Arg His Pro Ile Phe Gly Asn Ile Val Asp Glu Val Ala
                 165                 170                 175

Tyr His Glu Lys Tyr Pro Thr Ile Tyr His Leu Arg Lys Lys Leu Val
             180                 185                 190

Asp Ser Thr Asp Lys Ala Asp Leu Arg Leu Ile Tyr Leu Ala Leu Ala
             195                 200                 205

His Met Ile Lys Phe Arg Gly His Phe Leu Ile Glu Gly Asp Leu Asn
     210                 215                 220

Pro Asp Asn Ser Asp Val Asp Lys Leu Phe Ile Gln Leu Val Gln Thr
225                 230                 235                 240

Tyr Asn Gln Leu Phe Glu Glu Asn Pro Ile Asn Ala Ser Gly Val Asp
                 245                 250                 255

Ala Lys Ala Ile Leu Ser Ala Arg Leu Ser Lys Ser Arg Arg Leu Glu
             260                 265                 270

Asn Leu Ile Ala Gln Leu Pro Gly Glu Lys Lys Asn Gly Leu Phe Gly
         275                 280                 285

Asn Leu Ile Ala Leu Ser Leu Gly Leu Thr Pro Asn Phe Lys Ser Asn
         290                 295                 300

Phe Asp Leu Ala Glu Asp Ala Lys Leu Gln Leu Ser Lys Asp Thr Tyr
305                 310                 315                 320

Asp Asp Asp Leu Asp Asn Leu Leu Ala Gln Ile Gly Asp Gln Tyr Ala
             325                 330                 335

Asp Leu Phe Leu Ala Ala Lys Asn Leu Ser Asp Ala Ile Leu Leu Ser
             340                 345                 350

Asp Ile Leu Arg Val Asn Thr Glu Ile Thr Lys Ala Pro Leu Ser Ala
             355                 360                 365

Ser Met Ile Lys Arg Tyr Asp Glu His His Gln Asp Leu Thr Leu Leu
     370                 375                 380

Lys Ala Leu Val Arg Gln Gln Leu Pro Glu Lys Tyr Lys Glu Ile Phe
385                 390                 395                 400

Phe Asp Gln Ser Lys Asn Gly Tyr Ala Gly Tyr Ile Asp Gly Gly Ala
                 405                 410                 415

Ser Gln Glu Glu Phe Tyr Lys Phe Ile Lys Pro Ile Leu Glu Lys Met
                 420                 425                 430

Asp Gly Thr Glu Glu Leu Leu Val Lys Leu Asn Arg Glu Asp Leu Leu
             435                 440                 445
```

-continued

```
Arg Lys Gln Arg Thr Phe Asp Asn Gly Ser Ile Pro His Gln Ile His
450                 455                 460
Leu Gly Glu Leu His Ala Ile Leu Arg Arg Gln Glu Asp Phe Tyr Pro
465                 470                 475                 480
Phe Leu Lys Asp Asn Arg Glu Lys Ile Glu Lys Ile Leu Thr Phe Arg
                485                 490                 495
Ile Pro Tyr Tyr Val Gly Pro Leu Ala Arg Gly Asn Ser Arg Phe Ala
                500                 505                 510
Trp Met Thr Arg Lys Ser Glu Thr Ile Thr Pro Trp Asn Phe Glu
                515                 520                 525
Glu Val Val Asp Lys Gly Ala Ser Ala Gln Ser Phe Ile Glu Arg Met
530                 535                 540
Thr Asn Phe Asp Lys Asn Leu Pro Asn Glu Lys Val Leu Pro Lys His
545                 550                 555                 560
Ser Leu Leu Tyr Glu Tyr Phe Thr Val Tyr Asn Glu Leu Thr Lys Val
                565                 570                 575
Lys Tyr Val Thr Glu Gly Met Arg Lys Pro Ala Phe Leu Ser Gly Glu
                580                 585                 590
Gln Lys Lys Ala Ile Val Asp Leu Leu Phe Lys Thr Asn Arg Lys Val
                595                 600                 605
Thr Val Lys Gln Leu Lys Glu Asp Tyr Phe Lys Lys Ile Glu Cys Phe
610                 615                 620
Asp Ser Val Glu Ile Ser Gly Val Glu Asp Arg Phe Asn Ala Ser Leu
625                 630                 635                 640
Gly Thr Tyr His Asp Leu Leu Lys Ile Ile Lys Asp Lys Asp Phe Leu
                645                 650                 655
Asp Asn Glu Glu Asn Glu Asp Ile Leu Glu Asp Ile Val Leu Thr Leu
                660                 665                 670
Thr Leu Phe Glu Asp Arg Glu Met Ile Glu Glu Arg Leu Lys Thr Tyr
                675                 680                 685
Ala His Leu Phe Asp Asp Lys Val Met Lys Gln Leu Lys Arg Arg Arg
690                 695                 700
Tyr Thr Gly Trp Gly Arg Leu Ser Arg Lys Leu Ile Asn Gly Ile Arg
705                 710                 715                 720
Asp Lys Gln Ser Gly Lys Thr Ile Leu Asp Phe Leu Lys Ser Asp Gly
                725                 730                 735
Phe Ala Asn Arg Asn Phe Met Gln Leu Ile His Asp Asp Ser Leu Thr
                740                 745                 750
Phe Lys Glu Asp Ile Gln Lys Ala Gln Val Ser Gly Gln Gly Asp Ser
                755                 760                 765
Leu His Glu His Ile Ala Asn Leu Ala Gly Ser Pro Ala Ile Lys Lys
770                 775                 780
Gly Ile Leu Gln Thr Val Lys Val Asp Glu Leu Val Lys Val Met
785                 790                 795                 800
Gly Arg His Lys Pro Glu Asn Ile Val Ile Glu Met Ala Arg Glu Asn
                805                 810                 815
Gln Thr Thr Gln Lys Gly Gln Lys Asn Ser Arg Glu Arg Met Lys Arg
                820                 825                 830
Ile Glu Glu Gly Ile Lys Glu Leu Gly Ser Gln Ile Leu Lys Glu His
                835                 840                 845
Pro Val Glu Asn Thr Gln Leu Gln Asn Glu Lys Leu Tyr Leu Tyr Tyr
850                 855                 860
Leu Gln Asn Gly Arg Asp Met Tyr Val Asp Gln Glu Leu Asp Ile Asn
```

```
                865                 870                 875                 880
Arg Leu Ser Asp Tyr Asp Val Asp His Ile Val Pro Gln Ser Phe Leu
                    885                 890                 895
Lys Asp Asp Ser Ile Asp Asn Lys Val Leu Thr Arg Ser Asp Lys Asn
                900                 905                 910
Arg Gly Lys Ser Asp Asn Val Pro Ser Glu Glu Val Lys Lys Met
            915                 920                 925
Lys Asn Tyr Trp Arg Gln Leu Leu Asn Ala Lys Leu Ile Thr Gln Arg
            930                 935                 940
Lys Phe Asp Asn Leu Thr Lys Ala Glu Arg Gly Gly Leu Ser Glu Leu
945                 950                 955                 960
Asp Lys Ala Gly Phe Ile Lys Arg Gln Leu Val Glu Thr Arg Gln Ile
                    965                 970                 975
Thr Lys His Val Ala Gln Ile Leu Asp Ser Arg Met Asn Thr Lys Tyr
                980                 985                 990
Asp Glu Asn Asp Lys Leu Ile Arg Glu Val Lys Val Ile Thr Leu Lys
                    995                1000                1005
Ser Lys Leu Val Ser Asp Phe Arg Lys Asp Phe Gln Phe Tyr Lys
    1010                1015                1020
Val Arg Glu Ile Asn Asn Tyr His His Ala His Asp Ala Tyr Leu
    1025                1030                1035
Asn Ala Val Val Gly Thr Ala Leu Ile Lys Lys Tyr Pro Lys Leu
    1040                1045                1050
Glu Ser Glu Phe Val Tyr Gly Asp Tyr Lys Val Tyr Asp Val Arg
    1055                1060                1065
Lys Met Ile Ala Lys Ser Glu Gln Glu Ile Gly Lys Ala Thr Ala
    1070                1075                1080
Lys Tyr Phe Phe Tyr Ser Asn Ile Met Asn Phe Phe Lys Thr Glu
    1085                1090                1095
Ile Thr Leu Ala Asn Gly Glu Ile Arg Lys Arg Pro Leu Ile Glu
    1100                1105                1110
Thr Asn Gly Glu Thr Gly Glu Ile Val Trp Asp Lys Gly Arg Asp
    1115                1120                1125
Phe Ala Thr Val Arg Lys Val Leu Ser Met Pro Gln Val Asn Ile
    1130                1135                1140
Val Lys Lys Thr Glu Val Gln Thr Gly Gly Phe Ser Lys Glu Ser
    1145                1150                1155
Ile Leu Pro Lys Arg Asn Ser Asp Lys Leu Ile Ala Arg Lys Lys
    1160                1165                1170
Asp Trp Asp Pro Lys Lys Tyr Gly Gly Phe Asp Ser Pro Thr Val
    1175                1180                1185
Ala Tyr Ser Val Leu Val Val Ala Lys Val Glu Lys Gly Lys Ser
    1190                1195                1200
Lys Lys Leu Lys Ser Val Lys Glu Leu Leu Gly Ile Thr Ile Met
    1205                1210                1215
Glu Arg Ser Ser Phe Glu Lys Asn Pro Ile Asp Phe Leu Glu Ala
    1220                1225                1230
Lys Gly Tyr Lys Glu Val Lys Lys Asp Leu Ile Ile Lys Leu Pro
    1235                1240                1245
Lys Tyr Ser Leu Phe Glu Leu Glu Asn Gly Arg Lys Arg Met Leu
    1250                1255                1260
Ala Ser Ala Gly Glu Leu Gln Lys Gly Asn Glu Leu Ala Leu Pro
    1265                1270                1275
```

```
Ser Lys Tyr Val Asn Phe Leu Tyr Leu Ala Ser His Tyr Glu Lys
    1280            1285                1290

Leu Lys Gly Ser Pro Glu Asp Asn Glu Gln Lys Gln Leu Phe Val
    1295            1300                1305

Glu Gln His Lys His Tyr Leu Asp Glu Ile Ile Glu Gln Ile Ser
    1310            1315                1320

Glu Phe Ser Lys Arg Val Ile Leu Ala Asp Ala Asn Leu Asp Lys
    1325            1330                1335

Val Leu Ser Ala Tyr Asn Lys His Arg Asp Lys Pro Ile Arg Glu
    1340            1345                1350

Gln Ala Glu Asn Ile Ile His Leu Phe Thr Leu Thr Asn Leu Gly
    1355            1360                1365

Ala Pro Ala Ala Phe Lys Tyr Phe Asp Thr Thr Ile Asp Arg Lys
    1370            1375                1380

Arg Tyr Thr Ser Thr Lys Glu Val Leu Asp Ala Thr Leu Ile His
    1385            1390                1395

Gln Ser Ile Thr Gly Leu Tyr Glu Thr Arg Ile Asp Leu Ser Gln
    1400            1405                1410

Leu Gly Gly Asp Pro Lys Lys Lys Arg Lys Val Glu Asp Pro Lys
    1415            1420                1425

Lys Lys Arg Lys Val Asp Thr Arg Thr Arg Pro Leu Glu Gln Lys
    1430            1435                1440

Leu Ile Ser Glu Glu Asp Leu Ala Ala Asn Asp Ile Leu Asp Tyr
    1445            1450                1455

Lys Asp Asp Asp Asp Lys Val
    1460            1465

<210> SEQ ID NO 3
<211> LENGTH: 1000
<212> TYPE: DNA
<213> ORGANISM: Zea mays

<400> SEQUENCE: 3
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga ggggcatca    480 aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt ccaggccca gttgtaaaag ctaaaatgct    660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
```

```
gtggagcgta ccttataaac cgagccgcaa gcaccgaatt                         1000
```

<210> SEQ ID NO 4
<211> LENGTH: 381
<212> TYPE: DNA
<213> ORGANISM: Sorghum bicolor

<400> SEQUENCE: 4

```
gcttgctcaa cttagcactt agcagtaaca ttttagtaca ctgattgcga ttgttagcag     60
tactccgggt tagcacctag cagtactccg ggagctctgt gaactgtgaa gagtgaacta    120
caaccatcta ggaatcagct gagcttatta ttatcttacc ttcttttta tcctcaggtg    180
aggcattagc attaagccac caacaggggt aaagctaatg cagcatcgat gggctcgacc    240
tgaactctga acttctgaag cccacacata caacaagtgg cccagtgcgc aatatgctgg    300
ccactcccac cgattagtac cacctcggct cctcaaatgc gtagaagcta acttaaaagc    360
tcagttctcc agccattcag c                                              381
```

<210> SEQ ID NO 5
<211> LENGTH: 2000
<212> TYPE: DNA
<213> ORGANISM: Zea mays

<400> SEQUENCE: 5

```
cgccgagcaa gtcaatcgcc ccatcatgcg gacttgctcg gcaaatgggc tagagagagg     60
tttatgggcc tcgccttggg taccctgttc ccggtacccg acaatgacct tcctcggatg    120
ctgataggtc aattaaagaa acaacaatgg atatatatgg ataggtatag aggtgtaagg    180
ctatctctag aacgttgcct attcttatac ccatattcaa actttattga taaaatgttg    240
gacaggtctg gtgcccttgg aacaagtgtt gtttccattc tccagagtgg actacttctt    300
gcgctgattt gtttggtgag ttaccgaagg agatttaggg gaagaaaaac agggcactta    360
taagtgatat attgtttatc tcagatgtat tgatcacttc tctggtattg gtgcaatgta    420
ttggggtacc gatcactgag taatcacgca atgtattggg gtactaaatc ctctctggta    480
tcgattattc atgcaatgta ttgacgattt taataagtga atcgccaatg tatatgatat    540
ttccactggc ggtgtactta atacagccgc cagtgtatat acatcatttc cactgacggt    600
tcagttaagt gaaccgcaag tgtatatgac atttccactg gcggtgtact ttatagaacc    660
gccagtgtat atacatcctt tacactgacg gttcagttaa gtgaaccacc agtgtatatg    720
atatttccac tggcggtgta cttaatacag ctgccagtgt atatacatcc tttatactga    780
cggttcagtt aagtgaaccg acagtgtata tgatatttcc actgccggtg tacttaatac    840
agctgccagt gtatatacat cctttatact gacggttcag ttaagtgaac cgccagtata    900
tattatatt ccactggcgg tttacttaat aaaaccgcaa gtgtaaatac atcatttaca    960
ctgacagttt tgttaagtga accaccagcg tatatatatt tacactgccg gttcgttaag   1020
acgggcccgt ctgtttttt cactggcgtg ctgtaactga aaccgccatt ataaatttct   1080
acgtgccgcc accttagagc tcttttctac tagtgttaac ttcttttctt gtagaccatt   1140
tggaaaacag gaaacaacgc ggtactgtat tcaacaacag atggttgtcc acacctatga   1200
caatcatggc gtcaatgcag tagtaagttt gtcgtttttg tgtgtgtgtg tttattagcc   1260
gtttctttgt ttttttctt ctgttgagct ccaactttat gaaacgtcgt aagctggtaa   1320
ttatgaaatg taaggatttg gagagagaaa aaaacgggga gggaaaacca tgcatgctgc   1380
```

```
tgacgcgacg gccggacgca gacgcaacaa tgccccggt gcggcgttgt cgagcagcca      1440
ctgcaccacc ccacgcatca cctgcagtaa tctagcgacg gttttcctt atttattat      1500 ttatttattt atttcttc tctccctccc tccctcagat ttgtttcgt tttcattaat      1560 cgttattacc agcaattaat taactttat tattgattta ccaaaccgca ataaagaata     1620
tatatattct tttattaagg tccagtaata agcagcacag aagcgcaggt gcagcagcag    1680
cagcgtcagc gcccgaggcg cgcacgagag aaacagaggc tgacgaggtg gggcccgtgc    1740
gggccttgac caatcggagt tcgacaacag cctggccacc cacaaacaca cactccttcg    1800
cctcgcgccg gccgtcgtcg cctccctcca ccgaacgatc cctcctcctc ctcctcctcc    1860
tcctcctcgc atcccacccc accccacctt ctccttaaag ctacctgcct acccggcggt    1920
tgccgccgcc gcaatcgatc gaccggaaga gaaagagcag ctagctagct agcagatcgg    1980
agcacggcaa caaggcgatg                                                2000

<210> SEQ ID NO 6
<211> LENGTH: 1608
<212> TYPE: DNA
<213> ORGANISM: Oryza sativa

<400> SEQUENCE: 6
atggggatgg aggtggcggc ggcgcggctg ggggctctgt acacgacctc cgactacgcg      60
tcggtggtgt ccatcaacct gttcgtcgcg ctgctctgcg cctgcatcgt cctcggccac     120
ctcctcgagg agaatcgctg ggtcaatgag tccatcaccg cgctcatcat cgggctctgc    180
accggcgtgg tgatcttgct gatgaccaaa gggaagagct cgcacttatt cgtcttcagt    240
gaggatctct tcttcatcta cctcctccct ccgatcatct tcaatgcagg ttttcaggta    300
aagaaaaagc aattcttccg gaatttcatg acgatcacat tatttggagc cgtcgggaca    360
atgatatcct ttttcacaat atctattgct gccattgcaa tattcagcag aatgaacatt    420
ggaacgctgg atgtaggaga ttttcttgca attggagcca tcttttctgc gacagattct    480
gtctgcacat tgcaggtcct caatcaggat gagacaccct tttgtacag tctggtattc    540 ggtgaaggtg ttgtgaacga tgctacatca attgtgcttt tcaacgcact acagaacttt    600
gatcttgtcc acatagatgc ggctgtcgtt ctgaaattct ggggaacttt cttttattta    660 ttttgtcga gcaccttcct ggagtattt gctggattgc tcagtgcata cataatcaag    720
aagctataca ttggaaggca ttctactgac cgtgaggttg cccttatgat gctcatggct    780
tacctttcat atatgctggc tgagttgcta gatttgagcg gcattctcac cgtattcttc    840
tgtggtattg taatgtcaca ttacacttgg cataacgtca cagagagttc aagagttaca    900
acaaagcacg catttgcaac tctgtccttc attgctgaga cttttctctt cctgtatgtt    960
gggatggatg cattggatat tgaaaatgg gagtttgcca gtgacagacc tggcaaatcc    1020
attgggataa gctcaatttt gctaggattg gttctgattg gaagagctgc ttttgtattc    1080
ccgctgtcgt tcttgtcgaa cctaacaaag aaggcaccga tgaaaaaaat aacctggaga    1140
cagcaagttg taatatggtg ggctgggctg atgagaggag ctgtgtcgat tgctcttgct    1200
tacaataagt ttacaagatc tggccatact cagctgcacg gcaatgcaat aatgatcacc    1260
agcaccatca ctgtcgttct ttttagcact atggtatttg ggatgatgac aaagccattg    1320
atcaggctgc tgctaccggc ctcaggccat cctgtcacct ctgagccttc atcaccaaag    1380
tccctgcatt ctcctctcct gacaagcatg caaggttctg acctcgagag tacaaccaac    1440
attgtgaggc cttccagcct ccggatgctc ctcaccaagc cgacccacac tgtccactac    1500
```
tactggcgca agttcgacga cgcgctgatg cgaccgatgt ttggcgggcg cgggttcgtg    1560
cccttctccc ctggatcacc aaccgagcag agccatggag aagatga                 1608

<210> SEQ ID NO 7
<211> LENGTH: 1503
<212> TYPE: DNA
<213> ORGANISM: Oryza sativa

<400> SEQUENCE: 7
atgggtaaga aggaaattg gttcagtgct gtcaagaaag tcttcagctc atccgatcca     60
gatgggaggg aagctaagat cgagaaggcg acaagtcga gatccaggag gaaatggcca    120 tttgaaagt ctaagaagtc tgatccttgg acctcaacag tggcagtgcc tacctctaca    180
gcaccgcctc cacagccgcc accgccaccg ccaacacacc ctatccagcc acagcctgag    240
gagatcaaag atgtcaaggc tgttgaaact gacagtgaac agaacaagca tgcgtactct    300
gttgcacttg cctctgctgt tgctgcagaa gctgctgccg tcgctgccca ggccgctgct    360
gaggtggtcc gcctcacaac agccaccacg gctgtgccga atcgcctgt tagttcaaag    420 gatgagcttg ccgctatcaa gattcagact gccttcaggg gttatctggc aagaagagcg    480
ctgcgagcac ttagagggct agttagattg aagtcgctgg ttgatggaaa cgccgtcaaa    540
cgacaaactg cgcacacctt gcattgcaca caaaccatga ccagagttca aactcaaata    600
tactctagaa gggtgaagat ggaggaggaa aaacaggctc ttcaaaggca gctacaatta    660
aagcatcaga gggaacttga gaaaatgaag attgatgaag attgggatca tagccatcag    720
tccaaggagc aggttgagac cagcctaatg atgaaacaag aagctgcgct aaggcgggaa    780
agagctcttg cctatgcatt ttctcaccag tggaagaatt ctggccgaac tataacacct    840
accttcacgg atcaagggaa tcctaactgg ggatggagct ggatggaacg ctggatgaca    900
tcaaggcctt gggagagccg agtgatatca gataaggatc ctaaggacca ttattcaaca    960
aagaatccca gcactagcgc ttctcgtact tatgtacccc gcgcaatctc aatccagaga   1020
cctgcaacac caaacaagtc aagccgtcca ccaagtcggc aatcgccatc aactccccg   1080 tcaagggtcc cctcagttac cggaaagatc agaccagcaa gtccacggga tagctggcta   1140
tataaggagg atgacttgag gagcatcaca agcatacgct ctgaacgccc aaggaggcag   1200
agcacaggtg gtgcctctgt tcgggatgat gcgagcctaa caagcacacc agctctcccc   1260
agctacatgc agtccacaga gtctgcaagg gcaaagtctc ggtaccgcag tctattgact   1320
gacaggtttg aggttcctga gagtaccc tggtccatt cttcaataaa gaagcgctta   1380
tccttcccag tcgcagacaa accaaatggt gagcatgcag ataagctgat ggaaagaggg   1440
aggcgtcatt cagaccctcc taaggtggat cctgcctcac tgaaggatgt tccggtttca   1500
taa                                                                1503

<210> SEQ ID NO 8
<211> LENGTH: 3447
<212> TYPE: DNA
<213> ORGANISM: Oryza sativa

<400> SEQUENCE: 8
atggacaatc ccgaggcgga gcctgatgac gcggtgctct tcgtcggggt ctccctcgtc     60
ctcggcatcg cctcccgcca cctcctccgg ggcacccgcg tccctacac cgtcgccctc    120 ctcgtcctcg gcgtcgccct cggatcgctc gaatttggca caaacatgg cctgggcaaa    180

```
ctcggagccg gcattcgtat ctgggctaac attaatcctg atcttcttct ggctgttttt    240
ctacccgctc ttcttttga aagttccttt tccatggaaa tacaccaaat caagaaatgt    300
atggcacaaa tggtgttact tgctggacct ggtgtgctaa tatcaacctt tttcctaggc    360
tctgctctaa agctcacttt tccatacaac tggaactgga aaacatcatt gttgcttggt    420
ggattgctta gtgcaactga ccccgttgct gttgttgcac tgctaaaaga acttggcgca    480
agtaaaaagc ttagtaccat aattgaggga gaatccttaa tgaatgatgg gactgctatt    540
gttgtgtatc agttattcta taggatggtg cttggaagaa ctttcgatgc aggatcaata    600
ataaaattct tgtcagaagt ttcacttgga gctgttgctc tgggccttgc ttttggaatt    660
gcatcagtac tgtggctggg ctttatttt aatgatacaa tcatagagat cgcacttact    720
cttgctgtca gctacattgc tttcttcact gcacaagatg cactggaggt ctctggtgtt    780
ttgaccgtca tgacactggg aatgttctat gccgcttttg caaaaactgc ttttaagggt    840
gacagtcagc aaagcttgca tcatttctgg gaaatggttg cttatatagc aaacacactt    900
atatttatac tgagtggggt tgttattgca gatggagtac tagaaaataa tgtccatttc    960
gagaggcacg gtgcttcatg gggcttcctt cttctgctct atgtatttgt gcaaatttct   1020
cggatattag ttgttgttat tttgtatcca ttgttgcgcc actttgggta tggtttggac   1080
ttgaaagaag ccacaattct tgtttgggcg ggactgcgag gggctgttgc tctgtctcta   1140
tcattatctg ttaagcgtgc tagtgatgca gttcagaccc atctgaaacc agttgacgga   1200
acaatgtttg tgttcttcac tggtggcatc gtgttttga cattgatttt taatggttct   1260
actacacaat ttttgttgca tctacttgga atggacagat tagcagcaac aaagcttcgc   1320
atattgaatt atacaaaata tgaaatgcta aacaaggcat ggaggctttt tggtgatctt   1380
agggatgatg aggaacttgg tcctcctgct gattgggtta ctgtaaagaa atatatcaca   1440
tgcttgaatg acttggacga tgagcctgtg catcctcatg ctgtttctga cagaaatgat   1500
cgcatgcata ccatgaactt aagggacatc cgtgtgcggc ttctaaatgg tgtccaagct   1560
gcttactggg gaatgcttga agaaggacga ataactcaag ccactgcaaa tattttaatg   1620
agatcggttg atgaagctat ggatcttgtt cctacccaag aattatgtga ctggaagggt   1680
ttgcggtcca atgtccattt tccaaattac tataggttcc ttcaaatgag caggttgcca   1740
cgaaggctta tcacttactt cacagtagaa agactggagt caggatgtta catctgtgct   1800
gcatttctcc gtgctcatag aatcgcaaga cggcagctac atgactttct tggtgatagt   1860
gaggttgcaa gaattgttat tgatgaaagt aatgctgagg gagaggaggc tagaaaattc   1920
ttggaagatg ttcgtgttac attccctcag gtgcttcgtg tgctgaagac tcgacaagta   1980
acatattcgg tattgaccca cttgagtgag tatattcaaa atctccagaa gactgggttg   2040
ctggaagaaa aggaaatggc ccatctagat gatgctttgc agacagactt gaagaagttc   2100
aagaggaatc caccattggt aaaaatgcca agagtcagtg atcttttgaa cactcatccg   2160
ttagttggtg cactgcctgc tgcgatgcgt gatcctttat aaatagcac aaaggaaaca   2220
gtaaaaggac atggcacaat ccttttataga gagggctcaa ggccaactgg tatatggctt   2280
gtttcgattg gagtagtaaa gtggacaagt cagagattaa gcagcaggca ttcattggat   2340
ccaatttat cacatggcag cactttgggc ctgtatgagg tgctgattgg aaaaccttat   2400
atctgtgaca tgattacaga ttctgtggtg cactgcttct tcattgaagc tgaaaagata   2460
gagcaattgc gtcaatcaga tccttctatt gagattttc tgtggcagga aagtgctcta   2520
gtcgttgcca ggcttttgct ccctatgatg tttgagaaaa tggcaacaca tgagctcagg   2580
```

```
gttctcatca ctgaaagatc tactatgaac atctacatta agggcgaaga aattgaactt     2640
gagcagaatt tcattggcat cttactggaa ggatttttga agaccaagaa ccaaactttg     2700
atcacacctc cagggttact gctaccacca aatgccgact tgaacttatt tggtctcgag     2760
tcatcagcta taaaccgcat tgactactgt tatacagcac ccagctatca ggtggaggct     2820
agagcaagga ttttgttcgt tgagataggg aggcccgaaa tagaggcgga tctgcaaagg     2880
agtgcgtcat tgatatctca aacccttgaa ctgcctcgga cacaaagcaa ggagcacagc     2940
ggtttgctca gctggccgga aagcttcaga aaatccaggg gagctcagaa tggtgccagc     3000
ttaactgaaa tcagagacca tccagcaagc ttctctgcaa gagcattgca gctgagcatg     3060
tacgggagca tgatcaatga catgaagtcc ggtcagggtc agggtcagag gaggcagagg     3120
catcgtcaca cgaaagcaag ctctaataaa gcgcacagct cgtcgtaccc aagagtgcct     3180
tcgaggtcgt ccaacacgca gaggcccctg ctgtctgtgc agtccgaggg tgccaacatg     3240
acgacggcaa ggcaggctgc tgctgctggt gcttctctgc cgccggagcc ggaggaggca     3300
ggacggcggc ggcggcgaca acgcaaggca atagaagagg acgaggacaa ctcgagcgat     3360
gagtcggccg gggaagaggt gattgtcaga gtcgattctc ccagcatgct caccttccgt     3420
cagccctcca gcgctgctga tcgatga                                       3447

<210> SEQ ID NO 9
<211> LENGTH: 1596
<212> TYPE: DNA
<213> ORGANISM: Oryza sativa

<400> SEQUENCE: 9
atgaatcatt gtcttgtagt atcccacaaa aaactccaaa ctttccgcac atttgcagct       60
agcaagttct cttcttttac caaatctgca cagaagtcta taaaatactc cttccagttc     120
atctaccaaa acaatccact cttttgtccat gtagcttact ttgccctgat ctcctttgct     180
ggatatggat ctctaaaggt cctcaagcca cgagacaagt caaatactct gaaagacttg     240
gacgtgctat ttacttccgt atctgcatca actgtttcaa gcatggctac tgttgaaatg     300
gaggatttct caagcgctca actctgggtt ttgactattt taatgctgat tggtggtgag     360
gtattcactt caatgcttgg cattcacttt atgagagccg aatttggtac aaaagagtca     420
gtcagcacaa gggatcactc accttgcatt gatattgagt ctattacttc cacaaaattt     480
ggtcccagca cccagggcac aaaagttaca gtttcatttt ctgaactccg catggaaaat     540
ggaggacatg tagagcccaa gacgattaaa tttttaggtt ttgtagtgat gggatatctt     600
ctaataacaa acttaggcgg ctccctactt atttacctct accttaacct ggtaccaagt     660
gcacataaaa ttctaaagag aaaaggcatt gggatcatcg tattctcagt atttacagcc     720
atctcctcag ttggaaattg tggcttcact ccagtaaatg agaatatgat tatctttcag     780
aagaactcca ttcttctatt gctaattctt cctcagatac tagcaggaaa tacattattt     840
gcaccatgct tgagattaat ggtgtggtca cttgagaaga ttaccggaaa aaaggattgt     900
cgttacattc ttgaatatcc aaaggccatt ggatataaac atcttatgag taccagggaa     960
agtgtttatt tgactttaac agttgtgagc ttgatcattc tgcaaaccgt attgttcctc    1020
tctttggagt ggagctcggt agctttggat ggaatgagca actatcaaaa gatagtatcc    1080
gctctatttc agtcggtcaa tgctaggcat gcaggtgaat ctgttacaga tctgtcaaac    1140
ctctcttcag caatcctagt cctatacacc atcatgatgt atctccctgg ttacacttcg    1200
```

| | |
|---|---|
| tttttacccca gacatgatgg tgaggattct aagaccgaga agataaacaa aagaaaaggg | 1260 |
| ctattggaga actggatctt ctcacatatg tcttatttgg ctatctttgt aatgctaatt | 1320 |
| tgcatcacag aacgggactc gatggctaca gatccactta atttcaatgt tttcagcata | 1380 |
| ttgtttgaag tcgtcagtgc atatggaaat gtggggttct cggttggcta cagctgcaag | 1440 |
| aggctactga accatgatgc acgctgcaag gatgcctcgt acgggtttgc ggggaaatgg | 1500 |
| agcgacaatg ggaaagcgat cctgatcatc gtcatgcttt tcgggaggct taaaacgttt | 1560 |
| aacatgaagg gtggaagagc ctggaagctt agataa | 1596 |

<210> SEQ ID NO 10
<211> LENGTH: 1665
<212> TYPE: DNA
<213> ORGANISM: Oryza sativa

<400> SEQUENCE: 10

| | |
|---|---|
| atgagttctc tggatgccac tactcctaga tatgacgagt ttaaaaggat ctaccacctt | 60 |
| ttccttttcc atgcacaccc attctggctc aactgctgt acttcctctt catctccctc | 120 |
| ttgggtttct tgatgctgaa agctctgccg atgaagacca gcatggtgcc gaggcccatg | 180 |
| gacttggacc tgatcttcac gtcggtgtcg gcgacgacgt gtcgagcat ggtcgccgtc | 240 |
| gagatggagt ccttctccaa ctcccagctc ctcctcatca ccctcctcat gctgcttggt | 300 |
| ggtgaggtct tcaccagcat ccttggcctc tacttcacca cgccaagta ctcctccaag | 360 |
| atgatagcaa ccttacctga tgatgacgac catggtggca gtggcaaacc accaccacca | 420 |
| acgacgtcac cttcgtctac cctagtggag ctcgagctcg ctcctcccat ggacgtcgtc | 480 |
| gtcgtcaacc ctaccaccac tgcgacgacg cacgacgagg tagagctagg gttaggacgt | 540 |
| cggaacaagc gcggctgcac ctgcactact actcacacgt cgtcgtcatc atcggcatcg | 600 |
| aagacgacga cgacgaggct actgatgttc gtggtgatgg ggtaccacgc ggtggtgcac | 660 |
| gtcgccgggt acacggccat cgtcgtgtac ctcagcgccg tcggcggcgc gggggcggtg | 720 |
| gtcgccggga aggggatcag cgcgcacacg ttcgccatct tcaccgtcgt ctcgacgttc | 780 |
| gccaactgcg ggttcgtgcc gacgaacgaa gggatggtgt cgttcaggtc gttcccgggg | 840 |
| ctcctcctcc tcgtcatgcc gcacgtcctc ctcgggaaca cgctcttccc ggtcttcctc | 900 |
| aggctggcca tcgccgcgct cgagagggtc accgggtggc cggagctcgg cgagctcctg | 960 |
| atccggcggc ggaggggcgg cggcgagggc taccaccacc tgttgccgag ctcgcgcacg | 1020 |
| cggttcctgg ccctcaccgt ggccgtgctc gtggtggcgc agctggcgct ttctgcgcc | 1080 |
| atggagtggg gctccgacgg gctgcggggg ctcaccgcgg gccagaagct cgtcggcgcg | 1140 |
| ctcttcatgg cggtcaactc gaggcactcc ggtgagatgg tgctcgacct ctccaccgtg | 1200 |
| tcgtcggccg tcgtcgtgct ctacgtggtg atgatgtacc tgccaccttta caccactttc | 1260 |
| gtacctgtcc aagacaaaca ccagcaaacg ggagcacagt ccgggcagga gggcagcagc | 1320 |
| agcagcagca tatggcagaa gctgctcatg tcgccgctct cgtgcctagc catcttcatc | 1380 |
| gtcgtcatct gcatcacgga gcggcggcaa atcgccgacg accccatcaa ctacagcgtc | 1440 |
| ctcaacatcg tcgtcgaggt tatcagtgcg tatggcaatg tggggttcag cacggggtac | 1500 |
| agctgcgcga ggcaggtgag gcccgacggc agctgcagag acctgtgggt tggcttctca | 1560 |
| gggaagtgga gcaaacaagg gaagctcact ctccatggccg tcatgttcta cggcaggctc | 1620 |
| aagaagttca gcctgcacgg tggtcaggca tggaagatag aataa | 1665 |

```
<210> SEQ ID NO 11
<211> LENGTH: 24
<212> TYPE: DNA
<213> ORGANISM: Artificial sequence
<220> FEATURE:
<223> OTHER INFORMATION: Target sequence

<400> SEQUENCE: 11
gctctgcgcc tgcatcgtcc tcgg                                              24

<210> SEQ ID NO 12
<211> LENGTH: 24
<212> TYPE: DNA
<213> ORGANISM: Artificial sequence
<220> FEATURE:
<223> OTHER INFORMATION: Target sequence

<400> SEQUENCE: 12
gtccatcacc gcgctcatca tcgg                                              24

<210> SEQ ID NO 13
<211> LENGTH: 23
<212> TYPE: DNA
<213> ORGANISM: Artificial sequence
<220> FEATURE:
<223> OTHER INFORMATION: Target sequence

<400> SEQUENCE: 13
ggctgtcgtt ctgaaattct tgg                                               23

<210> SEQ ID NO 14
<211> LENGTH: 23
<212> TYPE: DNA
<213> ORGANISM: Artificial sequence
<220> FEATURE:
<223> OTHER INFORMATION: Target sequence

<400> SEQUENCE: 14
gagtttgcca gtgacagacc tgg                                               23

<210> SEQ ID NO 15
<211> LENGTH: 22
<212> TYPE: DNA
<213> ORGANISM: Artificial sequence
<220> FEATURE:
<223> OTHER INFORMATION: Target sequence

<400> SEQUENCE: 15
gtcgttcttt ttagcactat gg                                                22

<210> SEQ ID NO 16
<211> LENGTH: 23
<212> TYPE: DNA
<213> ORGANISM: Artificial sequence
<220> FEATURE:
<223> OTHER INFORMATION: Target sequence

<400> SEQUENCE: 16
gctaaaaaga acgacagtga tgg                                               23

<210> SEQ ID NO 17
<211> LENGTH: 24
<212> TYPE: DNA
<213> ORGANISM: Artificial sequence
<220> FEATURE:
<223> OTHER INFORMATION: Target sequence
```

<400> SEQUENCE: 17
gcaaaattga gcttatccca atgg                                              24

<210> SEQ ID NO 18
<211> LENGTH: 23
<212> TYPE: DNA
<213> ORGANISM: Artificial sequence
<220> FEATURE:
<223> OTHER INFORMATION: Target sequence

<400> SEQUENCE: 18
gcaatccagc aaatactcca agg                                               23

<210> SEQ ID NO 19
<211> LENGTH: 22
<212> TYPE: DNA
<213> ORGANISM: Artificial sequence
<220> FEATURE:
<223> OTHER INFORMATION: Target sequence

<400> SEQUENCE: 19
gcaatagata ttgtgaaaaa gg                                                22

<210> SEQ ID NO 20
<211> LENGTH: 23
<212> TYPE: DNA
<213> ORGANISM: Artificial sequence
<220> FEATURE:
<223> OTHER INFORMATION: Target sequence

<400> SEQUENCE: 20
ggacaccacc gacgcgtagt cgg                                               23

<210> SEQ ID NO 21
<211> LENGTH: 22
<212> TYPE: DNA
<213> ORGANISM: Artificial sequence
<220> FEATURE:
<223> OTHER INFORMATION: Target sequence

<400> SEQUENCE: 21
gaaacaagaa gctgcgctaa gg                                                22

<210> SEQ ID NO 22
<211> LENGTH: 24
<212> TYPE: DNA
<213> ORGANISM: Artificial sequence
<220> FEATURE:
<223> OTHER INFORMATION: Target sequence

<400> SEQUENCE: 22
gtttttgaca ttgattttta atgg                                              24

<210> SEQ ID NO 23
<211> LENGTH: 22
<212> TYPE: DNA
<213> ORGANISM: Artificial sequence
<220> FEATURE:
<223> OTHER INFORMATION: Target sequence

<400> SEQUENCE: 23
gcaccatgct tgagattaat gg                                                22

<210> SEQ ID NO 24
<211> LENGTH: 23

```
<212> TYPE: DNA
<213> ORGANISM: Artificial sequence
<220> FEATURE:
<223> OTHER INFORMATION: Target sequence

<400> SEQUENCE: 24
ggtgcacgtc gccgggtaca cgg                                              23

<210> SEQ ID NO 25
<211> LENGTH: 3068
<212> TYPE: DNA
<213> ORGANISM: Zea mays

<400> SEQUENCE: 25
cgcagctccc cacttctcat cgcccccttt ttttaatttg tggccatctt tggggtggtg      60
ggcggaggat ttctaactgg atggtgaagt ttgtctggcg aaaaggacgg ctgcgacgaa     120
cccgtccatc gatccaacgc tgtgcgcgcg ttggggagg gacctgccag gccccacctg     180
cagcgacaga ctattgatag atgccttcct ctctgatcac ctgatggctg atgccttcgc     240
ggccgtcttc gcctgccgct gctactacta gttgccttcc tcgcttcccc gtctcgcccc     300
agccgcttcc cccctcccct acccttcct tccccactcg cacttcccaa ccctggatcc      360
aaatcccaag ctatcccaga accgaaaccg aggcgcgcaa gccattatta gctggctagc     420
taggcctgta gctccgaaat catgaagcgc gagtaccaag acgccggcgg gagtggcggc     480
gacatgggct cctccaagga caagatgatg gcggcggcg cgggagcagg ggaacaggag      540
gaggaggacg tggatgagct gctggccgcg ctcgggtaca aggtgcgttc gtcggatatg     600
gcggacgtcg cgcagaagct ggagcagctc gagatggcca tggggatggg cggcgtgggc     660
ggcgccggcg ctaccgctga tgacgggttc gtgtcgcacc tcgccacgga caccgtgcac     720
tacaatccct ccgacctgtc gtcctgggtc gagagcatgc tgtccgagct caacgcgccc     780
ccagcgccgc tcccgcccgc gacgccggcc ccaaggctcg cgtccacatc gtccaccgtc     840
acaagtggcg ccgccgccgg tgctggctac ttcgatctcc cgcccgccgt ggactcgtcc     900
agcagtacct acgctctgaa gccgatcccc tcgccggtgg cggcgccgtc ggccgacccg     960
tccacggact cggcgcggga gcccaagcgg atgaggactg gcggcggcag cacgtcgtcc    1020
tcctcttcct cgtcgtcatc catggatggc ggtcgcacta ggagctccgt ggtcgaagct    1080
gcgccgccgg cgacgcaagc atccgcgcg gccaacgggc ccgcggtgcc ggtggtggtg     1140
gtggacacgc aggaggccgg gatccggctc gtgcacgcgc tgctggcgtg cgcggaggcc    1200
gtgcagcagg agaacttctc tgcggcggag gcgctggtca agcagatccc catgctggcc    1260
tcgtcgcagg gcggtgccat gcgcaaggtc gccgcctact tcggcgaggc gcttgcccgc    1320
cgcgtgtatc gcttccgccc gccaccggac agctccctcc tcgacgccgc cttcgccgac    1380
ctcttgcacg cgcacttcta cgagtcctgc ccctacctga agttcgccca cttcaccgcg    1440
aaccaggcca tcctcgaggc cttgccggc tgccgccgcg tccacgtcgt cgacttcggc     1500
atcaagcagg ggatgcagtg gccggctctt ctccaggccc tcgccctccg ccctggcggc    1560 ccccccgtcgt tccggctcac cggcgtcggg ccgccgcagc ccgacgagac cgacgccttg    1620
cagcaggtgg gctggaaact tgcccagttc gcgcacacca tccgcgtgga cttccagtac    1680
cgtggcctcg tcgcggccac gctcgccgac ctggagccgt tcatgctgca accggagggc    1740
gatgacacgg atgacgagcc cgaggtgatc gccgtgaact ccgtgttcga gctgcaccgg    1800
cttcttgcgc agcccggtgc cctcgagaag gtcctgggca cggtgcgcgc ggtgcggccg    1860
```

```
aggatcgtga ccgtggtcga gcaggaggcc aaccacaact ccggcacgtt cctcgaccgc    1920
ttcaccgagt cgctgcacta ctactccacc atgttcgatt ctctcgaggg cgccggcgcc    1980
ggctccggcc agtccaccga cgcctccccg ccgcggccg gcggcacgga ccaggtcatg      2040
tcggaggtgt acctcggccg gcagatctgc aacgtggtgg cgtgcgaggg gcggagcgc     2100 acggagcgcc acgagacgct gggccagtgg cgcagccgcc tcggcggctc cgggttcgcg    2160
cccgtgcacc tgggctccaa tgcctacaag caggcgagca cgctgctggc gctcttcgcc    2220
ggcggcgacg ggtacagggt ggaggagaag gacgggtgcc tgaccctggg gtggcatacg    2280
cgcccgctca tcgccacctc ggcgtggcgc gtcgccgccg ccgccgctcc gtgatcaggg    2340
aggggtggtt ggggcttctg gacgccgatc aaggcacacg tacgtcccct ggcatggcgc    2400
accctccctc gagctcgccg gcacgggtga agctagacgt cattgagcgc tgaatcgcag    2460
ttagcgaccg ggccaaggtt ctcgccggcg tgatgagatg gaacactttg actcccgcgg    2520
ccggatcggc ctgtgttcgt tcttgtttcc gatctccctt ctctttcccg ttgcttcgat    2580
cccgtcaagt atggtagacc gtagcctatt gttatgttta aatgtcaatt attatgtgta    2640
attcctccaa cgccgatat ccaataagga cgaaccggat tttcgttagc tcgacctcga     2700
atgagaattt tgtatacaat gcatcctcgt tagctatgtt catctgttcg aatgcttgtg    2760
ccctcatgtt ttcattccgt tcgtcctcta cacgaatggt gatcactatg tattgtgaac   2820
gagctcagtc atgtaggagc tgccagattg gaattcgcgg cttgctttgc ctttgaggag    2880
tatgaaaata ttatatgttt atctcacaag aactggtaag gtctgtttat ttcttttcct    2940
tgccgtgccc atcctgtaag aaatcctcca tggccgatgc ggaaacatct cgttgctttg    3000
ccttgcatgt atcccttcgc ctgtgtggcc gtcctctgcc ggggctgttc acgatctaaa    3060
aataaaaa                                                              3068

<210> SEQ ID NO 26
<211> LENGTH: 6746
<212> TYPE: DNA
<213> ORGANISM: Zea mays

<400> SEQUENCE: 26
atgaagctcc tctcgccggc ggccgcaccg tcgtcctcgc cgttgttccc tcctcgcatc      60
gtcgaaggta cgtgtacacc gtcgtcagca gctgctacct ccgcggcgcc ggccagccga    120
ggttccatga tgcctatcta tctatgtata gtacgtatat ggcgccgcgc caggcccttg    180
cccttgtcgt ctgcctgcat gcctactact acaagctact tccaaatttc gcattgtcct    240
cggcgctaca cggccggtgg gcaatcagac aaagaaacaa acgtgtaagc aagatgaaaa    300
attgtatttt tggggttcgga caagcaagtc gtcgtcgtcg tcttagggta gccacacaca    360
caggcagatg ggcaatcaga caaagaaaca aacataagca agatggagag aggcaggcag    420
gcagtcaggc gctgctgctg ctagtgctag ctccttgcttt gttgtgtgtc ctgatggtcg    480
agttcctcac cgctgctttt gcttttctgc tttcacttgc ctgcagctgc agctcgtcaa    540
tcaggtccat gccgtatccg catccgtatc cgtggcaaag cagcagcagc aggaggagga    600
ggaggcgcgg gcgcgacggg gccccgcggc agcctcaggc tcgccgggtg gtggagagcg    660
cagcagcagg ccccggccac ggcgacgaca acgcagcagc ctgacaacgt ctccagtgct    720
aaaggtgcta gcttgctcgt tatatttgat ttgactagtc tcatcatcca cccccagtc     780 acgtacacag atgctctctc tctctctctc tcttgaattg atgagcgaac gaaacactca    840
gacagatgct gtgccgtgct gcagtgcgcc cgtagcagca cagacactct gccgcacgca    900
```

```
cctgcgcttg tcgcttcccc tcttgctata tctcctgctg cttttgctaa agccggaaac    960
caaaaagaaa gttgagcttt tcgtcacaat tttgctttac ttattaagtg ctagtccgtt   1020
ttgtttatac gaccttacta ttagcttcta gcccggattc aaagtgctac agtgcgtttt   1080
cactaacaac atttaggatt atagcacatc aaatttgact agtgttacaa aaatatatat   1140
tagcatcata catatttagt taaagttaaa aatatttaat ttgtatgaaa acaagagtg    1200 acactctcta tgggataggc cgagtacgca ccatgcatga ttactactat taggctatct   1260
ccagcagcgt tacctattct accttctatt tcaaacttta cttcgtaaac agtataattt   1320
gtaatgcaaa acaatgtttt atacggtcat atacacggtt cgctagccac agcctaaggc   1380
caactccaat agactgttct gtactgcaga cgacaatgtt tacatagtaa agtttgaaat   1440
actgattgaa gtacgtagtt tgctggagat agcataagcc tccttgataa ggctctttca   1500
aaggctcctc caacaactcc ttaaaaaatc tatgaaacgg gggctattcc gctagcttct   1560
cgttgaaaat agcaaggagc tgcttccaag aaacgagcaa agtcggggc tcgaaaagag    1620 gcttctaagg ctccctccca tcctccattc ctcccctctc tcatgggttc catgttggct   1680
gaaggtgctg catttcgtac taaatagggt gctcatcccg aaacttttg tgaaaacaag    1740 aacatagcta ttttcacaca agagccaaaa ccagagttgg agttgttgac acaaaagtct   1800
aactaaaggc gggcaaacat gcatacctgg tattccgcgg tgtgttggtc ttgcatatat   1860
tcaattttcc tattaagttc acaatgttta catttatta tttactaggt aggtgctcgt     1920
gtatggttac cgtttctata tatcatatag gtagaccttg attaaatgtg atagttattt   1980
agacacagct gatccattta atattgttac gacctgatac gacactattt gaaataggcc   2040
catgttggac tagcccgcaa gtgccgatcc agcctgatac gattatatta agatatatat   2100
atttacaatg tatatccttg gtatataaga aatgtctttc ctataacaca aaagcagatg   2160
agttgtattg gccagcacct tccctctata aggcgcatgg tcgaggcgct gcagaggagg   2220
cacataggga gggaggatgc acaacgattt tgacacttag ggctagtttg acaactcaat   2280
ttttctaaca ccccgtttgg atcattggaa ttgaattcca ttctaataac agtaatttag   2340
gtatatatca attaagctaa ttcggtttta tgtaaaatat atttgtatac tattattatt   2400
aagatgtcgg agatatttat gtgctatatt tttagtatag aggagtgaga cgaatagggt   2460
catgtaattt acagagtaca aacaaattct actaatacat aaaatcattt tcaatcctcc   2520
accccatgaa ttcgaggtaa ccttatatct ggactttaga aaatggtgga atatcaaatt   2580
tcgagctaaa tatgttactt tattgaatga atttcaattc ctttaaaatg aagggattca   2640
aacggcccgc aagggaaaat aaactggttt cattggaaaa tggaaatttc ttcaaagaat   2700
gggattgcca aactagcctt taagtagta ggagatctat ttatttattt tgacaaaata    2760
tatgaaaaaa aggttttagc tccttcacga tcatcgatcg atgccttatc ggtgacggaa   2820
ggtggatcgc tatcaaccgt actgctgcaa acagtagttg actgcgaaat taagattctt   2880
gatgtgtgat tgattatgag gtaactgtcc acattgtcct ctttgtttct tgaccccaaa   2940
tccttggcga actttactca tcaatcacaa aggtatctct gtatgtgtgt ggtcagaggg   3000
atcctgtcct ccttgtaccc cactgttctt tttagctaat gcaaattgcc attggatcaa   3060
cttggtgatt tgatggata cagagatcaa atatccgatc aggaatatag tagatatggc    3120
actccaaggt agatagatga ttagactgga ccgcagaggt atcttcagtt tttttttgcc   3180
atgtaactcg cgcgcacagc agggaatctg attgtgtgtg taagggagat tttaagaac    3240
```

```
tggccatcta tcttctgttg ggagaaatga agtcaaaatg ggtaatgcag tgctgaatct    3300
gacgctctag ttgacgttac gctgctctgc tcaggccagc aggttcatgg tcctttgttg    3360
catgctgaac acttgctaga gatgcaattg ggtgccgaaa aataaaccaa cagtagctca    3420
atctgaccag tcacataatt ttcttcagtt ttcctccttt gagaaatgtt ttgttggagc    3480
tgggttttcc tgcagtgttc cagaccagcc gtgtggaaac cgagtccgaa attgcgaaat    3540
ggccagggaa accacaagac cttgaggatg agcaccaggt ggtccgtctt aggttgtttt    3600
cagttcacag atgcttgttg ctgaaattaa taaatcttcg tctgtaggct gaggaggcag    3660
agctgcagcc acttatcgac caggtgaggg cgatgctacg gtcgatgaac gacgggata    3720 ccagcgcctc ggcgtacgac acggcgtggg tggcgatggt gccgaaggtg gcggcgacg    3780 gcggcgccca gccccagttc ccggccaccg tgcgctggat cgtggaccac cagctgcccg    3840
acggctcctg gggcgactcg gccctgttct ccgcctacga ccgcatgatc aacaccctcg    3900
cctgcgtcgt cgcgctgacc aagtggtcgc tggagcccgc gaggtgcgag gcggggctct    3960
cgttcctgca cgagaacatg tggaggctag cggaggagga ggcggagtcg atgcccatcg    4020
gcttcgagat cgccttccct tctctcatcc agacggctag ggacctgggc gtcgtcgact    4080
tcccgtacgg acacccggcg ctgcagagca tatacgccaa cagggaagtc aagctgaagc    4140
ggatcccaag ggacatgatg cacagggtcc cgacgtccat cctgcacagc cttgaaggga    4200
tgcctgacct ggactggccg aggcttctga acctccagtc ctgcgacggc tccttcttgt    4260
tctctccttc ggctaccgct tacgcgctga tgcaaaccgg tgacaagaag tgcttcgaat    4320
acatcgacag gattgtcaaa aaattcaacg ggggaggtaa gccgatcgtc catgcatgga    4380
ggattaatta agacgatcga tgatgtttaa tccgtgtctc gtctcatcag actgtttgcc    4440
atcaccgttt cagtccccaa tgtttatccg gtcgatcttt tcgagcacat ctgggttgtg    4500
gatcggttgg agcgactcgg gatctcccgc tacttccaac gagagattga gcagtgcatg    4560
gactatgtga acaggttttt gcttctgcga tcgatcactc tttatgtgaa caggtttttt    4620
tatgacagat tgagtagatg aatttctttg acttgtcttg tcatttcgcg taggcactgg    4680
actgaagatg ggatttgctg ggctaggaaa tccaatgtga aggatgtgga tgacacagct    4740
atggctttcc gactactaag gctacatgga tacaatgtct ctccaagtat atataaacac    4800
cattcccttt ttagcttaaa catctcatta acttgttatt atatcttaat gacataagcc    4860
agccgtgttc tgtaggtgtg tttaagaact ttgagaaaga tggagagttc ttttgttttg    4920
tgggccaatc gactcaagcc gtcactggga tgtataacct caacagagcc tctcagataa    4980
gttttcaagg agaggatgta ttgcatcgtg ctagggtttt ctcgtatgag tttctgagac    5040
agagagaaga acaaggcatg atccgtgata aatggatcgt tgccaaggat ctacctggcg    5100
aggtaatcca aaccattcta ccatttgatg atcttagatc cattgaaaca tgcatgaata    5160
gaggcgaaaa ttagacggtg ttattttttt ggctttcatt tgttgatcg ataggtgcaa    5220 tatacactag acttcccttg gtatgcaagc ttgcctcgtg tagaggcaag aacctatcta    5280
gatcaatatg gtggtaaaga tgacgtttgg attggaaaga cactctacag gtgcacactt    5340
gtactccaaa aaaaaacgtt gatatacttc gttgcatact tattattagt gttttggca    5400 agaacctatc tagatcaata tgtaagagaa atgttctact tacatgtgcg gcgttttttgg    5460 caggatgcct cttgtgaata acgacacata tctagagttg gcaataaggg attcaaacca    5520
ttgccaagct ctgcatcagc ttgagtgtaa tgggctgcaa acgtgagcac catcatttca    5580
ttctccactt catgaatttt atgctggaag gttaactttg atttaattta caatatttc    5640
```

```
taaactatat tttaggtggt acaaggataa ttgccttgac gcttttggag tagaaccaca    5700
agatgtttta agatcttact ttttagctgc tgcttgcatt tttgaaccta gccgtgctgc    5760
tgagcggctt gcatgggcta aacgtcaat gattgccaat gccatttcta cacatcttcg     5820
tgacatttcg gaagacaaga agagattgga atgtttcgtg cactgtctct atgaagaaaa    5880
cgatgtatca tggtgagtac tgtaccttaa ttatatcagt taaccattat atatccattt    5940
aagaatcatc ttgaagcact tgtcatttac caagtagtag taacattggc atttgatttc    6000
ttaaacaaac aaataaataa attgggtaat agaacgaatg aatttcataa ttatatatag    6060
gaagatcaat aatgatattt taacaataag gatttatgta gttacgtaat ctttgttata    6120
tatactcatc gcagtgtaca tataaaagta aattgtacca aattgatctt tgatattcag    6180
aatatgcatt agcatttatt gcatgagtca atattgtgca ttagttacat atattacaaa    6240
agaggtaaag atgacgtcat attctttttt agcttccttt ttgtcaactc gtgtggactg    6300
attgtgcttt attctggtgg ccattatgtc atgccactta atttttttga tgtattatta    6360
tcgcctctta agttatgacc tcaatgaaaa cttgcataag ttcattgata tatactttag    6420
atattttata tcgatgttgt aattttttaac tcgcatttta caccgacctc ttttatttta    6480
gctgttttat ttaacatgtg tattctattt tcatcgtgtc atatattatg taatatatga    6540
aattgagaga atattatttt cctgacataa atgataaatt caggcttaaa cgaaatccta    6600
atgatgttat tcttgagagg gcacttcgaa gattaattaa cttattagca caagaagcat    6660
tgccaattca tgaaggacaa agattcatac acagtctatt gagtcttgca gtaagttatc    6720
cccacttgta cttaattaga ttataa                                         6746
```

<210> SEQ ID NO 27
<211> LENGTH: 1131
<212> TYPE: DNA
<213> ORGANISM: Zea mays

<400> SEQUENCE: 27

```
atgtttcctt tctgtgattc ctcaagcccc atggacttac cgctttacca acaactgcag     60
ctaagcccgt cttccccaaa gacggaccaa tccagcagct tctactgcta cccatgctcc    120
cctcccttcg ccgccgccga cgccagcttt ccctcagct accagatcgg tagtgccgcg     180
gccgccgacg ccaccctcc acaagccgtg atcaactcgc cggacctgcc ggtgcaggcg    240
ctgatggacc acgcgccggc gccggctaca gagctgggcg cctgcgccag tggtgcagaa    300
ggatccggcg ccagcctcga cagggcggct gccgcggcga ggaaagaccg gcacagcaag    360
atatgcaccg ccggcgggat gagggaccgc cggatgcggc tctcccttga cgtcgcgcgc    420
aaattcttcg cgctgcagga catgcttggc ttcgacaagg caagcaagac ggtacagtgg    480
ctcctcaaca cgtccaagtc cgccatccag gagatcatgg ccgacgacgc gtcttcggag    540
tgcgtggagg acggctccag cagcctctcc gtcgacggca gcacaaccc ggcagagcag     600 ctgggaggag gaggagatca gaagcccaag ggtaattgcc gcggcgaggg gaagaagccg    660
gccaaggcaa gtaaagcggc ggccacccccg aagccgccaa gaaatcggc caataacgca    720 caccaggtcc ccgacaagga gacgagggcg aaagcgaggg agagggcgag ggagcggacc    780
aaggagaagc accggatgcg ctgggtaaag cttgcttcag caattgacgt ggaggcggcg    840
gctgcctcgg ggccgagcga caggccgagc tcgaacaatt tgagccacca ctcatcgttg    900
tccatgaaca tgccgtgtgc tgccgctgaa ttggaggaga gggagaggtg ttcatcagct    960
```

```
ctcagcaata gatcagcagg taggatgcaa gaaatcacag gggcgagcga cgtggtcctg    1020
ggctttggca acggaggagg aggatacggc gacggcggcg gcaactacta ctgccaagag    1080
caatgggaac tcggtggagt cgtctttcag cagaactcac gcttctactg a             1131

<210> SEQ ID NO 28
<211> LENGTH: 6626
<212> TYPE: DNA
<213> ORGANISM: Zea mays
<220> FEATURE:
<221> NAME/KEY: misc_feature
<222> LOCATION: (2678)..(2777)
<223> OTHER INFORMATION: n is a, c, g, or t

<400> SEQUENCE: 28
atggtgaggc atctttaggt ttatttcacg cgcgcgcagc gcaccattat tagtcgtttt      60
cagctcgggc tcggatttaa tttgcgtgta tatatggtag gaggcgtacc acgagatgct     120
ggtgaagttc agggaggagc tgacgaggcc gctgcaggag gcgatggagt tcatgcgaag     180
ggtggagtcg cagctgaact cgcttttcat ctccggaagg tcgctgcgca acatcctttc     240
atctggtact gaagttgctg cggcccatgc ccctcttatt ttatattaga tgatttcttg     300
gatcggttgt cgcctcatgc agcgatgcat gccctccctc ttgttaaaat cttcctgtcc     360
tctccttcgt cttgctgtcc tcttctcttg ttgagcatat gttgatgggt ttttttttt      420 gcatttcaaa agggttaaat ttttccttga tgtggtttct cagcaattaa ttttggcatc     480
tgtgtagttc ccttttttaag agcatcttgc tatgcatgca tattttgagt atagatagct    540
gcggaacgca gatgaatgtc ttgtctgcgc ttcatgtttt taatgcgcg gcagcattcc      600 taatcagggg tttcgaaaga gaatcttctc cctgcttgct tttcctggcc atgcatctgt     660
gagattcttc tctctggctt ccgtcgatct ttgcttctgc tggaaaggaa atagtcctca     720
gtcacacatg tgcaggagcg cagcttcaat ctagcatggc tgaaagctct ctggttcttt     780
ccatacactc catcctgcac attccttgca tatattctgc tgttaaactg cttagcgacg     840
aggatgaatg aaaacaccctg tctttttttac tagtgggagt actaatttgg ctgctgttgc    900
catggatgcg ttgttcatcg tcctccatta tattgatcga ttccatttgg aatggaacat     960
gtgcatgtgt tctgcgagta gttcctggct cagcgcagcc atctttttcc atgatgggaa    1020 ccccaggag ttcccttgtt ctagggtttg ggaaagggcc acagtgtact gggtgctgtg    1080
gcattgtgca agcacagtct atagccgagg agtctcactg gcgtatgtca gtgaaacata    1140
gtagtataca cgttgtagta gtgggagatc agagagagag agagatgggg agtcatcccc    1200
catctgtcac gcaagcttgt ggccagaaca ttcttgtcat ctttctcccc ctcaagagat    1260
gtagctacct gttgtcctag aatctatagt gttgtggtgt ggtcttccag gtgcgcacac    1320
agatctggcc actgctggcc ttagtatttg ctaattttaa aatgaacaca tcaggtagat    1380
cgagacgatc catggcaagc gtcttttctaa tgacctatca caaggctata gtaacaactc    1440
gtaccaccac agttacgcac agcccagagt ttttcacttc tcggttctgt tcttcttaga    1500
gcactggcta tggctagtat atatgcatgg cagcaacaca cacacacaca cacaatcact    1560
tcattactgg agcaagttag cgaagaagct gccatctgat gtcgtagaat gctgcaaaaa    1620
tgaaaggttc agaggcaggc atacggggttg aaatggagca ccgtatgcgg cggcccagtt    1680
ttttgtgttc tgaccggcgc agtggacaaa atggcctgtg tgcctcgaga accatagaga    1740
cagttgccta gcgcatgagc gctgagcggc cctattatt tgatgtgaga tctctctatc    1800
aatggatgtg tgatctgcta ggtttatatt atatatgcgt ctactatatc cctaccagtc    1860
```

```
cctgtatttt ctgacagata gacttctccc ccgcgcgttc tctcataaat aaatgacggt    1920
caaggaacat tggatgcttt ccgaggcgag ctagtacaag tttcatctgc gtttgcgttt    1980
gtatttttca gctgtcaact cagatttctc ctcagctcca actgttcttt gaccttcttg    2040
gtactgtttt cttggaagaa actatttgtt gaccattttt ggttataata aggccacaga    2100
caaactgttg aatttaatca caaaacaaca ctactgcgtt ttttcttttc ttttctgact    2160
gatgttgcac atgtactcca agattcttgg ttgcatgcac tctttcaagg tcatgcaaaa    2220
gcaaggacac cgggtgtcac gagtttccgt ttgtctcgag gtaagaccaa aaaagatacc    2280
ggaagcaaac aacataaaac aaagggtagg atggaaaaga gctgatggat tttacaatgt    2340
atcgccagag tggaaaagac aacgcgacta gaggaaagga acgatctggc acttccaact    2400
gtgtgaattc ttccatttga tgtgcgtctc gtgcatgttt attttcttgg ttactggaaa    2460
tcgggtgcat ccatttttat tcaggattca attattggtt actggagcca ggtccgttcg    2520
tttttatttt ccttttgaga ttgactggat cgattctctg gttctagtca cttatgctgt    2580
tggttttatc gttttcatgg atttcgattc tatctctccc aatattcagt aaacataaaa    2640
gcctgtgact atatttcttt tttttctaat tcttgtannn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnntcg ttttcaatgg atttctattc tatctttcc catattcagt    2820 atcacataaa atcctgtgac tagatttctt tatcacatac aatcttgttt ttttattttc    2880
tttaatttaa cactggattt gtttgataat atgttctgaa aaacgttaat aaatttaagc    2940
acaacagcct tttaaaaata tgtataatta tttaccttga aacccagcat cggccgggaa    3000
caaggaaaag aactcaaggt tttaaatgca ttgaaatgaa acattaatgg agtgtttggt    3060
ttgaataatg atgtagtcca tcatcttctc actcctcact ttttttgtttg gtttatggaa    3120 tggagtgagt taatccatca acacctcatt cctcatagtt agttgtttag tactaatatg    3180
tggaatgaag tcatcccacc aaatttgaag aatggactca tgatgcacca cttcatttta    3240
gatagagtga ttcatcaaac caaacacctc ataagggcat gtttggatcc taggagctaa    3300
aagaaaagtg actaaagttt agtcactta ggagctaaag atctactaaa taggaaacta    3360
aaagtgacta gaatagtaaa aggtatcttt ttagtcattt ttagctccta agaaggagct    3420 aaatttagt tagtttggtt tagctcttgg atccaaacag gccctaagaa aatgtttcga    3480
caacatttgg gacaataaaa cagttcctaa ggatttcttt ggcaagatta ggccttcttt    3540
ggaacaaaga aaaatgaagg aatcttgaag gattgaaatc ctataggaag cttccatatg    3600
caaagaattg tgttcctagg atgatttcta acaagaggct catccccttg aaaattgttc    3660
tttgtgtcta tctctctcct ctaattcatg tgttcttatg ttgcattgaa acactattag    3720
aaaattttca tgtgttttaa tttatgtatg attgtaagtg tcaagcagca ctattcctac    3780 atttttttcta ttcctgtgtt ttatcgatac tgcatcccaa tgaaggccta agcgtatcat    3840
gcaatctttt ccagaagttt tttagattgc tgtataatga caaggtgcaa tgctcttcgt    3900
tttctttttt ggttttcctc atttttcagca aggccaccaa attttttccat gatgttcttg    3960 tcttattcct gtagtatccc tcgaaaaaat ttcatagctt tctacatcca tgttatctaa    4020
tgatgttctt catttcaaag acagacacat ttggcataag ttctgattgg tcactaaaac    4080
tttgtggtac ggtcatttac ttttactata cacatgtact gtattcatgc gtacattgta    4140
ctttgtccat tggggccttt cctctttta atacaacggg catcgtttca aaaaaatgt    4200
```

```
gtcagtcgta actgcacact tctttagttt tccccagtta acagcatgac ggaatagagt    4260
tacagagtct catgtcaagt cacatatatc ctcaagtcgt ttctaaaatt aaagtaatat    4320
tttcattgtt gcttccgtaa gaatgcacca caaacacaaa atatcatttc ctttatgcaa    4380
atatatatat atgaatgttt gtttctggca gtggtgagaa gcttctcact gagccaaagg    4440
ttttagggat gccatgtgct cttttctctt tttaagtgta gattaagcaa acctttataa    4500
tttttaaact ccaaccagat acctttccta aattcataaa tgctctggac tatcttcacg    4560
aaaaaggctt tggtaatatg ttcacaagcc tcctttatct gttatcctgg gctagacata    4620
ggatgtgttg aagcaataca agcggagttg tttcgttaaa gcaaaaaaaa aactgtaact    4680
ttatattgga gaatatacat cgttctccca tatttgttac agtgctcata aatagacaaa    4740 gtttttttt tgaaatctta agccctgtgt ttctttggtt atcttatctc tatattgctt    4800
ccaaatatgt tgtcatcaag atggatatag ataattgtca aaacgaaaag tgtgcatggt    4860
tcatttatgc caattctgaa aagcataagt taaatattaa ataccaata aagaaaaaca    4920 tatgcagtgt tgactgttgg gaaaagaaca aggtctgcac atacacttgc aatataaatc    4980
tttttaccca gcaataaaaa aacgatcaaa tatcacgcaa acaaagtaat acgtccagaa    5040
acacccatac ttttgaaatt cgtctttgaa atgcagtagg ttcacaaaat aaaatggtgc    5100
aactgcacat gtcctttata tctgtactca atgggttttc tggagatgtt agattgattg    5160
gtgggacaat atcctaatgc aactcgcaaa ttcccaaggc cgaactcaag tgggagtttg    5220
gatgattttt tttgtaaaga agcagatggc tgcgctagtt tacatagacc atcacacttc    5280
acaattcaca ttcatgaagt cataactttg ttcacttctt gtttaactat ggcatataaa    5340
aacatactgt gtgttgtttt gcttgtatgg aacatgtatt ttagtttttt agtaaataag    5400
ttcagtaaat gtctttgccg gacaaatttc accaatctgg ctacgaatga tgcttgatca    5460
cttcttttgt tttatctaaa agttccatgt cttatgcttg aaggctcttc tgaggaggat    5520
caagaaggta gcggaggaga gaccgagctc cctgaagttg atgcacatgg tgtggaccaa    5580
gagctgaagc accatctcct gaagaaatac agtggctatc taagctcgct caagcaagaa    5640
ctgtcaaaga agaagaagaa agggaagctc cccaaggagg ctcgccagca gctccttagc    5700
tggtgggatc agcactacaa atggccttac ccctcagtac gtcttctttt tattcttcca    5760
ttttaactat tgttggtgac acatgattta gacgatgcca attcttcatg aacttttcat    5820
agccagctac ccaatgttag tactgactgc acattgtaat tcaagggtaa gtatatatat    5880
acataaatca catttggcaa atctaagcta catatgggtc tttgatcttc catgacggtc    5940
tgttgatctc tgatttgcat atcggcatat aaaaagtgag ccaaaatatg tcagagtcta    6000
ataatattga tcagggagtg gcaggtgatt attggtatta atttaacctt atttaaggta    6060
ttttgaaact tctgtagcgt tcttactaaa taccattgat tttaatttaa gcaactatat    6120
atttatctgg tgaaaaatga agccttttct gatatacaaa ttgaagagtc tacaatggtt    6180
tcacttacat ggctgaaaca gaaaatcata gtgccctgaa ttgtgtgttg atactcataa    6240
gcgcagattc aaatttgtaa ttttcaagtt tagggttcta agtgaaaaaa aaacattgag    6300
tccaggagca tacactgaac tttttttttta tcatatcttc attttgttgg atgttttgta    6360
tacggcatat agcctgtgct tccctactgg atatgaatta ccaactctt cccatcggtg    6420 agcaggagac tcagaaggtg gcactggctg agtctaccgg gcttgacctg aagcagatca    6480
acaactggtt catcaaccag cggaagcggc actggaagcc atccgaggag atgcaccacc    6540
tgatgatgga cgggtaccac accaccaatg ccttctacat ggacggccac ttcatcaacg    6600
```

```
acggcgggct gtaccggctc ggctag                                    6626
```

<210> SEQ ID NO 29
<211> LENGTH: 1703
<212> TYPE: DNA
<213> ORGANISM: Zea mays

<400> SEQUENCE: 29

```
atggtgctgg atctcaatgt agcgtcgccg gcggactcgg gcacgtcgag ctcgtccgtc    60
ctcaactccg cggacggcgg cttccggttc ggcctgctcg ggagccccgt cgacgacgac   120
gactgctccg gtgagatggc gcctggcgcg tccacggggt tcatgacgcg gcagctcttc   180
ccgtccccga ccccgccggc cgagccggag ccggagccgg tggcggcgcc ggtgccggtg   240
tggcagccgc agcgcgccga ggatctcggc atggcccaga ggccggtggc gccagcgaag   300
aagaccaggc gcgggcctag gtcgcggagc tcgcagtaca ggggcgtcac cttctacagg   360
aggacgggcc gctgggaatc gcacatctgg tactcagcct ctgacctcgt ctgcacccct   420
cgtaattacc atctactact gtgctaatct atggctcttg acgacttcca tttcctcctc   480
ctcctttcgc tgctgctcct gcttgatttg agcagggatt gcgggaagca agtctaccta   540
ggtgagtgcc tgagctcccc gcgttcgagc tccagcatct actatgaact gtcggttagt   600
tttactgcgc ttgatttggt tgccatctgc tgatgccctt actacccagg tggttttgac   660
actgcgcacg cagccgcgag gttagggagc gtttgcttgt ttgaattcgc gtccatttgc   720
atttctgtga tcgataggcg cgttgacacg gtcaagtttg gatcaagcag ggcatacgat   780
cgagctgcga tcaagttccg cggcctcgac gctgacatca acttcagtct gagcgactac   840
gaggatgatt tgaagcaggt aatagttgca cgaaaacatc aaatggcatc tccggttgct   900
ccatgagatc catagtttcg ttgtggactg gtgatgatgg gtgtgctttc cagatgagga   960
attggaccaa ggaggagttc gtgcacatac tccggcgcca gagcacgggg ttcgcgaggg  1020
gaagctccaa gtaccgtggc gtgacgctgc acaagtgcgg ccgctgggaa gctaggatgg  1080
ggcaacttct tggcaagaag taagctggca caggcagtag aaaaactgac ctgcatacat  1140
agtagcacct tttatactct gttagcttca gttcaattat ttctatgcat gggtatgagc  1200
aaaaggcgct gggacgaagt tggcttgatt tcacattttg acacgagggt ggtcaatgat  1260
taattcgaca taatttaagc tcatgttagg caagcctgag ggtgatttta aggaatacgt  1320
acaacaagct ggtgctcgct ggggtcagtg tgcttgttgt ctagtatgct aatagtggtt  1380
agcacgtctc tgttatattg gtggaagctg cacttccttc caccactcaa tgttttgcca  1440
tggcacctaa cgatgtcata cagatctatt tgcagcaacc actagatttc agatatgagc  1500
atttgcagac aatgcacccc ccctgcactc cgtagtctag gaccagtttt gtcaaaacct  1560
accagcgtag gcatccttct ggtgagacag agagtatctc acaactcgaa ttcacatgca  1620
ggtacatcta tcttgggctc tttgacagcg aagttgaggc ggcaaggtgc cactgtagct  1680
gccttccacg tctcattttc taa                                          1703
```

<210> SEQ ID NO 30
<211> LENGTH: 3921
<212> TYPE: DNA
<213> ORGANISM: Zea mays

<400> SEQUENCE: 30

```
caaacaggtt gtgattgaca tatggacccc caacatgtga gcatgtgtat ctcttttgtc    60
```

-continued

```
tctctttttcc gcatgtacgg tgagagagaa ccaagaaaga gagataaaat agatacatag        120
gctaaaatgt ggggttcata tgtcaaccac gacgcgtttc gacctaacta agaccggaac        180
aacaattaag gaccagactg acacacttta aaagtttatg gaccgagtta acatataacg        240
tcatataagt tgaagtaatg aaaatgtatt ttactcttag gatatatcat cacaggagcg        300
gtacaccgtc gggttttttt tttggaggat ggggacaac tatcacgagg gatacaatac         360
aacttagtaa ggccgcgagg taacaaacta acaagtggcc catcgaaaca gtaaattgtt        420
tcccggcccg ctcggccgaa caagtgacgt ccccattcta aatctaagcc cacttctgac        480
taaccacaac gcaacgaaca aagcgacaac atgagaggca gacgaaggcc gccttccact        540
tttcgatggc gccatggaac agcctgaact gcgatgtgag acgtacggcg ccgcgccggt        600
gcaggcacac atcgacgacg cagctagaac atcggggcg ggggaggcc ggcggcggcg          660 tgggcgtggc tccccgtgc ctggtggcag agctggcgca acctggtggg cacgtaccag         720
atggtgaggc gcgggtgcgc ggagaagacg gcgtcgatgt cgaagccgtg gcgcgcggcg       780
atctcgacga gcggcgcgta gcaggcctgc ctccaggcac cgacgttctc gccacgggcc       840
ttgtacgccc ggcgcagcgc gttggaggcc tcctcgtcca ggcagtgcag cgcgtagcag      900
tgcacgtagt gccgcatctt gggcttgttg atgtagctcg cgccgcactt cttggcgtac       960
cggaacacct ggttggtcac ctgcagtgca agcaaaaaaa aaaaaggttc atcagccacg      1020
gtcgattggt tccggtgtcg tgaaactggc cggtgtggtc gggtgcgcct ggcgcggacg       1080
caggagcagc gcatcgatgc agccgtccag gtcaggaag ctatcatcat atccaatcag       1140
ccctggaatc cggacaggcc aggccgtgca ttcatttcac tgcgggcgag cacgcgagtc       1200
gcgactactc gtacgccggc caaactgcca aaagcgagct cacatggctc gtactggtac       1260
gcgcgaaacc ggtggcaaca gcacacaggc cacggactcc gagaggagag ggcgtccatg      1320
catgcctatc tgtatctgag gcctggggcc ggccggacaa gacaacacaa gctgcacagg      1380 cttggcagc ctaccgatga ctgacacgtc gcgccttttt ccaggtcatc tacgtgcgtg        1440
tgcggctgta gcaaaatata cttgagtaca cgtacgtaga agtacttgac tacagactac      1500
tacggcgtac tatatagacc atctttttgca catgtgctac tgtagacgta cttacgtac      1560 acaaaatata atagaattcc actgcaaagg atttccttct tccttctagg tgatgtgaag      1620
ggccttttgc atgccactag atcttttttta ctatgactat gatgttatta caatgaatag     1680
tatctgtatt tctaggattt gtgaaagttg aactagacta actttgatca aatttactat      1740
agcaaatagt attggtaatt ataccaac tagatatact tcattattat tctaacaatg        1800
tgcttattta acatcataaa tgttagtatt tttatatata actttagtca acccttaaac      1860
cgtttcacta ctaacaaagt tgagaattac gtcttcgtat taaattatta atagagttct      1920 gaccctaac ttgtgtgact ccaactgtgt ctgagaatat ataacacatg ttttagagca       1980
aattataaac agtacctagc ttgtcaacga cctaaaaagt ttgtttcatt acattacgtt      2040
ttttaacact acagtttttg tttgtttatc gtacattcaa tctagctatc cgtatgcacc      2100
accaaatgga tttatacata tgtaatataa aaacgttgcc ctgctaaatt aataataagt      2160
gtgcgtacct tggtagggga cttgtggccg cccagcttag caagggactg cacctgcagc     2220
aggaagacgc ggcactgctc gtacagatgg aagaggtagt caagcccgtt cttcttggcc      2280
ctggccacct cgccgggctc tgtgaccacg aagggggtgct cccgctgcct ctccccgccg    2340
ccggagccga cagcggaaga ctccgtcgag tctgacccgc cgccgccgcc gtcctcgtct      2400
ccgtcgttct cgtcgtccag cacgtccaac ggcctcagct ccttcttcct cctcgccttc      2460
```

```
ttgcccttcc tcgcgccaac ccctttcttg cccttcttct tgccggccgt caccatcctc    2520
ctgccggcct cgccttccgc caagccgccg ctggccgcgg cgtcgcgctc gtcggacagc    2580
actgccagtt gcgatatgat tgaacaagaa caaataacat cacaggccgg caagcagaac    2640
tcaactcaac atgactgaat catgggcact gtccgcatgc atgcacgagt gcacgaccac    2700
agaggcaaac aatttgacca tgctgtgtat accttcttgt gacgcggcgt ccaatgtgct    2760
cccggtgtgg aagcggccgc cgagggacat gacacgcccg cgctcggccc gcagcgcggc    2820
gcggaggccg aagcgctcgc cgaggagcac gtcccagcgg aacagccccg cgagcgcggc    2880
catcatgtcg tcgagctcgc gctccgtcat gccgaggagc gtgctggccg tgaacccgag    2940
ctccgagatc cgcgccaccg tggacgggcg cacgccgtag ccggccacca ggtcctccag    3000
ctccctcggc gcgctcagca gcggcgcgtg gggcagcagc tgcggcgcgg gcggcggtgg    3060
gggcggaggc gcgggcgcgg cgggcgccgg cgggcccagg tcccaccgga acgggtgcgc    3120
cgccgagaag gcgtcgttgg gatccatgct ctcgactctc gagggttgcc aacctaactc    3180
gtgctccttg actccgtgtt gctgttgcct gccgccttgc cgtgcgctgg atcctgttat    3240
atagcggcaa ctgtttttt tttttttttt tgcaatgcaa tgcgaggccc gtggacttgc    3300
gagacgcact gcactgtagt cctagtctac tagcgcttgg tgtttgtcgg ctgctccaag    3360
cgagcgtgct ctgctacgac gtgaaaacga ctagtcctgt agaaagctgc accgcaccgt    3420
cgtcgtcgct cgcccctcgc gatttgatag tctagattct acgcgcccta cattacgtgc    3480
tggaacataa aaagaagaca cggcgaggct gataaatact cccacaccac ctgcattgcc    3540
cagtcccgtc gcggcgttcg tgtcgtggat gtgtcccgtt gcacgtctcg gtggctaggc    3600 tttcttttc ttccagctcc gtctgaaatc tatggggagt actgtacgtg aggcgacgtg    3660
gatttcagag ctcaccgtgg ataaggatac ttagggttca tggttcaaga ggtgcggtgg    3720
ccgttgcttg aacggcggtg ccgactgcag gcgaagcgaa gagtggattt tggagtacaa    3780
accggacgtc tctgctgttg cacgggacgt ttggcaatgg cacggattcg agaccagact    3840
tcacaagctg cttctcagct ttcaatcagc cacagccaga cagcgtgccc acgagcacga    3900
ccagcttcac gggccagatc c                                              3921

<210> SEQ ID NO 31
<211> LENGTH: 3793
<212> TYPE: DNA
<213> ORGANISM: Zea mays

<400> SEQUENCE: 31
acaggaacag gactagtcgt tttcacgtcg taacagagca cgctcccgcg tcgatagatc     60
gctacgagca gtcgacagac acggcagcat aaatgcgcgc gcaaaagcta gtagtaggac    120
taggcctaca gtgcagtgcg tccccgagat tcattcgtca agttcaggtc gaccggccgg    180
ccttgccctt gcattggaaa acagttaccg ctatataaca aacagccgcg cgcacggcg    240 agccaagccc gtcaaggcac gaggactgca ggagcagaaa gttggcaacc ctttgagttc    300
ctcactcaca cgcgcgcgag ccgagagagc atggatccca cgacgccttt ctcggcggcg    360
cacccgttcc ggtgggacct cggccgcgcg gcgcacgccg cgcccgcgcc cgcgcctccg    420
cctccgccgc tagcaccgct gctgctgccg cctcacgcgc gcgggagct ggaggacctg    480 gtgggccgga tacggcgtgc gcccgtccac ggtggcgcgg atctcggagc tcgggttcac    540
ggcgagcacg ctcctcggca tgacggagcg cgagctggac gacatgatgg ccgcgctcgc    600
```

```
ggggctgttc cgctgggacg tgctcctcgg cgagcgcttc ggcctccgcg ccgcgctgcg    660
cgccgagcgc ggccgcgtca tgtccctcgg cgcccgctgc ttccacgccg ggagcacctt    720
ggatgccgcg tcacaagaag gtacggcgta taggagtatg tactcgtgtc acacacatac    780
agacatactt gtatatatgc tcagtttttct tctgtagttc tgtactagtt ctgtgtgttt    840
tgcctctgcg agcaatgtga tgtgatgatg tggtcgctgg tcgatggtcg tgtgcatcgt    900
gcctgcgtta atgcatgcat gcatgcggac agtgtccatg catcagtctt tgttgggact    960
agagtcacgc gctctgctct gctcgcctgt gatgttactt gctcttgttc gatcataccg   1020
caaactcgca gcgctgtccg acgagcgcga cgccgcggcc agcggcggcg gcatggcaga   1080
aggcgaggcc ggcaggagga tggtgacgac gaccgccggc aagaagggca agaaaggggt   1140
cgttggcacg aggaagggca agaaggcgag gaggaagaag gagctgaggc cgctgaacgt   1200
gctggacgac gagaacgacg gggacgagta cggcggcggg tcggagtcga ccgagtcgtc   1260
cgcgggaggc tccggggaga ggcagcggga gcacccgttc gtggtcaccg agcccggcga   1320
ggtggcgagg ccaagaagaa acgggctcga ctacctcttc cacctgtacg agcagtgccg   1380
cgtcttcctg ctccaggtgc agtccatcgc taagctgggc ggccacaaat cccctaccaa   1440
ggtacgcgcg cgcacacact taggggggtgt ttggttacac cccgctaaaa tttagctcat   1500
gtcccatcga atgtttaaac ctccgttccg gatattaaat gtagtcggat tataaaacta   1560
atttgtcagc cgaagattaa aagacgagac gaatctagtc cagttgattg ggtctatatt   1620
tcatactcct atttaaaagt caaacgcttg atgtgacccg agctaaactt tagcaggagc   1680
aaccaaacac ccccttattc atttagcaga gtaacatttt tacatataat atacaaacgg   1740
cagacgtttt ctgtatacga acaactgtcg tgaatgtacc aatctttttta ggtcgttgac   1800
aagctataac aatataatgg taaagaaaat atagtggcac gcaaagcgcc aaagcccgct   1860
ctcattacct aggactagga ggaaggaagc agcaaaccct ttgtagtgga attctatatt   1920
tcctgcgccg ttaagtctat gctagtacat gtactacatc accatagtat atgcgggtcc   1980
tcaattcaag tactcgtaat gatcgtgtag cacttgtaca tacgtactgc tttaaagtat   2040
attttgcttg agacgcaccc gcactcgtgg ataaagcgag tgacgtgtca tcagtcgtcg   2100
gtgccaaagc ctggggtggc tttgtgtcgt cttgtccggc cctagggtca gacgggcatg   2160
catggcatcg acactctctc ggagtccgtg gctgtgtgct gttgccaccg gtttcgcgcg   2220
taccagtacg actgtacgag ccacgtgggc tcgatttgtg gcagtttggt ggccggcgta   2280
cgagtagtct cgtgctcgcc cccagtcttc agacggtgtg cgtcgaagtg aaatgaatgc   2340
acggtctggc ctggacggat tccagggtga ttggatatga tgatagcttg gtgacctact   2400
gacctgaccc ggacggccgc atcgatgcgc tcctgcgtct gcgtctgcgc caggctagcc   2460
cacccagatc cagaccgaga ccggccaggc gcgcgcagct tgttcgatcc gtgagcagct   2520
gctgctgctg ctgctgcgtg cgcacttgtg cgcgacgcga cacgacacga gcagcgagct   2580
gctctgcact gcactgcacg ggaaccaacc aaccatggct gatgagcgac atgttcgcgt   2640
ggcgcgcgcg atcgtgctcg tgctttgctt gcaggtgacc aaccaggtgt tccggtacgc   2700
gaacaagtgc ggggcgagct acatcaacaa gcccaagatg cggcactacg tgcactgcta   2760
cgcgctgcac tgcctggacg aggaggcctc caacgcgctg cgccgggcgt acaagtcccg   2820
cggcgagaac gtgggcgcct ggaggcaggc ctgctacgcg ccgctcgtcg agatcgccgc   2880
gcgccacggc ttcgacattg acgccgtctt cgccgcgcac ccgcgcctcg ccgtctggta   2940
cgtgcccacc aggctgcgcc agctctgcca ccaggcgcgg gggagccacg cccacgctgc   3000
```

```
cgccggactc ccgccgcccc cgatgttcta gcgtgcgtcg tcgatgtgtg cctgcaccgt    3060
cgccgtacgt ctcacagttc cttttctttt tagagtgtga accaccatgg aaaattggat    3120
tccctctcat atgatgttgc cacttctcag ttctcacttg tatgttgcgt tgcccggtta    3180
tagtcaggag tgggcttaga tttaggcact gtttagtttt aggactaaaa gctaaaaacc    3240
aaaccaaacc aaatgtttcc ggaagtaact ttttttaaa aaacgactttt ctcgcagtcc    3300 aaactgaaaa catggacctg cttttagcgg ctttcggatg gaaatgtgaa aacatatatc    3360
aaaaaaattt aacatatatt agtggtttcc accaaacggt ttttagttct ttaacggctc    3420
acaatccata atagttttt catagtcaca accaaccaaa cagaacctaa attgcgcttg    3480
atacgccatg tttggactgt taggatttat gggcttggcc caattaagaa tttctaataa    3540
ttcgaggaaa atctcaaaag cccatataag tggatggcaa agggataggt ggaaccaata    3600
gtaccatatt gctagctctt gtggagtaga gctagcttaa atatggaagc cacactcact    3660
caccaagtca tggatgagag gagagagtgt ggagagccac acgcgcgcgc gctcggctcg    3720
cctcgcctgg cctggcctgg cctggcctgg ccggggcgaa gggcgcgggc gcacgacatg    3780
cgcgtgaatg gtc                                                       3793
```

<210> SEQ ID NO 32
<211> LENGTH: 7653
<212> TYPE: DNA
<213> ORGANISM: Zea mays
<220> FEATURE:
<221> NAME/KEY: misc_feature
<222> LOCATION: (75)..(174)
<223> OTHER INFORMATION: n is a, c, g, or t

<400> SEQUENCE: 32

```
ttttcaactc tacaacaaaa gttattaagg gttcatgtag agaaaatgga cgaatctcta      60
gaaagtttaa tttcnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnggtgtt     180
tggtttgtag agtcaaaact cagttttaaa taccatggtt tacccaaaac tgcggtattt     240
ttggagtttt tgaaactcca ctcaggacct cagttttctt ctcttctctc tacatatgct     300 ttgttttac aatagaacca aacagatctc ggttttgagc aatactgtag ttttattgtg     360
ataaagcaat accgtagtat ttatgtcatg tacaattgta aactatagta tctcaaaact     420
acagtatttt aaaactgcat tcccaaacag gccctcaatg ttcagacagt attttaagtt     480
ttggcgatct tattatatca cgtcatttgt ctgttcgaaa gaatcttgac tgcaaaatgt     540
cgccggtaag aatgccgtag tatttgaaga aaacacaggt tgagcaatac aaagcatagc     600
aaacatttct gtataacgac attgctttat ccagagaact ctataatgat tatattccat     660 tgattttgt atataacaaa ttatttacac ccattcagtt cctcacagtc ttgcccctag     720
tcaaaaatca aattttacct gttcggacca ccaaatcaat ggcaatttgg caatgggggg     780
agaaataatg caaaattcat ttgcttctgc ttagatttct ccccacccga ctataatgag     840
tggaaaaaaa ttctcctttc agatcatctc tgtcatgcgc ccatggctgt ctgtcggtac     900
tgagaggcta aatggtaacg ctgttgggga cgccgcggca ggtgatgccc ggccccgacg     960
tgggcgccat gagctcgtac ggcagcacgc cagcgccgca ccggttgcgg cggccagtgt    1020
cagcgttgcg ccgttcgatc tcctcctcgg gcgggcgcac ctcgtccgcg aactcgcgcg    1080
cggccgccaa cgccgccggg tcggccgtcc acgcctcatc aggccgctcc ccgaggtact    1140
```

```
gctcgtcggc ggagtgcgtg gacagcgtgt cgatgacggt catgaacgtg gtggtctgcg    1200
tcaggctggg cagcgccgac aggaagaagc ggtgcgggtc ggccaccagg tgcgcgtact    1260
ccgggtcgcc ctcggcgggc accagccgcc gcatcagcgg cggccggttc gggatgtagc    1320
cgcccagcgg gtactgcccg aagttgagcg ccgcgtgctg cgccgaggtg agccacagca    1380
gcgtcgtcag cagcgacgcc aggtccgcgg gcgtcgacag gcgcggccac cacggcgcgt    1440
cgcgcttgtc cgcgtgcccc gtgtgcacgg cctccctgta ccacgactgc agctcggtgt    1500
cgccctgcac ggactcgtcg gacgggtagt acatggccac gtaggcgtcg caccaccgcc    1560
tgatggccga ccagagcagc aacccgtcgg tggcgtacgg gtagtcctcg atgagcagcc    1620
ggagaccgtg cggctgcgtc gggtcctcca cggccattcc tctgtgacaa gggaacacca    1680
tgtcagcctg aatgcggctc gtatttccag ttttccatgc actgcattgc acgaagcact    1740
acaacttcat agatgttcca gttgatttgt gtaccttctg atgagatcgg cagggaggcc    1800
ctcctggtct agccgccaga gctcccggta cgcgaacgag ctcatctcca tgcagtagcg    1860 gccagggggtg aacccggact cgatgacgcc gtcgccgttg atgaggatct gccgcgccag    1920
cgcgttgatc ttgagcgtgt accgcatgtg aggcttgagc agcttgaaga tggggtgcat    1980
cgtgctcagg tgccggtgcg ccgcgatgat gaacggctcc atggccgcgt gcgtcctcag    2040
cctgcacacg cagcgcaatg attagtcgag gccaacactc cggttgctct gctctgcatc    2100
aacagacgat gatggaaatt gggaatgacc gaccgactgt gtcgccgcgt tcagaggtgc    2160
acataccagt ggttgatgag ctggtggacg ccggcgtcat tggagcagac gtgtgccttg    2220
gcgagctgcc acagccagtt gctggtggca tcggcgggcg gcgtgaacac ccgcttggcg    2280
cgcgcgcacc cgtcggtcat cggcggcagg cacagctcga tcgcgatggg cttcagcgtg    2340
cccgcggccc tcaggaagaa gagcgtgcgc gtgccgtagg ccttccgccc gtccagcgcg    2400
ttgatccggt ccaggaacgg catgaagatg tcgtggtagt ccagcatgta cagcctgtcg    2460
tcctgcagcg cctgctgcac cgacatgccg tcgagctgtc cgatgatgtg ctcctccgtg    2520
atggccgact ccggcgggcc gtacacggcc gggtccagct tgctcatcgg cgggaacgcc    2580
tgggagagac acgagaggaa cggacggcag tgagcgagcg gtaagcacgg cggcgtcttg    2640
acagcaacgg ctggggtcgt tgagcagcgg actcagtgtc cgcggcgtgt tgggcttgtg    2700
attgatatgt atacctgaag acgttcgatg ttgacggggt tgatgccagc cagcgcctgc    2760
ctcgcgaact cgtcgtcccg cagccaagca aacttgtcct ctgccacacg gaagggcgga    2820
aaaagaaaac agacgacagc atgagtacaa cattgtcgtg ccccgtatct tatcgtatcg    2880
gacctccatg gatcatggac ggaggaggag gaaggcgcat gggcgctggc ttactcttga    2940
tgatgtcggg agtgtcgtag cggaggaggc cctcgctgtt ctcctggatc ttgcgcacga    3000
agggatcttc tggaacagc tggtcctgca gggcctgctt caggcggagg ccctccttga    3060
agaggttgtc cacgtcgtgg aagcggcga agtcgcggat gtcaggcgac acggagctca    3120
ccagcagcgg catgaagtta tggagcagcg ccttgagcgc ccctccgac agcatctcgt    3180 tcttcccgtc ctcgaactcc tcgtcccggg acacgtagat gggctccggg tactccaccc    3240
ggctctccgc gcggtcgtct gcaagcgcca ccacgaggaa atgttagcct cggtcaacgt    3300
cgcccgcgat cgggtggttc cgatacgaaa gctacgcgcg acggcgacgg cgccctctcc    3360
gccatgcttg gtcgccactg ttgctgtcgc ggaatttata ggacagatgg cggtggtgac    3420
aagaactgaa cagggaaacg ggaaagcgga ggcttgcctg tgatggtctt gggccggccc    3480
gttcgcatcc gccgcgggta cggcagctgc tgctcgccgc cgaggaccgg gcgcgcgaac    3540
```

```
tcggcgccct tgtccgggtt gccgaggtcg ttgtacacgt catactccca cacccggtcg    3600
gtgatcctgc gctcgccggt gtcggcaccc tcgcccctca ggtcgctgag ctgctggcgg    3660
cggagctcct gcaggcccgg cggcgtctcg gccggcaggt acggcttgtt ggtgaagaac    3720
acgcgcgggt tgcggtccac gcgggtgggc tgcacccacg agttgcaggt gaagtgcgcg    3780
gggccggagg gaaagccctc caccacgatg ctctcgatga agaactcgcg ctggtgccgg    3840
ttgagcacgg tgaccgcgcc cggctcgccg aaggacccgt caacggtgaa gtccgccgtg    3900
tacaccaccc gctccgtctt gacgtccttc ttctcgaacc agcccaccag cgccgagcgc    3960
ctgctcttct tggggccccc ctttcctgcc accgattcaa cgatgattcg gtaagatcga    4020
tgcctcgcct ggcgtaattg cgtactaact ccatcttcgt ttcgacgcag acgagatggt    4080
aaagacggcg gctttgggca caaatcaaat attcaaatca agagagacag ctccacgtga    4140
tggtccattt ggaaatgatg actcggagac aaaggcacca gacgtcaagg cgcaccagct    4200
ggaatattct cgccgcgggt tccatgaagg tacgtggtgg tggtggcggt ggagcgaacg    4260
gagaagaaga gcggcgagtg aagaaagggg aaagaaagaa agaaggaatc aatctatgct    4320
actgccagta caattcaaag atgcaacgca acgccggatg cgtcttggaa ttccatgcca    4380
tcgcgtggcg ggcggcgacg gggatggtgg aatcacggaa ctgtttctta cttgggtcgg    4440
tctccgtgct gatgagctcg aggaggacac tgccgccaac ccggtcggcg tacgcgtcca    4500
gctgctcggc gacccggcgc ttggcgtcct ccttccgcct ccgccgcacg gtgaccacgg    4560
cccgcgcggc cacgctctgg gggtgcggct ccgggggggcc cgccccggcc ctctccggtg    4620
gcgccggcgt caccacgacc cgctcggcca gcgcgcccac cggcgcggtc gacctcagcg    4680
acgacctcct cctgtgcgcg ctcccctccc ttccgaccgc ggcgaagcag ggcccgcctc    4740
gccgctcccg tccgggcgcc gcggcagcag ggctcgccaa ggaagatctc cccagcagct    4800
tcatcgccga cgccatgggc agagctccag aaacttcctc ccccttgatc gaccgatcgt    4860
agcagttaag gttggctgac gcactgaaga acaaaacaac aaatcgccgg tggactagtt    4920
cgcggatcgt ttccgagtgt tttttttttct ctctttctct ctctccctct ctctcgttat    4980
ggtgctttgg actagtctct gtttgtgcag tggcgcgagc taccaccttg ctcgcggtgg    5040
gagcagcacc atatataggg gcgccggtct gggagtaagt gaggactcgc tggggcctgc    5100
agtcctgcac ggagcagcaa ccgacgcgac gagctcggct cggctggacg gacgcgcagg    5160
cgcggcgatg ggtattcctg cgccggccac acgtgttgca tgcgtcctat gcgaccggga    5220
aaaatagggg cggagctgcg gcctgcggga ccgatgcttc gacgcaggtg acgcggacaa    5280
cgatggcccg gccccggccc cggcgtgtgt ggttgctgat gcggacaacg atgcccgtg    5340 atgccgcgca ctactactgt atcagagatg ttgaagaatg aactcagggg ctgtttggtt    5400
tgtggctaaa cgtgtcacac tttgcctaag gttagtcgtt cgaattgaag aactaacctt    5460
aggcagaaaa gtgtggcaaa atgtggcaag ttagtcatca aaccaaacag gccctcaatg    5520
tgccgggtgc ccctaaagac gaggtactaa acaacgtact aggttgacag tggattggta    5580
tcgaaagtag cgcgcgtatc ttggatgcta acaatttgaa caacggttta tatgatagtc    5640
atataaatat taaaaatata tatcgtggac aataggaaag aatgacggtg caaacagggg    5700
ccgtaagtat aagttcaggg caggcaatag ggccatgcag cggaggcgat cgccggggc    5760 ctcgccgggg gcccaagaaa gaatgggct caatatctaa tataatagta gagttggtat    5820
taaattattg tcttactaag gccccgtttg attagaggga ctaatcttta gtccctcgtt    5880
```

-continued

```
tttagtctcg tttagtctct attttaccaa acgaaaggac taaaataggg actaattggc    5940
tttagtctct agtccctcac atgagtgcta aatggactaa agggcaacat ttactccaat    6000 taccctttgct agaaaattgg tgtcaaacaa aaaaagggc attttggtct ttatgtgttg    6060
catttaatgt atttagaatc tatttagtcc ctaaagccaa acaggttagg aactaaaatt    6120
tagtccctag actaaacttt agttatagga ctaatggaac caaacggggc ctaaattaca    6180
tatatgcgga acaaacgacg catatgtcta gctaaagcgt ccgttgaagg cctcctacac    6240
tgctacacag aaccagtctc gttctcactg tcgtcaccga tcgcatgtca cacgctcgta    6300
gcttaattag ttttatcgaa attataataa ttatcagaat ggaattcaat tccaactaaa    6360
caaacggagc ttaagggaaa ttagtttatt ttcaaatgaa aaataggaat tccttagaga    6420
aatagggctg tcaaactaac actaaatata ttgtgatcga ctttatttct cgataattat    6480
cagacatatt aaattgaata tatatcaatg tatttgttta tgtctttgca agtaaaattc    6540
atacatatta tttaaatata aaattataa tagaaggtct atcacaatga gctcgtatgg    6600
ggccctcaaa atcataggac cagggttgta caagttatgc aagtgaccat tctggtcctt    6660
tagatcatga tctaaatata gattttacca taggcgtaac aatagtctgt taaggtttta    6720
gggtttaggg gatagtgagt atggataata tgatttttt ttctttggtg ggtataatgt    6780
gcgtgcaccg gatatgtaac ccgctgccat ccctggcctt ggatggtgat ggtgacacat    6840
actatgcagt acgagtata tatgcgtgtg ggcacttggc cacgtagcga gcgtggtgac    6900
cgagatctcg tgtcgagacg ttgctgtcca cggcgatctc cgatccggcg gccggtggtg    6960
cgcagtaaac acacacacac acacatccat ccctcttcct ctaaactaaa gcaaacattg    7020
atggccggtc cttttgtttc tcatcatcat ctccgaacac gacgttcttc ccatagttct    7080
cgctaagaaa aaaaagaag agagagagct ggccacgctc ggctgctcgc ggcgggaggg    7140
acgcgtataa gggcgatgca tgcgcgtgcg tgcaccgtgc agtgcatgtg ttgtttccgc    7200
ttcttctgca cgccggtgagc gatcgagata caatgcagta agtgggcctc gacgctgacg    7260
ggcggcgccc gctgcccgct agcgcgttga ccacccgtcg tccaccaacc tcctgccctg    7320
cccagcccag ctcccgatcg cttcttcttt cggcgcgtgg ggaggccggg ttagcttagc    7380
cccggtcgcg cgcacggccg tcaaagccgt gtaccggacc gatcgggcgg gcctgtcaac    7440
ctgtctgatt acacttgatc aggattcaga gttgagataa aaggaggccg cgcgcgcgct    7500
aaaagaaacg aaagagagag cggccgagaa agggaagcta aagaagaaa agcccgagca    7560 tctcctccat gcatgcacga gtatacatac aatggcagga tctacacagg atcatcggat    7620
caccggaatg gacagccctt ttgccaaaag ctt    7653
```

<210> SEQ ID NO 33
<211> LENGTH: 6081
<212> TYPE: DNA
<213> ORGANISM: Zea mays
<400> SEQUENCE: 33

```
aagaaaatac aaaaaactag agttaatgaa agatacaata aactcaggag tctcaactta      60
acttgaggag agagaaaata gattcattca tgactgagga cacatgatgc aagaagaggc     120
accatgatta agggtaagat ttcaaaataa ttacatattt aaatatatag agatgccatg     180
catggaaaaa atatatatat ggataaatat atattgtttt taaataaacg acaataagtt     240
ttgataaata gatataaact atatagtacc tattatatct attatgttag gaaataaaata    300 aaaatataaa atatatattt gatacaaata tctttttatt agtgagacag ttttccattt     360
```

```
caaatcacaa gataatttga attttctaga tatatgcttg tactgtctaa atattacgca      420
acgcttacat ctttgttttt tagcacgagt gagcacagat cgatgggcta ctaaatgtaa      480
attgaacaaa tagaatgtaa attgagaaaa atagaaggat gagaagacta gagtctacaa      540
aggagaggac agtgtgagtc tgcaaagata gcgcggtgga gccgtgcagc gatagagaaa      600
gatctgttgg ttcgcatcaa tcgaagagat ccgacgaaat ctagcaactc gtgatgatat      660
gagatcagag tctctctccg aatatgcaga agtattgtaa agctgtacta ataacaatct      720
tattttaatg taaagaacga gcgcatgacg aaccacgaat tgatagtccc ctgcatgccc      780
tttcccctcc cagcagtcct agctaagcct aagctagcta tagctccaag tttcaaagaa      840
acaagtagta ggaaacttca aaccaaaatc caaaagaaca cgactccaca cctgctgtgc      900
gcagcgtcta cgaaccaacg aacatcagct cacttttgct tctccaaagt caagtcccag      960
tccacttcac ttgcttcgcc tgcgcgtgca ggagcgagcg ctacggatct gtgaaaagct     1020
tggccgaagt cactactgcc tccgcgcttc tcgaagcgac gccacgccat gccgatcgtt     1080
gctgagctag gcgtcgcccg cctagctgca gctaggatcg gagccagcta gtcgtcgtag     1140
ccaagccgcc gcagctcgcc tgcgagcctg atgtctccct cctcctcctc ctcgtcgtgt     1200
tcggacggcg cgtgggtgga cgtagtggtc gacgacgcgc cgtccgcgga tgacgacggc     1260
gccggcatca gctcctgccc aagccggtcc acgctagccg cccggctctt gggaggcgac     1320
gacgcggacg acgccgcggg cgagcggccc acgatgggca ctggatccgt aagctccttg     1380
ccgtcgcgcg ccggcgagaa cgccacgggc aggtactcgt cgctgtcgca cgggaacttg     1440
gagttcttga agtgctcctt cagcgcttcc aggccctgcg ccgccgcaca attgtaacat     1500
tgacatgtga gcaataagta cgtacgtagc attaaaatgt cttcgacgga tgtagatgta     1560
ggagaagggc agctgcagga gtggagtacg tacttgtacg cgcgcgtatg tcacttggca     1620
gatcttgcgc gagttgtaca cctcccatgg ctgcttgtgg aacgccttgt acagccgcac     1680
ggcagcctcc ggcgatgtca ggttgacgaa gccgtagccc acattacact tgttgctgca     1740 ttttttttgtt tttttttcatt tttgcataag gaagaaaaat tctcatttca tgcaagggca     1800
agaaattcag aatggtaatg gcatggagga acaataacta aaaagacttg caatcaaaaa     1860
aaaactttgg cattatgctg cagctgcttt acacatgagt atgtttgaag ctgcatgcct     1920
tttgacagcc actaatgtcc tctcgtcatt gggcattgat aggtcttttc tcaaacttgc     1980
ttcgtgcaag agaaaagctg ccggcggtat atataaaagc aagtgcttta ataagcaaa     2040 cttgaaagca tacattttgt ttgcatatag aaaactactt tgatctgaag ttcaaatttt     2100
ctctttagaa cgaaagtgct gacttttttcc ccctttttcat actcatgcaa ctctttttttt     2160 ttcacagctc catctccata gctaagcgtc tatctctact gtctagtctc aacactacaa     2220
ccccatcggt gccgcacctt ttgtatgtgt tggcctcgtt atggaagtgc acggctgtgc     2280
aaagcaagaa aggcaggcag ggaggcgatc ccaggggcgg cagcagccgc gagaaaggaa     2340
ggcaggccgg ctccctcgcc atcggcagcg gcagcagcag ccagcagatg cgcgcatgca     2400
accaaagaat ccatgggggg gcatcaaaac gagaaggatc tggcatggtc ttgcttgccg     2460
ctgccaaatt tatttccatt tgggctagta acgccatagc ccatctatgc ctgctgcact     2520
gtactctacc cacccaaaga taagatacct cgatcctgaa gctcacgctt ccacagccag     2580
ctcctcgcct cccaccccccc cgcccacatt tcccactcca accattattc aaggcaacaa     2640
attcccagga aaacaaccga attcaggctg ggaagcttgt gtgtgttctt gcattgggca     2700
```

```
ccataaaata taagtcaatg cgaacagcta aatgcaatta tgtgagaagg aagccgagcg    2760
cgcaactcac ttgaaatcta tggggaggta gacgaaatcg taggcggaga agggctgctc    2820
ctcgccgctc gccacgatcc actcgttgga ttggatgcag tggttgtcca gcatgttgag    2880
cagcagcttc tggctgcgac ccaaacgcct cgggcatcag ctagcagaat cgcaattctg    2940
tgcgtcgccc atgaaatata gcattgttgc aacaaacgtg gagattggca gggatacctg    3000
tacttgttcg gtatgttcct gatcatgacg gtggtcctcg tatccatctc cgaagccggc    3060
gttgcttgcg tgtcggcgcc gccgccggcc tcgggctcct tgaacaggaa gcgcgcctcc    3120
cacccgctct ttcgtccttt ccagctcccg ccgccgctgc tcccgacgcc tttctgggtt    3180
tgcttcccgg acgctgtcgg ggtcgacgag gatgccgccg ccgccgccac cacgatcttg    3240
ccgcccttgg tcttgcgctc atggctcgtt ccggcattgc ctcccttgga cgactggtcg    3300
ctgcccgcgc tagacttaca ggagctcctc ctcagaagca ccactccttc cctcgccctt    3360
acggaaccgg acgacgacga ggatgccggc ggctgagacg acgtcggttg gacggtcgc     3420 cacgtcgctt gaagcctcgg cggagtcggc gcggtgggcc ggtgctggtg gggtgcgtac    3480
ccgcgcctag gaccgacagg cacacggcaa aaattcagcc gcccacaggg tgatgggaag    3540
gctagctgac tgaaattgcg ttgttgttta cctgcggggc ccggggccgg aagggcgcgt    3600
gaactcgacg acgaggcggc ggccgaaaag ctcctggccg ttgagctcgg cgagcgcgcg    3660
cgcggcgtcg cgcgtgtcga agaagtccac gaacttgtgg ctgggccgct gcgccgactc    3720
cctcacatcc ttcaagtccc ctgcgaacac gaggacgggc caatacaatt gctgcgggaa    3780
acacaagaaa cgagcgtggg aaaacgaaat gcctggttgg tcggctcggt cggtggcgcg    3840
taccgaaggc ctggaagact tggcggaggt cagcgaccga gacgccgggc aggggctca     3900 ggaccaccag ggagccgcgg ttgtcgccgt cgtcggcgcc ggtggcgaag tgggcccaca    3960
cggcgtgccc gaggacgagg ccgcggccgt cgtcgttggg gtggggccag tcccaggcct    4020
ggggcgtcgg tgcaggagcc cacgccgggg ctacggcggc cgccgcgtag agctgcccga    4080
ggcggctctg ctggcgcatg tgctgctcgc ggacacaggt caaggcgagc tcggcggcgc    4140
ggatgtcgaa gaaatggacg gtggccacgc cctcggacgc caccgcgcac gcgtcgaccg    4200
agcggatcgc gccgaatggc gccatcgcct gcgccacgtc ggcctcctgc gcgtgcggcg    4260
ggacaaggcc cagcaccacg acgcggctcg acgggccatt gaccaccggc gtcgtcgttg    4320
gcaaggtgta ccccggctgc ggcgccatgg ccatcgccat cggaggcact ggctgtaaca    4380
tggctatttg cggcggcgga ggcaccggca tggctggata tgggtggggg cagtatagct    4440
gttgcggaag cggctgtaga ggataggggg cacagaccgt agggtggaac tcctgagctg    4500
cggcatcgag aaggttaccc gtggcttccg ggaacccacc cattccactc cctcccccac    4560
cctccatggc tagagctcag aacaaaagaa accgaggagt ccaaggaaga ctgccgtcta    4620
aagatctaga actttctggt gattcttgat catgccttcg atcaagaacc aggcgagaat    4680
tgtacttggg accccgtctc agtctcactc tcccgttctc tctcctgctt agccgtatac    4740
tcggtgtgtg tgtgtggagt gagagcggtg gtagtaccgc accactgctg ccagaaacga    4800
gagagagggg ccggagagag gagagagatt gggagctctt tttatggtaa ttgccgcggg    4860
aaaagaaaac cggtggggtt ttatttggag ctctacaggg acaaggggg agagagacgc     4920 gaggagggag ggggcggtgg agaagagtcg aggaggtgaa gggcgggcgg tacgaggga     4980 agaggaggaa gaggagagac gagagtggcc gtgtgctgga ttgttttagc tcggatcctc    5040
tgcaacgaca gcacttgttg ctcttgcacg agtcatgccc cgtgcgtaca tgacaggccc    5100
```

```
cacgtctgct tctttgctgg ggagattttt ccggtagatt ttgcgtgttt gttttcggag    5160
ttagatctag cttttcgaga tgccgccggc tacaaataaa gaccatattc ttcaaattac    5220
tgggcgttcg gttaccggac taaaatattc gaatatcaat tataaagatt aatgttctgt    5280
ttaggagtgc tttattttaa gaattacaac tttagatttc tatcttcacc ataaatcaat    5340
ttcaatacat tggtaagaca gggttctggt gagcatcaaa taaagggtcg acggtttgc     5400 gcgcgcagaa ccagttagaa ttctgagttt cttgctatag ttgttggcta gattcacaga    5460
attagctcga aaaatatgtt tgtaacgggt ccagccccccc tcctctataa atacagagga   5520
atacgaccga ttaaacacca tcaatcgaat caataccagt ttatctcgta tttatttctt    5580
gtatatttag gagtagttct agtttagcct tccaatcccc aaattctccg cttctcttcg    5640
actctatatc gataggagtc taggtcggcc tgccaagcct agacaacacc taggatctct    5700
cctccccgac ggggtccctc ccgggagcga gatccaggcg ccaccgacga ccttcgctgc    5760
ccctgcacac gtgcggaccg tccggcctat aggcgcggat cgtccgaccg tcaagcagga    5820
aaccctaagc cctgcgccag gtcgcagacc gtccggcccc tggccgcgga ccgtccgcgc    5880
ctgtgcagtg agcaccgccg ccggttctca cgcagtgatt ggcactcaga aaaagcgcca    5940
acacactttt tggtgacccc gctggggacg acacatatag acccatcaaa tcggccctca    6000
atggccgatt caagggatag ttctgaagtc tcccccagca atatcataga gtcgacttgg    6060
gaaaccttgc cggctgacga a                                              6081
```

<210> SEQ ID NO 34
<211> LENGTH: 3369
<212> TYPE: DNA
<213> ORGANISM: Zea mays
<220> FEATURE:
<221> NAME/KEY: misc_feature
<222> LOCATION: (2428)..(2527)
<223> OTHER INFORMATION: n is a, c, g, or t

<400> SEQUENCE: 34

```
aaaagttatg caactttata gttggtcaca ttttcaaatg aactcattta gtgccttaaa     60
taatcaaatt actctcgatt tgttatagta catggggaat ggaaacgtaa tataaacata    120
attggtgtag tagtgtagtg gtataggagg gtatgcgcga gagagaggtt gcgagttcga    180
atctcaccat ttacaaaaac atataagttt gattcaaaat gatagggcaa cgggtaaggt    240
aatagggtag ggttggagag ttgttcctag aatttaaaaa atgttttgct gttttttttt    300 tatttttcg attcttaatt tgccgagtgt tttttctttgc cgaatgcttt ttgacactcg    360
gcaaagtctt tgccgagtgc ccgaaaaaaa cactcggcaa agaacccttt gccgatgaaa    420
tctttgtcga gtgttctttg ccgagtgtta cactcggcaa agcctttgcc gagtgtaaaa    480
tagcctttgc cgagtgtttt agacactcgg caaagaacgc gattccggta gtgttgggca    540
aacaaaaacc aatgtcgtca tgtacacgct ggtaccttgt gaagagatgg gatatatata    600
accacttgca tcggttgtgt tacttctgta cactaacaca cagtgacaca cacacacggg    660
gggttcccgc ggggtcaaaa cgagtcagac gacagcactg ttacatcgga gcacgacggg    720
tcttgtggcc gtgtccgtcc actgacggtg tatatccctg gcgatgttga gggcgtcggc    780
cgaggcgccc agcagccccc gctgcgagaa gccgacggcg tagagcccgt tcttcccttt    840
ccagccgttg gggaagggga tcctgggcat cccttcgctc gtgaacacgt cgcctccgtc    900
ctgcaaaagc agcagcgtgc gtaagactgg gctagggac tccggcccgg cgccaaggca    960
```

```
gccgacgact gctgctccct gtgggcgagg gacacttcgc ggcgaaagga gctatagctg    1020
cccctgcgag ccccggcccc ggcatacacg agaatggcaa cggggcaggg tgacgacatg    1080
gcgcgctgca gcgcgggcag aggaaggaag tgggttgggt ttttaccttg agccaggacg    1140
gcacgttgct cctgtacccc gtggcctgta tgattgcgtc gaactgctcc tccttgccgt    1200
ccgcgaacct gaccccgcgc tgggtcacct ccttcactgc tcccactacc tggcgatcac    1260
gtttcgcgtc agcccacag ccatttcctt cccccattat tgtgtaaata aaataaaacg    1320
cagaagcgag cgagccttaa ctcctgccat gccatggcat gccagacggc tcattcatgt    1380
gtgatttcta caactgcacg cgccgctcct ttggtgaaag caggctgggg gcaatggcac    1440
taaccttaat tttgccggtt ttgatgtggg ctagcgtccc gacgtccagc acggggtcc    1500 tgccggtgag gttcttcagc tcgatgggcc ccgtcttggg ccgcctcagg ccgagcttgc    1560
ccgtgtcgcc caacgccagc cgcgccgccg ccaggaggat ccggtccacc acccggacgg    1620
ggagcagctt cagcagcgcc atggcgatgc cgaacgtcga gagacccagc atctccctcg    1680
gcagcacatg gacctgcgtg tgtactcggt cagatctcgt gtgtgtgtgt gtgtgtgtgg    1740
ttcaagcgag cgaaagacga tcatcgttgt tgtatactac atgtttggcc gaacagggca    1800
tatctagtat tatgggatgg gtgccgacga cgacatggga caacaagatc gccgcaaaac    1860
caagtgcaaa agtgctcgat cgagcacgac ggccacaaaa cacgcggcac ttgtactttg    1920
gatgtccaaa gcaagacaaa aaaaaggaga gagtagtagt agtagaaaag gacgggccca    1980
aagcaagcca agcagtaaca acatgtccgc cgccgctctg ggagggaggg atcattcatt    2040
agttagttac cgtgttgcgc accaccatcg acggcgcggc gccgtggcgg cacaaatcca    2100
ggctgacctc catgccggag ttgccgcacc cgaccaccag caccttcctc cccgcgaact    2160
cctcccggga cctgtagtcg cacgtgtgca ggacgcggcc ggcgaagcgc gcggcgccgg    2220
gcaggtcggg caggcgcggc acggcgttct cgcccgtggc cacgacgagc cagcgcgcca    2280
ggagcaggtc gccggcgccg ccgccgccag cgcccgccag gcggagcgcc caggcgccgg    2340
cgcccgcgtc gaacgcggcc tcctccacgc gggcgccgaa ccgcggcgcc acgcccgccg    2400
ccgcggcgta cgcctccagg tacgccannn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnatt atttaaattt taagttagaa accatatggt ttaccaaata tacctatcaa    2580
tttcttttat tagaaaaagt atgagtgtct agtttaaatc attttttacat tattataaat    2640 tctactattt cggttttctc ctttcttttc tagatagaaa ttatacgtat aactaaaaat    2700
tgtttattta attcatctaa cattaatata ctaagaatta attgtaaatt actaaatggg    2760
acttttaata accaattcat ggttattatg acataaataa acattttact attctaagta    2820
cttaagtgct atacttatga atatatttat tatgaatagt aaaatctata ttttcattcg    2880
accgaaaata cgtggcttaa gatttctatt tctttatgca aataagtgta cacttaaaat    2940
actactaaca attatcatta cacatatatt aaagctaaat taattataaa catttctagt    3000
atgaaaacca cgtgaacaat cgtaaatact aactttgaag tatttagaac agacgtatga    3060
aactaataaa acaattgcta gtagatttaa aaataaaaat catcacaaga gattacgtga    3120
atttgtgcct agactttaga gagtagcaca aattttcacc ttcttgatct cacgttcgtt    3180
gtagaattcg ttgtagaata aggagctgtg gcttcggaca cggtgttgac gagttcagca    3240
acaaggtgat gtcacggcgc ggaataggaa gcgacgacgc agaggcaagc atgttctgcg    3300
aagcggagaa cgatgacggc aagcatcacg cgtagtgcag aagaaacaaa gaactcggcg    3360
```

```
tcgtggtga                                                              3369

<210> SEQ ID NO 35
<211> LENGTH: 11305
<212> TYPE: DNA
<213> ORGANISM: Zea mays

<400> SEQUENCE: 35
attgcatgga acaagatcat gacaaaagat aatatatctg acttcgtcgt tagatttatt      60
tagcctaaat cttgaacaaa ctaactagat ctaaaaacta cgaatgaaag atatatattg     120
gatctccttt cttcttacac acatgcgatg cacctgacga aggaagaagg aaagaggcca     180
ggacgacagg agcaagtgcg ctgatggcgg caggcaatac gcggccgcgc cctgctagct     240
acttcgtttt tagtcacact gcaagctagc tcgatgtgac tgcagacagt aatggctacc     300
agcttgattg gcaccggtaa taagtttata acaccagag gctgaatccc aaatcctact      360
acgcagctaa tcacgctcac aattaattgt tctagctcta tagcgcactg tagctagcaa     420
cactagtcgt actacactac tactagctat gactactatc caaacgagag atgcagaaag     480
cgatgaagga gccattaacg gcccagactt tctttcatca tatcagcagg tctgtcaaca     540
atcgacagcg cgaatgctct ctctctcagt ctctcgttgt cggggttcc gaaagggaaa      600
gcgaccaact gaagctgaag cgcgcgtcgt tgtctccggc cggcgctgct gtcgccgccc     660
atcaccagcg acatcaaggc cggcacgcca cagagaattg aaggccgggc gggcttcatg     720
aaatcatcgc cagccgcaac agtcgccacc actcacaagc gcccaagctt acgtgaactc     780
tacgtgaaca catctgatcg acgatgccta accaattaat tgccccaccc atcccaaata     840
catgttgatt tcttacaaaa aaaaattgag tatactactc ttataaacac gtaccatcaa     900
tgaaataccg atgatgaggc tatgatcgat gttgaagttg acagaaccac ataaagctaa     960
aactaaaacc atgactcgat cgagcgcagt ggtcccgcgc gcgtgtgcat gcatgcgcca    1020
aggcaaaatc tctgtgtcgt gtctcgtatt catccgatca tcatatatat catctccgtc    1080
tctctcgctt tcactctctc ggcgcaaatt aaagcaagca atccatcgaa cagtcagtca    1140
gatcgggcca tcgtcgttga tggcgacgcg acagcccggg tcacgttcac gacacctcac    1200
tgtagtactg tgcactgtta ctgtcgtcga tctcggccgc tagcgctagc tcgatcggta    1260
cgtttcggcg cccataagga accgagagat tattgggggc gcgccgggcc gtcagagcag    1320
agcagagcag atcttcgtgt ttaattttat cgcctgtaca tgcatgtatc cagaacaagg    1380
acaagctcat gtgtcgctgt cagcgctaac tagctacagt agcttgatat ataatggtga    1440
tcgagattat tgatcggttt ccttctgctg aggttttctt ttcttttaca tgcacctacc    1500
tctctgctag ctttgcattg ggacgtacgc agaaaaattt caaggaata tatatatata     1560
tatatgtagg gttttcatat aaatcagttt atttaacttt gccaccacag caacaactag    1620
atccttaggg taggtacaat gagtgtctta agttgtgtct tagagtgtgt ctagtgggtg    1680
aatataaaaa attcaagaca tgtatcttga cgaagacaca acgtcttagc tttatgttcg    1740
agacaggaga ctagctgatt ggtcatttta atttattgaa tgctatggtt ggtacaatga    1800
atatggtaag acacatgttt tagacattac cactgtattt gtgttgtgtt ttagttgtgt    1860
cttatacttg gagtaccgtc cagcagtgtc taggttgtac attctcttac tgttatagtc    1920
tgttacctgt ggcctatact gacgagctat agcctgccaa atcattaata atagaaccca    1980
gtcagatgtg catgtaatta acgacgagct taaattgcgt gcagagaaaa aaagggcaat    2040
```

```
tgcacagagg accactaaaa agggcagaat agtcctgtgt agatgatgcc gctggatcga    2100
tggattcaca tataatgcct gcaggccgca gctcagtcgt cagggccggg ccggcgtcga    2160
cgtacgtacg agtagtacta tactatatac tatatactcc gtggtccgtg tggaggccgg    2220
attcgcattc cgatcttgca tggaatcttg gtacatacta cgtcgtagcg cttctccttc    2280
ttcgtcgtcc cagaggcgta ggtacgtacg tacgtacgtt cttgcattgc attgcattgc    2340
attgcgttgc atggcaaaag gtggtcgatc tcgatcgtca ttatgttatg ggtgtgttcc    2400
ccggactgtc ctcgtcgtcg tccttgccaa cagaacggca ctgtgcttgt ctctgcattg    2460
cattgattgc gtcggccggc cggccgggac gatgagttta agttcgatgt tcatggttgg    2520
ttgttcgacg ccctgcagcg gtaggagtat acatctcgtt tgttgtctcg aagacacaca    2580
caggcactcg caaatcccaa gcttgagcac tccttcttcc tgcctcgatc gtccctctcg    2640
tgtagattgg cgcgcgtaac acgttgactc ttcgccagtg acgtcacgca cggccgcatg    2700
cactcgggtc gtacggcctt tctgcccgct tggacgtacg tacgtgcatg cgtgatacgg    2760
ccggccggag accccatcga tgatcgatcc caggcccact ggcctgtacg tcctcctcgt    2820
cagtcgtagc cccgcccgga ccggcccac tggccactac tggacccat gcctgtgacc    2880 gtcaggccgt aaagaagtcg tcacgccggc cggcggccca cctgatgatg acacacatat    2940
acatggtgga gtggtcatga tgatgagctg catgcatggc gcgcgtcgta cgtacacacc    3000
aacacaacga cgacgcaacg caacgcaacg caacgcaaag ccgcatagca tgcagcgcgc    3060
ggctccacat cgccacgcgc ctatacaagg ttggccaatt cccatgacgc tacggctacg    3120
caccagagtg cagtaccacc gccgcactac cacaccgcaa actttctcga tcagtactgg    3180
gactgggacg cgatcgagcg agcgagctag aaagagcaag gcgacaagcg ccacgtcact    3240
caagggtcat tttcctattt cctgttcccc agctgagcta tagctcccac agggacagtc    3300
ccacccaaaa cgtaccaatc gtgtgccatc gcgtcttttt ctcttccatt tttttttcctt    3360 acaaaaatcg cttatattat attattggca cgaaaactac tcagatgaac tcctcagcag    3420
ctgtagcctc tctctctctc tctctctctc tctcactttt ttctttaaaa ttatctgtac    3480
gtacgtagat ataaatatag ctatgttacc actactagtg acacactaga cgtgttggtc    3540
tgtgctgtac ggagaacgaa ggtataaaca aatgcgttgc aaaagcgcag ttcgacgacg    3600
atagatgtat atgtatactc cacaaaagcc cgagctgtct tttgtttttg gagaaaaaaa    3660
taaataacgt gtggttcagg aacaaaagct agcggggttg ctactaattg ctactgttgt    3720
tgataaacac gtcctgatca gacgccactt gcttggatct gttttaataa taataataat    3780
aataataata ataatattat tattattatt attattatta ttttcctttgc tttctttttt    3840 tgaactgatt cttttgtatg ttgcaataat aatgttaaaa gacaaaagta acggcaggga    3900
gttgcagata gacctaatat caaaggctgt cagggccctt ttggaacgca gggattttca    3960
cttcacaggt gctttttttt atgaaaatga accggttctt atgatttctt tttttctatg    4020
tttcatcata cgagtggaac tcgaacatcc atcccaaata ttagaagaca aaagtaacag    4080
taggagagct gagaagcctg agatagaccc aatatcaatt aattaaagac ttttatagca    4140
aatccaaaag gatgcaaaaa cacccccgtc aaaaaaataa ttattaggga caggttacat    4200 tttttggag gcaaatatgg tgcatacttc aacagtttta ttcaaaacaa aggctaaaag    4260
accgtaaacc gagcctatat ttttttttaaa aaaactagat ccatctgccc cattccgcaa    4320
acgattgggg agacactacg tcgctcaaat atgtgggggt gggggggggg gataggttga    4380
aagcgggtta ccgtattttt ccaacaatga tggatccgtc gggctgattt ggtgacaagg    4440
```

| | |
|---|---|
| ggatcccgga aggattgaag agaattgagg ggaaaatgaa ctaatttccc tctccattat | 4500 |
| ctcgggatcc agggtcacca aatcaactct aaatctgttt ttcgggttgt tttaagtgct | 4560 |
| tttggagtta ctcttatacg aatttgagtc attttttttt aaaaaaaaga taaatcaaaa | 4620 |
| tatacattag tctgtacata gagtgactgc tctgaaaaaa ataaaaaaac tgtagagaca | 4680 |
| ccttagcccc aataattgta gcacaggcaa caggtgcaca gcacaacata gccccattgc | 4740 |
| atgcatggct gcagtgtgac acatggcggt ggggccctgc ccactgttcc tccttcaggg | 4800 |
| acggaaggt tggttgcggc cccaccatgg cgccaagtaa tatcgccgct gctctctctc | 4860 |
| tctcttttca tgcacacgct cctctctccc tccctcccac cattgctaca gtcgcagctg | 4920 |
| tctgtgtctg caaagtactg actgctccca ctccactcca ccccagttc cgggccactc | 4980 |
| gggcatcgtt tctgttgctg caaatctttg ttggctgctg ctgccttgct atctatctat | 5040 |
| acaccgcccg caccttccat tcctcctcct ccgaagcagc aggcagcagc tgcatcgcac | 5100 |
| ctcacacctc tcgtgtccat cgatccagcc gccgccgcag ctgcagctct cacttcactg | 5160 |
| ttgctgtgcc acctcctcgt cgcctgtagt gtctgtcgat agataaacgc ccgcggaatg | 5220 |
| agagggaagg agcggaagct gcagcggggcg cgcgcgtgca agggctagga ctagcggttg | 5280 |
| caacgtcggc gcgcgcggcg tacgtcgggc atggattggg atctcaacgc ggcgggcgcg | 5340 |
| tgggacctcg cggagctgga gcgggaccac gcggccgcgg cgccgtcgtc ggggggccac | 5400 |
| gccgccaatg ctgccgcggc gggcacgggg acggagagcc gccgccggc gcccggggca | 5460 |
| gcaggggcac ccgccgagtg ctccgtggac ctgaagctgg gcgggatggg cgagtgcgag | 5520 |
| cccggcgcgg cccgcaggga gagggaggcc gcggcggggg cggcgaagcg gccgcgcccc | 5580 |
| gccgggcccg gcgggcagca gcagcagcag cagtgcccgt cgtgcgcggt ggacgggtgc | 5640 |
| agggcggacc tgggcaagtg ccgcgactac caccggcgg acaaggtgtg cgaggcgcac | 5700 |
| tccaagaccc ccgtcgtcgt cgtcgccggc cgcgagatgc gcttctgcca gcagtgcagc | 5760 |
| aggtagtatc cccgccttct ttttcccatgg ggggctggtg tagtgtagtg tagctcgtcc | 5820 |
| ctgtctcgtt tcaaggatgc acaactttac cttttccggc ttgccttttt tttttttcgtt | 5880 |
| atcttttttc tctctctctt tttcctgaaa accaaagaga tgaaaaacct tcatctcgtt | 5940 |
| cgttcgtttc ctcctgtagc tacggtacct gaattattgg cacgcctttt tcctttctcc | 6000 |
| cggcctcctc ctgcgctcgc tgctgctgct gcacactgct ctcaggcagg cctagcgttc | 6060 |
| gtttccttca cttttctctga cgccctgatg cgaattaaca tctgctgctc cccaatcgtc | 6120 |
| tgctcaagat tcagcccgct gccacggaca cgtgagctcc tgcgcttgct tttccgagcg | 6180 |
| gtttcttgct ttcacgcccct ttggcggcga cgggacggga tgccccccccc ccccccccc | 6240 |
| cggtactctg ccattggctc ctcctctagt cggcgctgct tgcttcccgg cgacagttcg | 6300 |
| ccaccgccgc agatgaagcg ccgccacggt ttggcgtgcc gcgttgagcg agacaggggt | 6360 |
| gtactcccag ctttggctac catcaatcat ttgatgttta ggtgccgcgt tgtgagctgt | 6420 |
| actgctacag tatctctgca gaatgtattc tgtagtagta tgaaaggta aggcggcgt | 6480 |
| actgctatag tatctctgca gaatgttcgg aggagtacac caactgaaag aggtttagga | 6540 |
| aaattgcatc gtggatctag aattctagat gcagtagtgt agcctacagt agccctgtac | 6600 |
| acacataaag gcattttctc tataaaattg tctcgcaaaa tgggattttt ttgtgctaat | 6660 |
| tatagggtgc tttagcgcca cctgggccgt ataggatgct ttagcgcaac atttctgaac | 6720 |
| aaccctatgc agcttccata gaccaccaca ggcattcccg catgcagttt gctctaaatg | 6780 |

```
cctccttttc attttracta tccctgaacg acgacccatc catttctttt tccgtctcag    6840
ggaagtagcc attaaatgct agcagtcttt ttttaaagta tcgcttggtt tgagatgtta    6900
ttaggcccgg tttggttgga aaaaccgctc cattttaatc tcctttagtt tgtaaattac    6960
agtactaaac tgttttagtc tttagtatct cgaggagtga ctaaaagaga ctaaaccata    7020
taaatttcac cttttatctc ccatttattt cagttacact aatgacggga gaatgctaaa    7080
gtgtatttta gtcatcttat aattgattta gtgtgtttta atacttcct tagtctataa     7140
aattaaacag gatataggct aaactttagt tggactaaac catataaatt tcgtctggtg    7200
aagtttacgg cagtacagcg ctgtgttggc gcccagtttt gtcttgctca tatggacagc    7260
agagacaggt cccgctctcc tgtggtggac ctaaacctaa acagcgtagg ttcagatcgt    7320
tcctggagcg atcgacgctg tggcaagcga tcctaatgcg atgctctggt gacatgtcct    7380
gtttctgttt acgccggaac atcttgctcg gtggggacaa ttctcaatca ttgatcactt    7440
tgtcttctgc tttaaattgc agactttgta ggttaatagt aagttgtcag ccagtgagcc    7500
aacagattct cagctttctg tttaccgtct gtgtggtcca ggcttgacag gtcttatagt    7560
attttcctgt ctctaataag catggacaag gaacattggt ccctggtgtg atgtgtatta    7620
actataacaa gcatgtatgt gcgccacagt acattaacta ttctgacaat aattacgttg    7680
ctgtttcttc agtgaggacc atcttagcat accgttggat catgtgccca ccctactacc    7740
taggaccatc tattcttcta aaaaaaactg agtatcttat acttgtttag aattatccta    7800
attcaaagaa tcctgtggtc ctaatcgatt atgccatcat tcattggtca gcatattaca    7860
ctgcaacttt ctcgtttgcc cgtactcgaa ttcagttgtc tgatcaagag ttttttttt    7920
gttttttgtt tatgtaggtt ccatctactt gcggagttcg acgccgacaa gcgcagctgc    7980
agaaagcgtc tggacgggca caatcgccgc gcaggaagc cacagccaga caccatggct     8040
tctgctagct ttatcgcaag ccagcaaggt cattttcgta ctcaccaatt tgctttggt     8100
ttttttctc cccaagtctg tacttggttc gaatacatct acattgtttc catcttgctg    8160
gtgctggaca agaaaaggt aaaacgtcag aacagatctg tgcacacata accatgaga     8220
agtaaaagac tgctctgtta aacttgtaga gcttgcgtag catttcagca tgtttcagaa    8280
ctagaattcg gttcataaga taagatgcta ctctagcatc cctgcataca ttagttgcga    8340
caagacgaag attacattgt tgacgcatca agttattatg aacctcttct gtttctgtca    8400
attgtgtcct catatttagt gcaaggtctt gctaatgcct ttaagttaaa aaagattagt    8460
atactgtatg tttctttgcc tttcagatgt gttctagtac aaactacttg tatgcttcac    8520
cacttgtaga ttggcatgta tatgagtctc aaacttccaa cacaattgcc agcagattgg    8580
catatagaac tgcaataaaa attctgattc acattgtatg aaacggcgca cagaatcaat    8640
ttatcagtta tgtcacctga tcgacatttc ttcccaattg atcaggcacg cgattctcac    8700
catttgcgca tccaagactg gaggcgagct ggccgccggg ggtgatgaaa accgaggaga    8760
gtccatatca catcactcac caaatccctc tgggctccag cagcagcagc aggcagcagc    8820
atttcgtggc tctgggagcc gccacgcctg cctacgccaa ggaaggccgg cgcttccctt    8880
tcctgcagga gggcgagata agcttcgcca ccggcgtggt gctggagccg ccggcggcg     8940
ctccagcgtg ccagccgctc tcaggacgg gagcaccatc cgagagcagc ggcgccggcg     9000
gcagtaagat gttctccgat caggggctgg ctcgcgtgct cgactcggac tgtgctctct    9060
ctcttctgtc agcgccggcc aactcctccg gcatcgacgt cagcaggatg gtccgcccga    9120
ctgaacacgt ccccatggcc cagcagcccg tggtcccggg cctgcagttc ggcagcgcgt    9180
```

```
cgtggttccc gcgcccccag gcttccacgg gcggctcctt cgtcccctcc tgccccgccg    9240
cggtggaggg cgagcagcag ctgaacgccg tgctgggccc caacgacagc gaggtgagca    9300
tgaactacgg cgggatgttc cacgtcggcg gcggcagcgg cggcggcgag ggctcctcgg    9360
acggcggcac ctcgtcgtcg atgcccttct cgtggcagta gtcgtcgtca cttgtcagca    9420
gccgctgcgt tctctcatct ttcgcgcttc agacgatctg gtagggagat actggcttta    9480
gtgatcactg atcagcattg atttctgttc tttttcctgc attcgctttg ttgaatcggc    9540
tctgctcgcc agcattcgtg tggacatttt ttgaacataa ttctgtgttc gtttccctca    9600
cattatcttt gctacggtga cacctgccgg ctgctgaccg tagcatgttc cttctcttgt    9660
gacttgttct cgagacgtcc atttgatgca gggcgcatcc agaatttttc agttgcagtg    9720
cagacgcaat ccgatgcgtt tgaagatgac gggcatgttt ggttcacggc taactgtgtc    9780
atacttcgac taaagttagt cgtccaaatt gaagaactaa ctcaggcaga aaagttagat    9840
aaaatgtggt aagttaggta gtaaaccaaa cagacccgac aactgaggac ttgttcggtt    9900
tgaaggggtt taggggatt agaggggatt caatcccctt ctatacaaat ttatatagaa    9960
ggggattgaa tccctccaa tccctcaat ccatccctaa ccgaacaggg cctgaacggg    10020
ctcgccacat gtaggcatga agaatagctt gctaaatctg ctaaaaagt aattgattgg    10080 taattcgtcc tcattaccct agtaaaaaag gggacaaaat acgtaggtgc cgcggcatca    10140
ggattgctgg aggtagcaga gcacagaacg tgatgagttc ctgcaaggag tcgtgaatag    10200
cccctatctc gatctccgat tctccacggt aaattcctcc attagataat atcgatgaga    10260 aagttttct ccccacccac gagaatgtaa ataagaaaa aaattctcca ccgacaatta    10320
aatgaggacg agaataagga agcatttcta accctgtttc ttgcggggac ccgttaaact    10380
tacatataat gatgttttta tataatagtt aataataaaa ataaataatt atcttgtcaa    10440
gagatcattc attataaatg tgctcatttt gatgtaaaca taatgattat cttacatctg    10500
acaatatgaa gtgacaatgc tttgcatcaa taacaaaaaa gtatgtccta attataattt    10560 aagcggggc ggaaaatagg gatgaggaag aaatacccag taagcttttcg tgaccatcct    10620 cgtgggaaac tttattttgt cgcagggata agaatagaga gctaaacccg atagagaatt    10680
tcccgttgcc atccctagtc atgcgggggt tgcgttgccc atcctatagc tccatgctgg    10740
agataattca tactgccgcc ggcattgaaa cacaatcgtt ttggacatga atccgtgtat    10800
accaggagtg attaattaaa agtcatattt ccaattaatt atacccatat tatatatata    10860
tatatatgct tggttgtcat tgttattgaa ttgtctctat gattgcagct ggtcaacaac    10920
attgctctct atcatgccca cccaagtttg attcttgtgg ctttctattt tttacatgga    10980
ctctgtatat ttttttcatc ttttcaagtt cgattcttgt ggcctcctat tttttacatg    11040
gacgctgcat atttttttc atcttttcat tcttgtgtgg cctcctattt ttaggcatgt    11100
tttgcctcac tcgtcgtagt ttgccatgcc tagagttagg tttccatctt ttcattcttg    11160
tgggatatgg cctcctttt cgggcaagtt tggttcgctg cctcatttac catagttttc    11220
cacggttaaa gttgggcagg tttgactgaa ttagacgtgt gtttggtttg tagccatagt    11280
tgtggcaaga ttttctcct tctat                                          11305
```

<210> SEQ ID NO 36
<211> LENGTH: 4113
<212> TYPE: DNA
<213> ORGANISM: Zea mays

<400> SEQUENCE: 36

```
ttgtggtgtt gaaaacagga cgaataaaag aaagagaata cttgctcttt tagaggtttt      60
ttaagagacc tttttagagt attattggga atgttaggag ttaatgagta taatgttttg     120
agcatatttt gacacctaca agtaattttt tctatatcct tctttatgat atactatact     180
tgaaagaaga ttgaattaaa actaaaatct ctctctcaag ttgaattgtt gtgccacatc     240
tttcactaat ttataattaa agggtctcat attttttgta ctttttttata attatattta    300
attgtaaatc tcataaaata ttgttagctc gtgtcatcaa atcactaaaa tccataaata     360
ggattgatgc acttagctct ttaaaatgaa aaaggtacaa aaatataaaa aaaatcgtga     420
acccccaat caatttctaa ttgcattgtg aaaacttcga caacaaaaat ataagatacc      480
accaaaataa aatagtatca aacaatatca tcctctattt caaacttctt tatgcaagca     540
gcgtcattca caatttcgcg tcctctattt tacacactgt actgcagaca accttaacat     600
ctatgttggt tgtatcacat attttttgttg tagaaaattt ccaaagcaca tttaaacttg    660
attaaaatat tttggggggtt taacgatatt tttttattat tctagaacta aatatatttt    720
taaagcttat agatatattt tcgcgggctc taaatacttt tttctccggt cccaatctat     780
ttctaatatt tttgaacttt ttatatactt tcaatgtttt aaataaactt tttccgattt     840
tcttagtaaa aagttgaaac catcctaaaa taaaaactat ttctaaccat ggtagagagc     900
taatttaagc ggctttaaga tttgaagaag aaattgcctt attttagagt tcattcaaga     960
aggaaaaaat ggagtcctag ttgagggaaa acaccacaga ttccacagcc ttcgcctgtt    1020
cgccaccttt cctccaaaat ttgacccaca cgcggcgacg cccgaggccc cgagcgacca    1080
catcctccgc ggccgcggcg acgcccgagg cctgcaaaac cctaaccact caggttctgc    1140
cggccaccgc caccaccacc accagtccac caccatgctg acagccactc cctaccccca    1200
tcagctcctg ccaccttcc tcctcgtcct ggcgtcggcg acccaacctg cagtccctgc     1260
ctccaccgac cgcgcagcgc ttctcgcctt ccgcgcgtcc ctgtcgccgc cctcccgcgc    1320
cgcgctatcc tcgtggagcg gcccgctctc gccatcctgg ctcggcgtgt cgctccaccc    1380
cgccacggcg ccagcccctt cggtcaccac tccctccgtt gccgaactct cgctccgggg    1440
cctcaacctc acgggcgtga tcccgcggc gccgctcgcg ctcctccgac gtctccggac    1500
gctcgacctc tccgccaacg cgctttcggg agagcttccc tgctccctcc cgcgctcgct    1560
cctcgcgctc gacctctccc gcaacgcgct ctcggggggct gtccccacct gcctgccgtc    1620
ctcgctcccc gcgctccgca ccctcaacct tccgccaac ttcctccgcc tcccgctctc     1680
cccgcgtctc tccttccccg cgcgcctcgc tgcccttgat ctctcccgca cgccatctc     1740
cggcgccgtc ccgccgcgga tgtcgccga ccccgacaac tccgctctcc tcctcctcga    1800
cctctcccac aaccgcttct ccggcgagat ccccgccggt atcgcagccg tacggagcct    1860
gcagggggctt tttctcgcgg acaaccagct ttccggggac attcctccgg ggataggggaa    1920
cctgacctat ttgcaggtgc tggatttgtc gaataaccga ttgtccggtt cagtgcctgc    1980
cggacttgca ggctgcttcc agcttctgta cctgcagctt gggggtaacc agctctctgg    2040
ggcactccgt ccggagctcg acgcactagc tagtctcaag gttctagatt tgtcgaataa    2100
caagatatct ggggagattc ccctgccgct ggctgggtgc aggtctttgg aggtggtgga    2160
cttgtcagga aatgagatct ccggtgagct cagcagtgct gtagcgaaat ggctgagctt    2220
gaagttctta tcactggctg gtaaccagct ctccggccac ctacctgact ggatgttctc    2280
gttccccctg ctccagtggc ttgatttgtc tagtaataag tttgtgggtt tcatcccaga    2340
```

```
tgggggttc aatgtcagtg aagtgcttaa cggtggaggt ggtcagggga ctccatcaga    2400
gagtgtgctt ccaccccaat tgtttgtgtc agcttctgtg gacacggtgt catggcagtt    2460
ggatttgggg tatgatgttc aggcaactac tggtatagac ctgtctggga atgagctctg    2520
tggggagata ccagaagggt tggttgacat gaaggggttg gagtatttga acctctcctg    2580
taattacttg gctgggcaga tccctgcggg gcttggggc atggggaggt tgcatacgct     2640
tgacttctca cataatgggc tgtcagggga ggtgcctcct ggaattgcag ccatgacagt    2700
gcttgaggtg cttaacctct cctacaatag cctgtctggg cctttgccaa caacgaagtt    2760
cccaggagca ttagctggaa acccaggaat ttgcagtggg aaagggtgct ctgagaatgc    2820
aaggactcca gaagggaaaa tggaaggtag caatcaccgc ggttggcttg gtggctggca    2880
tggagagaat ggatgggtat ctcttggtgc attttgtatc agcacaatga ctagcttcta    2940
tgtatcatta gcaaccttac tatgctcctc taatgcaaga aacttcgtgt tcggcctgt     3000 gagggttgaa tattaacaag aggggagatt gcaaaatcag gttgttttga agttcgagcg    3060
actctggtct gcagctgatt aacaagaaat atgagcatat gagatggata tcttcagcca    3120
agaggaagtg ctgtctcttt taatgatcaa tcaagctctc ttgattgttt cctaatattc    3180
ttgatcttgg gatgtgtaga tctagttcta atattcctac tgttatagaa tgcaatcacc    3240
tgctggtgct tggttgtagc cctggcgtgt tggaggatt ggacaccaag gatgcacata     3300
atttgaagcg ctggtactgt gaaccacttc agatgtaaat attttctttg gtttttagtt    3360
ctgatctagt ttaaaactgg acatgtattt agtgttgttg agctaccttt cgatgttata    3420
ttatgtcaat ttgctggaag atcatttgat aacaattgtc taatccagtg gattagtcgt    3480
gtagattgtg aagttcgtta tgtttcttct tagtgctatg tatatcatct ttctgtctga    3540
acttagtttg ggggtaaaag gctttgttat tatgtgactg aaactgcaaa tgtgcttgac    3600
tatttcttgg tgctgctcct gtaacaccta tagttttata ggtcaatggt aatagctgcc    3660
tgaagcagca tccagcaggc cggcaactgt ttttggtact gtaatacttt ggaacagagg    3720
cgcaaagttt gtgattgcag aatgatcaac aaatgtattt attgcaaagt gtgagacaag    3780
gcaacataca tatctctgtt ttgtgcatta ccaaactaac ccaggctgta attgcagatt    3840
gataattcct atagccgtag cttcttcagc tggataaggt ggagaataag catcagtggc    3900
ttttcaaagg gttcggcact tgtgcagaat cagactcatg caggaatccg gttctaactt    3960
ttccactaaa acctttttcc tttctgaact tgctgcagta cctaccacta cttgtaatgt    4020
tggatcagtt tcacagttaa ccacagaatt tcattgcttt taatcaaacg tgaaatggtc    4080
acacagaaaa accaacatcc ttcagaaccg ctc                                4113
```

<210> SEQ ID NO 37
<211> LENGTH: 4341
<212> TYPE: DNA
<213> ORGANISM: Zea mays

<400> SEQUENCE: 37

```
gtggagattt cctctgatca tcagatcatg atccttcgtt cctttgtga gggaaaaaag      60 aacggcggaa atgcgctgcc aattccggga aactacacat ccttcttctt tcttcttgca    120
cgaccacaca acacaaatgg tggccggtgc ccttaacctg ttacagcttt cggacgatct    180
tcgaatgcac ttcaactgtg ggaagaaatc agaccatca tttcaccgat gagacatata    240
ctcacacact tctacttgaa tggttgttta tcttttgagc aaaaagtcac cgccagaaat    300
```

```
ggcgccgatg ggtgtgcctg tgctgccgag ggttaacgat ggaagctact agcgtagccc    360
ctagtgctgg agcaaattga tggcgctcgt cccgtcccgt cccgtccctc cctctgctgc    420
gcgcgcctac gccccgcccc tctttctctc tctctgacac cgcacgccgt gcacccagcc    480
gtccactgat ccaccaccac caccccctccc gtccccgcc atgccacctg cctttgacct    540
gcctatcatc tcgcccgcgc cgtccccgtc cccgtccccg ccgccgccga ttccattcca    600
tatgcccatt ccctcctcca ccaccaccac cgctaagccc ctcactccgc tcgcttccct    660
tttattccat ccgccacccc cacgccccc tcgccaccac accacaacgc cacaatcaca    720
atgcctcctc ccaccttcct cctcggcctc ctcctcctcc tcctcctcgc cgccgccgcc    780
cccgcccccg cctccgccac gccggagcgg gacgcgtacg cgctgtcgag gctcaaggcg    840
tcgctcgtcc cgtccgccac aaactccacc tcggcaccgc tgtccgactg gacccggcc    900
gcgacccgc cggcgcactg cgcgttcacg ggcgtgacct cgacgccgc cacgtcgcgc    960
gtcgtcgcga tcaacctcac ggccgtgccg ctccacgggg gcgcgctccc gcccgaggtc   1020
gcgctgctgg acgcgctcgc cagcctcacc gtcgccaact gctatctccg cggccgcctc   1080
ccgcccgcgc tcgcgtccat gcccgcgctc cgccacctca acctctccaa caacaacctc   1140
agcgggccct tcccgccgcc gcccccgcc gcctacttcc cggcgctcga gatcgtcgac   1200
gtctacaaca caacctgtc cggcccgctc ccgccgctgg gcgcgccgca cgcgcgctcc   1260
ctccgctacc tccacctcgg cgggaactac ttcaacggct ccatcccgga caccttcggc   1320
gacctcgccg cgctcgagta cctgggcctc aacggcaacg cgctgtcggg ccgggtcccg   1380
ccctcgctct cccgcctctc ccgcctccgg gagatgtacg tcggatacta caaccagtac   1440
agcggcgggg tcccgcgcga gttcggcgcg ctccagtcgc tcgtccgcct cgacatgagc   1500
agctgcacgc tcacggggcc catcccgccg gagctcgcgc ggctgtcccg cctcgacacg   1560
ctcttcctcg ccttgaacca gctcacgggg gagataccgc cggagctcgg cgctctcacc   1620
agccttcggt cgctcgacct ctccatcaat gacctcgccg gcgagatacc cgccagcttc   1680
gccgctctca ccaacctcaa gctgctcaac ctcttccgga accacctccg cggcgagata   1740
ccggcctttcc tcggcgactt ccctttcctc gaggtgctgc aggtgtggga caacaacctc   1800
acaggccccc tcccgcccgc gctcggcagg aacggccgcc tcaagacgct ggacgtcacc   1860
agtaaccacc tcaccggcac catacgccgc gacctctgcg ccggacggaa cctgcagctg   1920
ctcgtgctca tggacaacgg cttcttcggc agcatccccg agtcgctcgg cgactgcaag   1980
acgctcacgc gcgtccgcct cggcaagaac ttcctgaccg gccccgtccc ggccgggctc   2040
ttcgaccttc cccaggcgaa catgctcgag ctcaccgaca acatgctcac cggcgagctc   2100
ccggacgtga tcgctggaga caagatcggc atgctcatgc tggggaacaa tcgcatcgga   2160
gggcgcatcc ccgccgctat cggcaacctc cccgcgctgc agacgctgtc cctggagtcg   2220
aacaacttct ctggcccgct gcctccggag atcggcaggc tcaggaacct caccaggctc   2280
aacgccagcg gcaacgcgct cacgggaggc atcccgaggg agctcatggg ctgcgcctcc   2340
ctgggcgccg tcgacctcag ccggaacggc ctcaccggcg agataccgga caccgtgacg   2400
tcgctcaaga tcctgtgcac gctcaacgtg tcgaggaaca ggctgtcggg cgagctgccg   2460
gcggcgatgg ccaacatgac gagcctgacg acgctggacg tgtcctacaa ccagctgtcg   2520
ggccccgtgc cgatgcaggg ccagttcctg gtgttcaacg agagctcgtt cgtgggcaac   2580
ccgggggctgt gcagcgcgtg cccccatcg tccggcggcg cgcggtcgcc cttctcgctg   2640
cgccggtggg actcgaagaa gctgctggtg tggctggtcg ttctcctcac cctgctggtc   2700
```

| | |
|---|---:|
| ctggcggtcc tgggcgcgcg gaaggcgcac gaggcgtggc gcgaggcggc gcggcggcgg | 2760 |
| tcggggggcct ggaagatgac ggcgttccag aagctggact tctcggcgga cgacgtggtg | 2820 |
| gagtgtctca aggaggacaa catcatcggc aagggcggcg ccgggatcgt gtaccacggc | 2880 |
| gtgacccgcg gcggcgcgga gctggcgatc aagcggctgg tggggagagg gtgcggcgac | 2940 |
| cacgaccgcg ggttcaccgc agaggtcacc acgctgggcc gcatccggca ccgcaacatc | 3000 |
| gtgcgcctgc tcggcttcgt ctccaaccgg gaggccaacc tgctgctgta cgagtacatg | 3060 |
| cccaacgggt cgctaggcga gatgctgcac ggcggcaagg ggggccacct cgggtgggag | 3120 |
| gcccgggcgc gcgttgcggc ggaggcggcg cgcgggctct gctacctgca ccacgactgc | 3180 |
| gcgccccgga tcatccaccg cgacgtcaag tccaacaaca tcctcctcga ctccgccttc | 3240 |
| gaggcgcacg tcgcggactt tggcctcgcc aagttcctcg gcggcggcgg cgccacgtcc | 3300 |
| gagtgcatgt ctgccatcgc cggctcctac ggctacatcg ccccaggtaa caaaactctc | 3360 |
| gccgcatagc agcataacca cgtgtttgta ctccttttaa taatattttt ttcactggct | 3420 |
| cgcatgcaga gtacgcgtac acccttcgcg tggacgagaa gagtgacgtg tacagcttcg | 3480 |
| gcgtggtgct gctggagctc atcacggggc ggcgccccgt gggcagcttc ggcgacggcg | 3540 |
| tggacatcgt gcactgggtg cgcaaggtga ccgcggacgc cgccgccgcg gaggagcccg | 3600 |
| tcctgctggt ggcggaccgt cggctggcgc cggagccggt gccgctgctg gcggacctct | 3660 |
| acagggtggc catggcgtgc gtggaggagg ccagcacggc ccggcccacc atgcgcgagg | 3720 |
| tcgtgcacat gctctccacc tccgccgcgg cccagcccga cgtcccccac gccttgtgca | 3780 |
| aggtcgtcga ttaatttgcc ttatatatga cgattatgta tatgatccgg gcagggttag | 3840 |
| cgcctgtgat ctatttagcg gctgcctttt tggcgtcact cgtctcgtgt gtgatgatgg | 3900 |
| ctggatggat gtgtaaaaca aataaccagc aggtggctac tcgtgaatga agttgccgg | 3960 |
| ttcttattct catgcatata tattagcaac acacaaagtg agatggcata tattccctt | 4020 |
| ccctggcgtt tgttgctttg ggttattcgt cttggcttct cgcggaaggt cttttctgctg | 4080 |
| ttcttgaacg acaggatagt atagaggctt ctatgagaaa gatgcttcat gctgcgaaag | 4140 |
| ttgaaaatgg cagatgcaca ttgcgtatcc ccacagggca ggacactttg cgcatggcct | 4200 |
| agtactaaca caatccatgg agcaaggaac attactgccc ttggcctcca agctgcttcc | 4260 |
| ttaatcatca aggatgaatt aggaaaaaaa aggataaacg gaccgccatg accagagcca | 4320 |
| gtgagggagc cacttcacct g | 4341 |

<210> SEQ ID NO 38
<211> LENGTH: 1753
<212> TYPE: DNA
<213> ORGANISM: Zea mays

<400> SEQUENCE: 38

| | |
|---|---:|
| taagtcttgt atattgtatg tcgtgactct ccaccgccat acaatacgtg gctgaacagc | 60 |
| caagggagag aaagaggagg cacctatgac gttctcctcc tttattttgc ggtcctttat | 120 |
| taatcccaac ttttctattt cttttcttgt tttccccttt cccacctaga ttcatccttg | 180 |
| cagtgtgagat ctatttttct tccacacgtc tagcctaaca actagataag ataaaactta | 240 |
| tatcttatac tctctgttcc aaattaaaat ttgttttagt gaattattgg attcaaacaa | 300 |
| ttcttgatat tttgtatatg tgtctagatt tatcatcatt tatttgaata tatagataaa | 360 |
| aaacaatagt taaaacgaat attattttaa gacggagcga gtatatcatc atacgatacg | 420 |

```
tggctgatct cacaatctca acgtggtcaa agttgtgtgt gccgggccat ctgcgcgtcg    480
tgtgacaccg gtgcatgcgc agccttttgt tttgccgccc cgcccgctcc atgcatggca    540
tgggtgcagg ttctgtagct atgcccggaa gcacctagct agctcgcagc ctacatctgc    600
aaactcacaa agtttgggta tcggaggcat cagcaggtcg ggttcaatgg aacgacggat    660
cacgtctgtg tgtcgctttc gcagcagcgg ggagagcgcg gggcccggcc caggacgcat    720
ggaccgatgg acgcatgcag accattttTG TTTTTGTTTT TGTTTTTGTT TTTTTCCTGT    780
ctaaaatgta ggtgtgctct atcttgcctc ttcatgcgat aatgtgtgtg tatatatata    840
catgcccttc actcttctta tagctcgcta gcccagcttt agtttatagc actctctcac    900
tcagtagtca gctccctcca tttgtccatt ctccaaaggt agttagctag gttaggcaca    960
cgcgcgccac tcgactagct agcagctatg gagggagaag atgacggcgc ccaaatgaaa   1020
ctgcagcaac aacaacagtc gccttgcagt gacaacttga gcttgtccgc cgcctcctca   1080
tggctgccgc cacaggtaag gtcgtcgtcg tcgtcgtcgt cgtacacctg cgggtattgc   1140
aagaaggagt tcagatcagc acaagggctg ggaggccaca tgaacatcca caggctggac   1200
agggccagac tgatccacca acagtacact tcacaccgta ttgctgctcc ccatccaaac   1260
cctaatccta gttgcacatc agttcttgac cttgagctca gcttgtcgtc gctgctagcg   1320
catggtgctg ccagcagcga cggaggcttg tctgttccag tggcaaagct ggcgggcaac   1380
cgtttctcct ccgcatcgct ccccacgacc aaggacgtcg aggggaagaa cttagagttg   1440
aggataggag cgtgcagtca tggcgatggc gcggaagagc gtctggatct tcagcttaga   1500
ctgggctact actgagccag acagaggaac gaactgctac aatgggtacg tgcagtgcat   1560
gatgatggaa tgactggctt tgtataataa taatgatgat ccgattattg ttatttctgt   1620
atgctaaata tatgtctctt atgttagatt taatatatat gacatatttt atctaactaa   1680
attaaataaa ttatatatag gcgtcaacgt attaaatacg tctagggcat cgtagtcttt   1740
ccgaggtgtc tta                                                      1753

<210> SEQ ID NO 39
<211> LENGTH: 2625
<212> TYPE: DNA
<213> ORGANISM: Zea mays

<400> SEQUENCE: 39
cactatatga cactggaggt gtatgcatac gtatgagcat gaggaaaatt attaagaaaa     60
tatttgtagg gactttaaaa atgattacga gggtatttct gaggagaaaa atattttgag    120
aaatattaat ggaatcttta ggcagtattt ctggaaagaa tttgatggag tcactggaaa    180
aatatttgta ggatattttg aaaagaattt tggagagaat atatagcact atatttt att    240
tgttgtgatg aacttgcaaa caaacatttg taaacacaat tttaaaatcc attttaaatt    300
taggactagt tcaagtaatt ttatggtttt gaattttTCG gaggctataa tcaccctaat    360
ccaatgagtc tctacttacg cgcttgcttt ccccttaact ctacaaattt ctcgagtacc    420
taagaaacac taatatcgtc atgcaacgac aatgttcatc taatttttat gaaaaattta    480
tgcctattgg acaaatatta aggttggatg aaatagtgag aagttaggac ataattatgg    540
tcacggttag ttttaatgta tgtcccctcc acgtctataa ctcttctttt actagtagct    600
acaatatcta aaacttactt gctataactg agggtataat attcctatgg aagtgttagt    660
agcttgtgaa ctttcttatg gttaaaaactg tctatccata tttaacgtga ttggctgttt    720
atttatttag tattcatttt agagtcagca gtgatttagc ggagaaaggg agagtctggg    780
```

-continued

```
caattggcgg tctctggtgt catttgacca gtgccaggtc tcagtctgag tctatagtca      840
acagtgatct ctcggtcatt ggttggcagt ctcaggcaca cacaatgaca caacacaagc      900
agggcacagt cacagtgtga gctgagctga gctgggcttg tgcttgtgct tccgcctcct      960
cctccgcggc tactaaaggg tgccagccag ccagccctgt ggggcgccgg tgcgtgccca     1020
aaacaagcaa gcataagcat agaggtgggc atcatagaca tggaggatga cgaggacata     1080
tgggcaaaca ccgccagcag ccccagcgcg tccccaccgc agcccgtggc ggcgggctcg     1140
gtctccacct gcagcgcctt catctccacg cagctgagcc tcaactcccg cctccacctc     1200
ctctcctccg ccgcggccgg gggcgggtcc tccccggtcc gcggcggcgc ctacggcgcg     1260
gacggtgtcc gccaccacca catggctctc ggcggtggct tccgcaatgc cgcggcgtcc     1320
cagggtcct tctttccgta caacctcgcc ggcgccggcg ccgatgtcgc gcccttcgac     1380
ggcggccgcg gcgtgctcga ggacgacatg tctgtcggcg ccgccgcgtc cggcacctgg     1440
gctggcgggg gcaccgaccg gcggaagaag cgcatgatca agaaccgcga gtccgccgcg     1500
cggtcccgcg cgcgcaagca ggcgtacgtc cgcgagctgg agacgaaggt gcagctgctg     1560
cagcaggaga acgagagcct ccgcgtcaag tacgacgagg taagcgggac atcgagagcc     1620
cccggcccct catatatatg gtcgcttttgc tcaaagctcg cgcgtggatt gggcagctgc     1680
gggagtccgt ggaggtggcg gtgccgatgg tgaggaagac cctgcagagg atgccgtccg     1740
cgccgttctg aggacattga ccggagatga gtcgaagcag gtggttgctc gttttgtttg     1800
ttttttgagg aggtgattaa gtaagtgact gattagtgag tggctgctgc ctagtgcttg     1860
gttactagta gtggtagaac tcagaactac atagatccag gaagcaagca agcaaatcct     1920
tcctgccatg gcggcctcaa tgtacataga tcccatgttt ttattaattt cgtctagctg     1980
ggggggcgtg cacctgccat ggcggcctcc tttatttagc tttatataag taggatgtag     2040
gatgtctacc atatgtgtgt agcttgggat taggctgcaa gaagataagc ctgcttgtac     2100
aaatatggct tcctggaaca atgacatttt ggggcgcaa cgcaagaaag atgaaagaac     2160
aatccaggaa gcagcaggtg tttcttctt cttcttcttt tgccccttcc atgatattcg     2220
cgtgtcaaag gctctcctaa agcgagtagt agtcttttgg tttggtgaat atttgctgtt     2280
ttcatgctgg tccctgctga tgtttgcgat gattttacaa tcagaaagag acgtttttg     2340
gttttgcctc cattctcttt ttgttgctca gctttggcga gggggaaagc cagtaatttc     2400
gacgataggg aacaaaaaat ggatcgaatt ttgggacccc tttgcttttc tgaaagatgg     2460
aacagaaggc aaacaaatcc tgactattgg gaggatctaa tttttccttt tttagacaat     2520
gtagagcagc tgcttcccta caccaggcag gaggcactgg accacagaca cgcaaacaga     2580
gctgcaagtc tgcctccccc caagcaccct gctccctccg atcta                     2625
```